United States Patent
Tuli

(10) Patent No.: US 11,149,300 B1
(45) Date of Patent: Oct. 19, 2021

(54) METHODS OF TREATING GASTROINTESTINAL MALIGNANCIES

(71) Applicant: Cedars-Sinai Medical Center, Los Angeles, CA (US)

(72) Inventor: Richard Tuli, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 34 days.

(21) Appl. No.: 16/256,840

(22) Filed: Jan. 24, 2019

Related U.S. Application Data

(60) Provisional application No. 62/622,779, filed on Jan. 26, 2018.

(51) Int. Cl.
*C12Q 1/6827* (2018.01)
*C12Q 1/6886* (2018.01)

(52) U.S. Cl.
CPC ......... *C12Q 1/6827* (2013.01); *C12Q 1/6886* (2013.01)

(58) Field of Classification Search
None
See application file for complete search history.

(56) References Cited

U.S. PATENT DOCUMENTS

2006/0142231 A1* 6/2006 Ashworth ............ A61K 31/502
514/44 A

OTHER PUBLICATIONS

Tuli et al. EBioMedicine. 2019. 40: 375-381 (Year: 2019).*
Moor et al. "Coordination of DNA Base Excision Repair by Protein-Protein Interactions" p. 1-20, available via URL: <intechopen.com/books/dna-repair-an-update/coordination-of-dna-base-excision-repair-by-protein-protein-interactions> (Year: 2018).*
Yang et al (World J Gastroenterology. Aug. 2016. 22(32): 7275-7288 (Year: 2016).*
Tuli et al Translational Oncology. Jun. 2014. 7(3): 439-445 (Year: 2014).*
Toll et al J. Clinical Oncology. 2016. 34, Suppl 4, Abstract 275 (Year: 2016).*
Chand et al., The Landscape of Pancreatic Cancer Therapeutic Resistance Mechanisms, 2016, Int. J. Bio. Sci., vol. 12(3), pp. 273-282.
clinicaltrials.gov, A Phase I Study of Veliparib (ABT-888) in Combination with Gemcitabine and Intensity Modulated Radiation Therapy in Patients with Locally Advanced, Unresectable Pancreatic Cancer, 2013, ClinicalTrials.gov Identifier: NCT01908478, 6 Pages.
Yang et al., Perspectives on the Combination of Radiotherapy and Targeted Therapy with DNA Repair Inhibitors in the Treatment of Pancreatic Cancer, 2016, World J. Gastroenterol., vol. 22(32), pp. 7275-7288.

* cited by examiner

*Primary Examiner* — Carla J Myers
(74) *Attorney, Agent, or Firm* — Nixon Peabody LLP; Linda B. Huber

(57) ABSTRACT

The present invention provides for the treatment of gastrointestinal malignancies such as pancreatic cancer. The treatment includes a combination of Poly (ADP-ribose) polymerase (PARP) inhibitor, radiation therapy, and chemotherapy. The invention also provides methods of identifying patients with DNA pathway repair gene defects who will benefit from the treatment methods described.

10 Claims, 32 Drawing Sheets

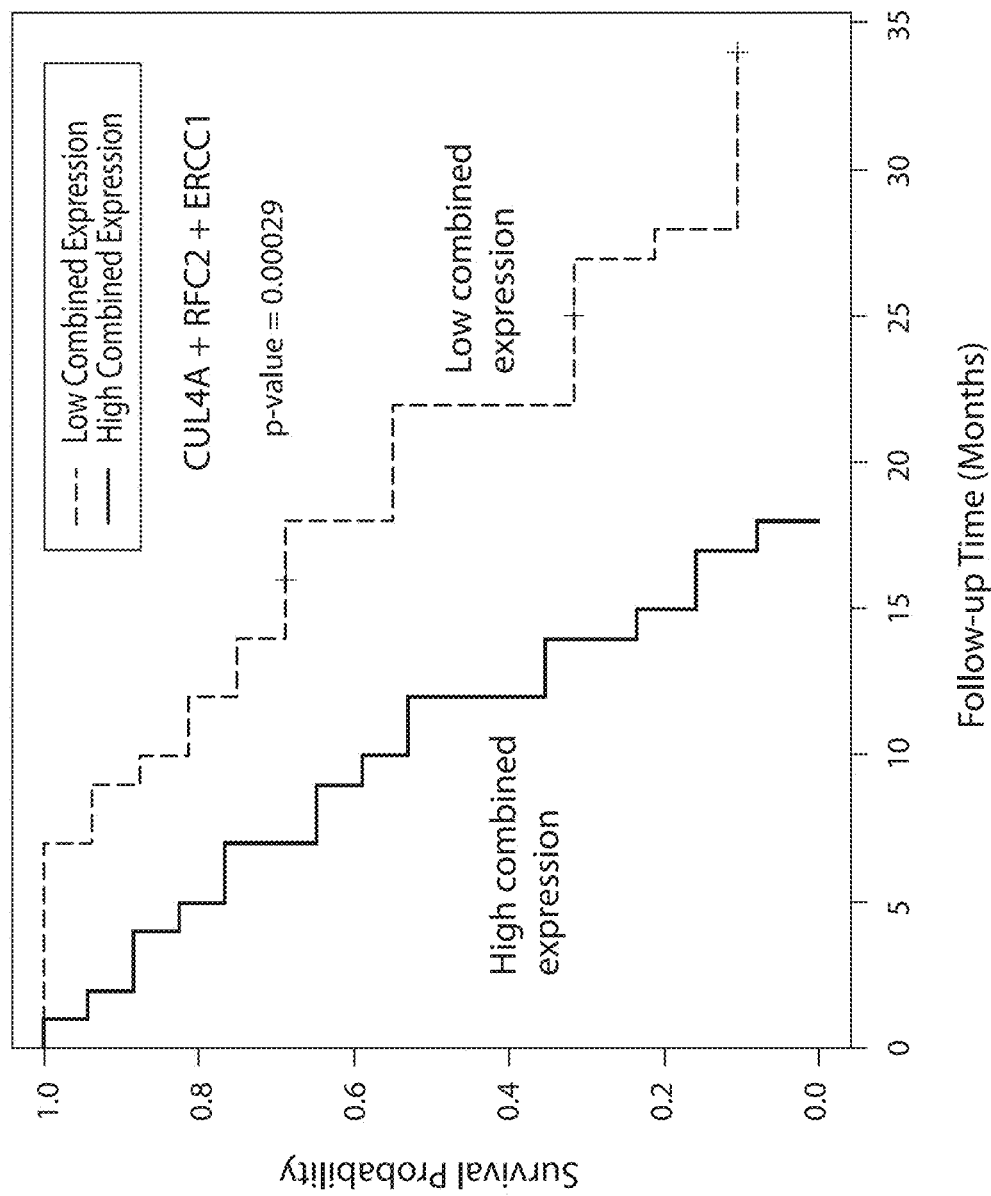

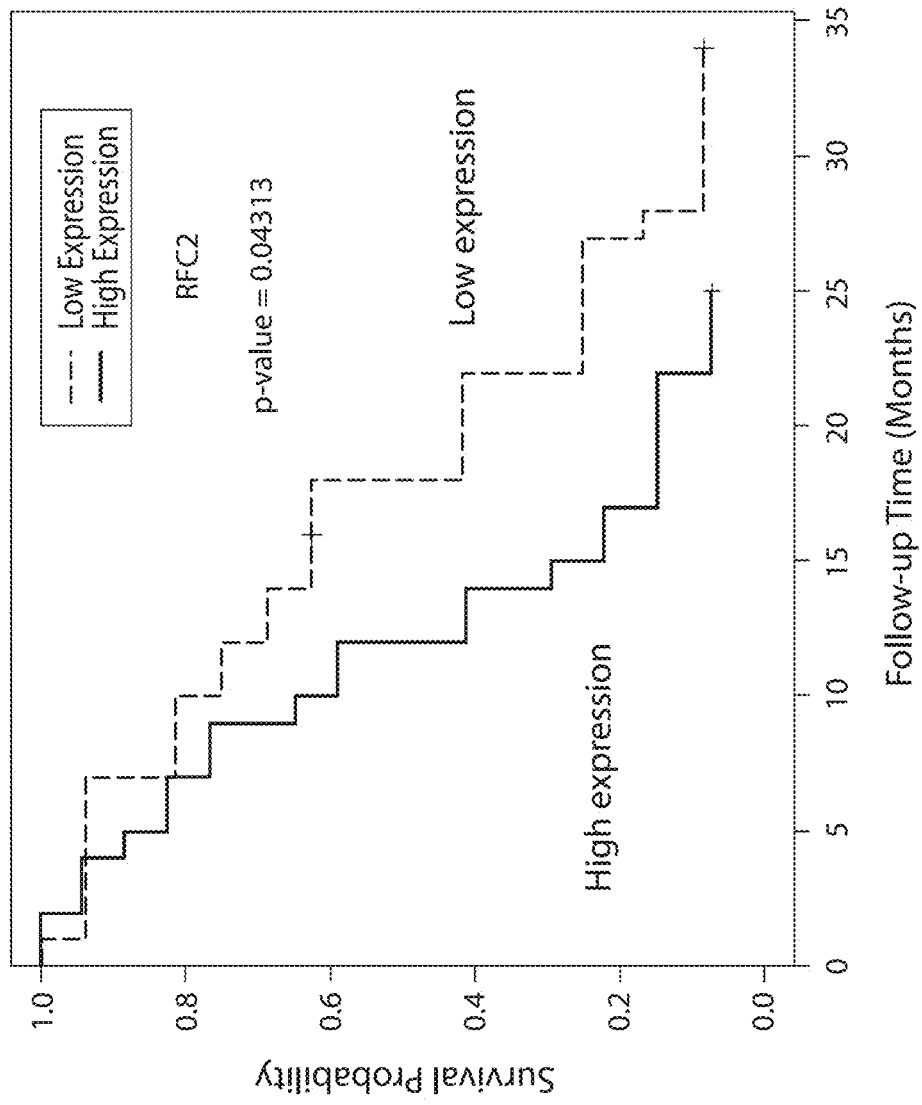

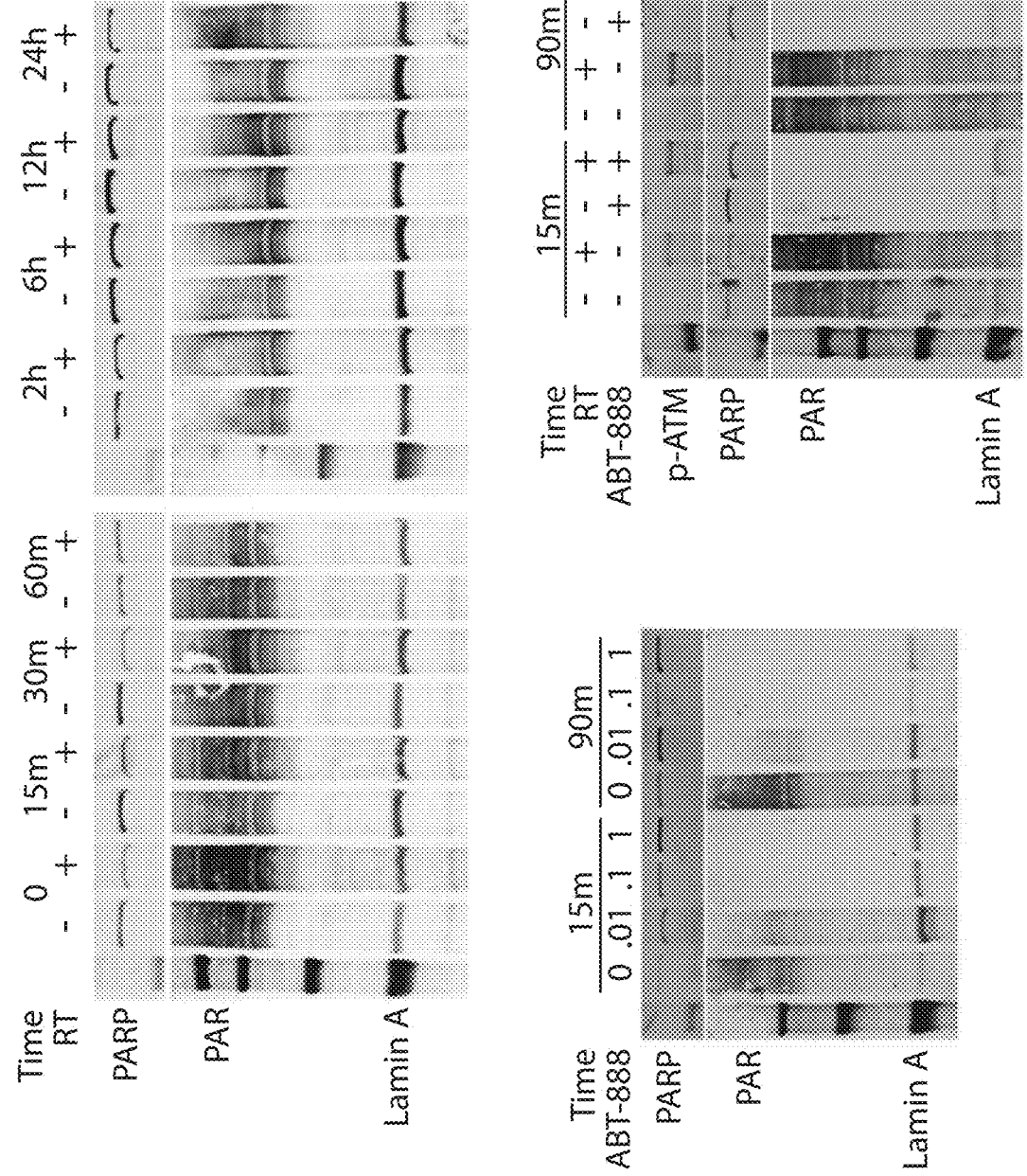

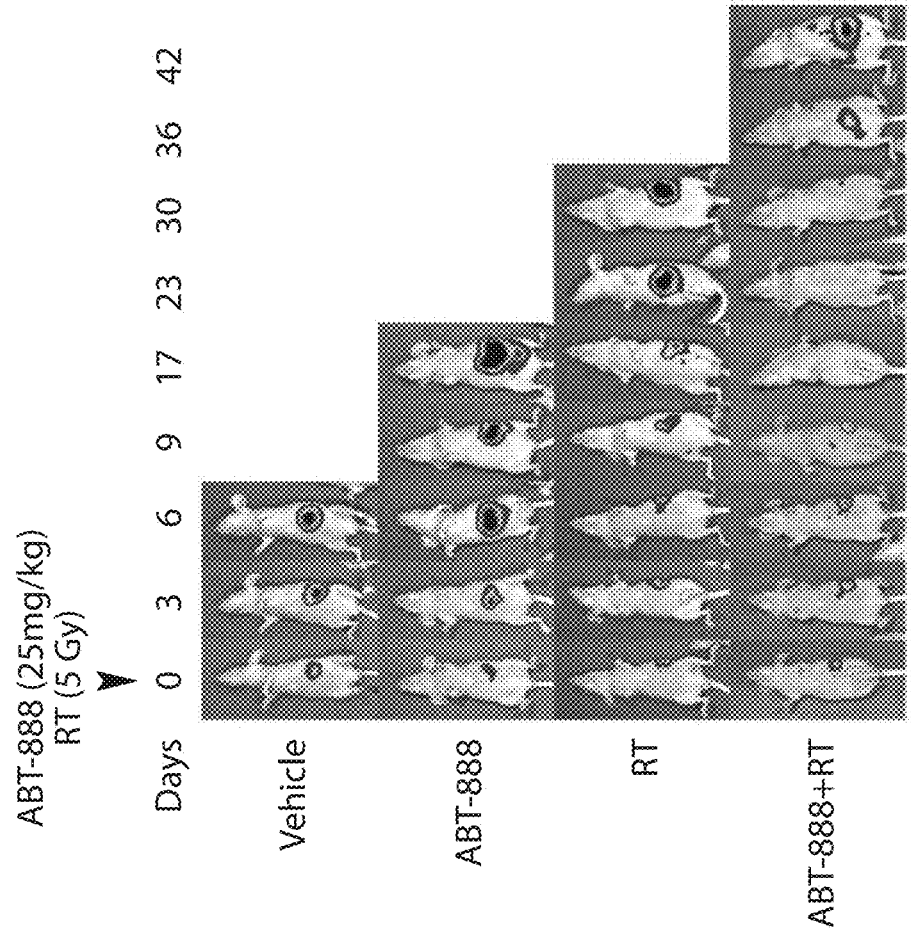

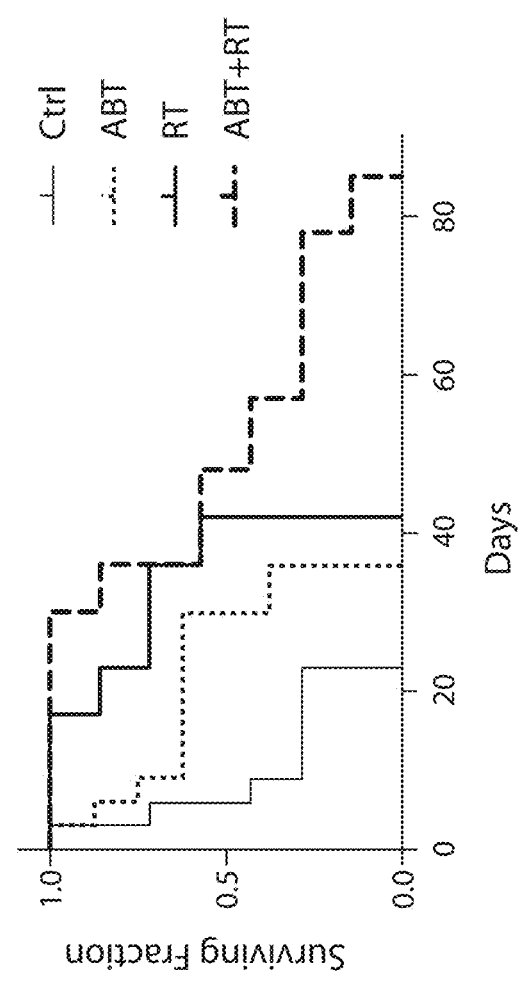

METHODS OF TREATING GASTROINTESTINAL MALIGNANCIES

CROSS-REFERENCE TO RELATED APPLICATIONS

This application includes a claim of priority under 35 U.S.C. § 119(e) to U.S. provisional patent application No. 62/622,779 filed Jan. 26, 2018, the entirety of which is hereby incorporated by reference.

FIELD OF THE INVENTION

This invention relates to gastrointestinal malignancies and treatment thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Approximately 40% of pancreatic cancer patients present with locally advanced disease. Long term outcomes for these patients are poor (5y OS<5%) with minimal advances made over the past 30 years relative to other malignancies. At least one-third of these patients die due to progression of uncontrolled local disease. Conversion to resectability leads to a 2-3-fold improvement in overall survival, yet only occurs in 10-15% of patients. Limited prospective data is available regarding the clinical value of radiotherapy after the use of multiagent chemotherapies in locally advanced pancreatic cancer.

Radiotherapy is currently recommended after multi-agent chemotherapy in patients without progression of disease or those who need palliation of pain or bleeding due to tumor infiltration of small bowel or stomach. Just as surgical resection provides local tumor control that translates to a chance for long-term survival, recent evidence indicates that enhancement of local tumor control with definitive, ablative doses of radiation can offer a similar long-term outcome to resection. A limitation is that the ablative techniques are not yet scalable.

Radiotherapy dose escalation is not practical as a community standard because it is limited by proximity of pancreatic tumors to adjacent bowel. Additionally, the use stereotactic body radiation therapy in locally advanced patients has been associated with a risk of duodenal ulcers with no clear improvement in outcomes over conventional chemoradiation treatments. Stereotactic Body Radiation Therapy (SBRT) is more convenient for patients but will always be limited by the normal tissue tolerance of the adjacent bowel. Modern radiation treatment techniques, including IMRT and image guidance, permit us to safely deliver relatively high doses of fractionated radiation to the primary tumor. Conformal image guided fractionated radiation with a sensitizing agent has the greatest potential to optimize the therapeutic ratio. To date, no clinically effective radiosensitizers other than fluororouracil and gemcitabine have been identified. Additionally, although pancreatic cancer is known to be a biologically heterogeneous disease, no predictive biomarkers or biologically targeted therapies have been identified. There is a great need for chemoradiation sensitizing strategies in locally advanced pancreatic cancer in order to improve local control, resectability rates, and survival.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a process, comprising obtaining a biological sample from a subject who desires determination regarding treatment of a gastrointestinal (GI) malignancy with Poly (ADP-ribose) polymerase (PARP) inhibitor; assaying the biological sample to determine the presence or absence of a DNA repair pathway gene defect; and determining the presence or absence of the DNA repair pathway gene defect in the biological sample.

In various embodiments, the DNA repair pathway can be nucleotide excision repair pathway, fanconi anemia pathway, DNA replication pathway, base excision repair pathway, or a combination thereof. In various embodiments, the DNA repair pathway gene in the nucleotide excision repair pathway can be RFC2, ERCC1, XPA, CUL4A, or a combination thereof; the fanconi anemia pathway is ERCC1, FANCE, or both; the DNA replication pathway is RFC2, MCM4, or both; and the base excision repair pathway is NEIL1, PARP3, APEX2, or a combination thereof. In various embodiments, the DNA repair pathway gene can be RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, MLH1, or a combination thereof.

In various embodiments, the GI malignancy can be pancreatic cancer. In various embodiments, the pancreatic cancer can be locally advanced pancreatic cancer.

In various embodiments, the process can further comprise identifying the subject as a subject for treatment with the PARP inhibitor based on the presence of a DNA repair pathway gene defect.

In various embodiments, the process can further comprise selecting a PARP inhibitor as a therapy for the subject if the presence the DNA repair pathway gene defect in the biological sample is detected.

Various embodiments of the present invention provide for a method of treating a gastrointestinal (GI) malignancy, comprising: administering a therapeutically effective amount of a composition comprising a Poly (ADP-ribose) polymerase (PARP) inhibitor to a subject determined to have a defect in a DNA repair pathway gene to treat the gastrointestinal (GI) malignancy.

In various embodiments, the method can further comprise administering a therapeutically effective amount of radiation therapy and administering a therapeutically effective amount of chemotherapy, or both. In various embodiments, the PARP inhibitor can be talozoparib, olaparib, and/or niraparib.

In various embodiments, the GI malignancy can be pancreatic cancer. In various embodiments, the pancreatic cancer can be locally advanced pancreatic cancer.

In various embodiments, the DNA repair pathway gene can be RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, MLH1, or a combination thereof.

In various embodiments, the PARP inhibitor is olaparib, the radiation therapy can be intensity-modulated radiation therapy (IMRT), and the chemotherapy is gemcitabine. In various embodiments, the PARP inhibitor is olaparib and can be administered 25 mg twice per day, the radiation therapy is intensity-modulated radiation therapy (IMRT) and can be administered at a dose of 36Gy in 15 fractions with 5 fractions per week, and the chemotherapy is gemcitabine and is administered 600 mg/m² once per week for 3 weeks. In various embodiments, the PARP inhibitor can be olaparib and can be administered 25 mg twice per day, the radiation therapy can be intensity-modulated radiation therapy (IMRT) and can be administered at a dose of 36Gy in 15 fractions with 5 fractions per week, and the chemotherapy can be gemcitabine and can be administered 400 mg/m² or 250 mg/m² once per week for 3 weeks, or chemotherapy is not administered. In various embodiments, the PARP inhibitor can be olaparib and can be administered 50 mg or 100 mg twice per day, the radiation therapy can be intensity-modulated radiation therapy (IMRT) and can be administered at a dose of 36Gy in 15 fractions with 5 fractions per week, and the chemotherapy can be gemcitabine and can be administered 600 mg/m² once per week for 3 weeks.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 7A-7C depicts in accordance with various embodiments of the invention, the VelGemRad transcriptome analysis of DNA Damage Response (DDR) overall survival (OS) in the Base Excision Repair Pathway (BER), Nucleotide Excision Repair Pathway (NER) and Mismatch Repair Pathway (MMR). Median OS (biomarker (+) versus biomarker (−). BER—14.5 months versus 9 months, p<0.05; NER—22 months versus 12 months, p<0.001; MMR—18 months versus 12 months, p<0.05.

FIG. 24A-24B depicts in accordance with various embodiments of the invention, PARP and PAR expression with and without radiation therapy over time (FIG. 24A, top), PARP and PAR expression with ABT-888 over time (FIG. 24A, bottom), caspase activity with various treatments (FIG. 24B, Top) and PARP activity as a percentage of baseline ((FIG. 24B, bottom)).

FIG. 25A-25C depicts in accordance with various embodiments of the invention, treatment with ABT-888, radiation therapy (RT), and ABT-888 and RT (FIG. 25A) and tumor changes (FIG. 25B) and survival fraction (bottom panel) over time following treatment.

DETAILED DESCRIPTION

Figure 1:
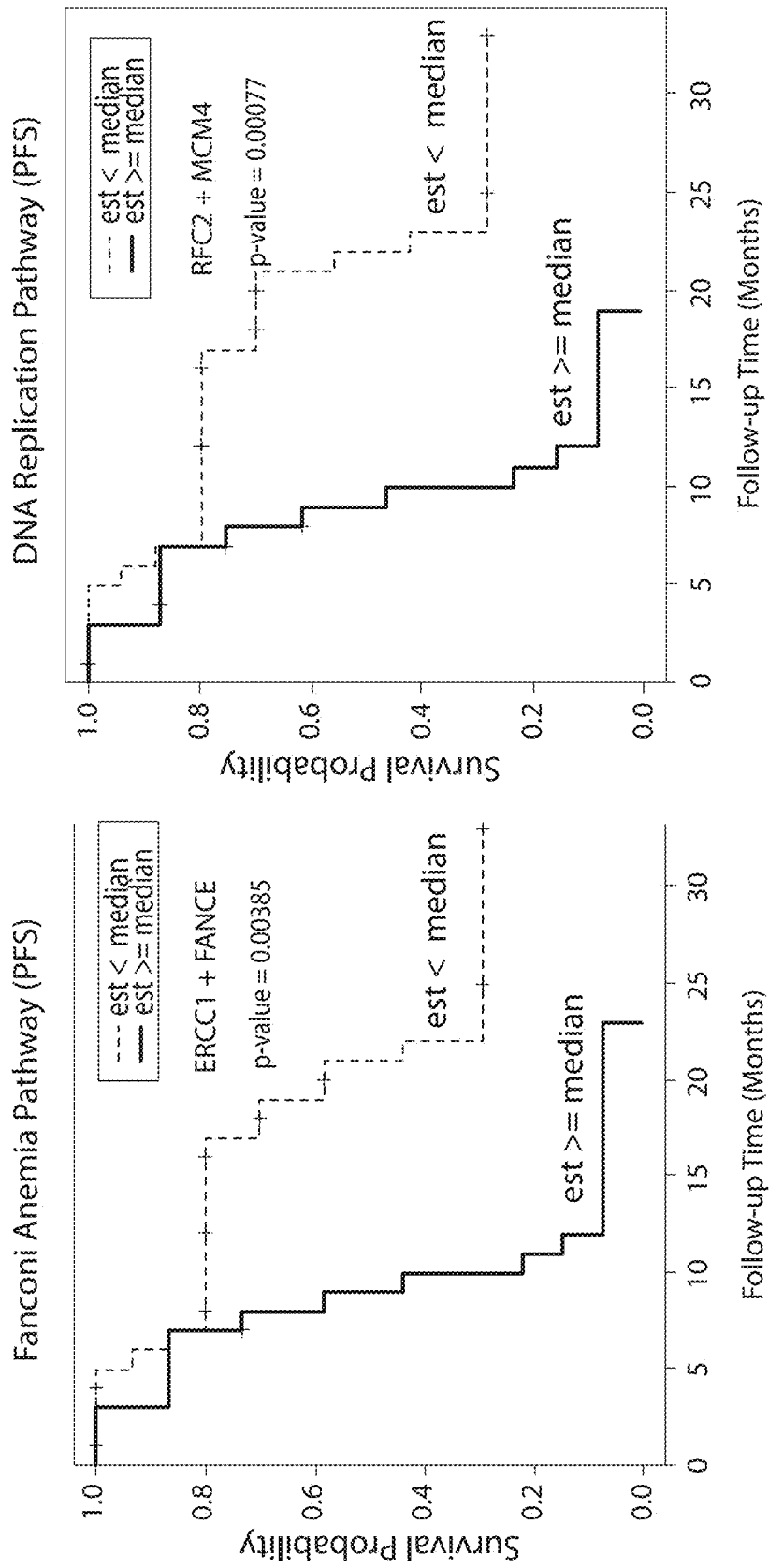
FIG. 1 depicts in accordance with various embodiments of the invention, the survival probability in the Fanconi Anemia pathway (ERCC1+FANCE genes) and the DNA Replication Pathway (RFC2+MCM4 genes).
Figure 2:
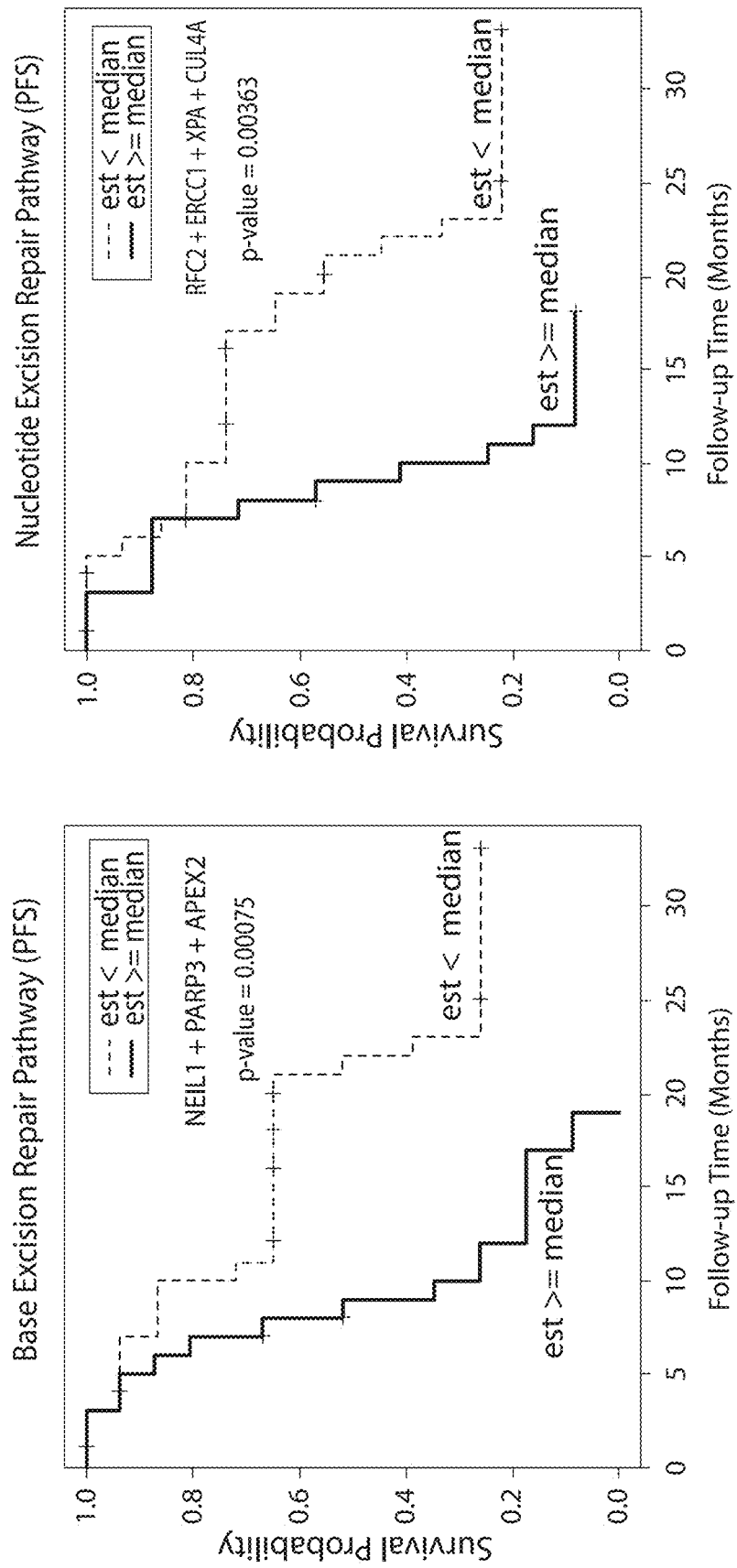
FIG. 2 depicts in accordance with various embodiments of the invention, the survival probability in the Base Excision Repair pathway (NEIL1+PARP3+APEX2 genes) and the Nucleotide Excision Repair pathway (RFC2+ERCC1+XPA+CUL4A genes).
Figure 3:
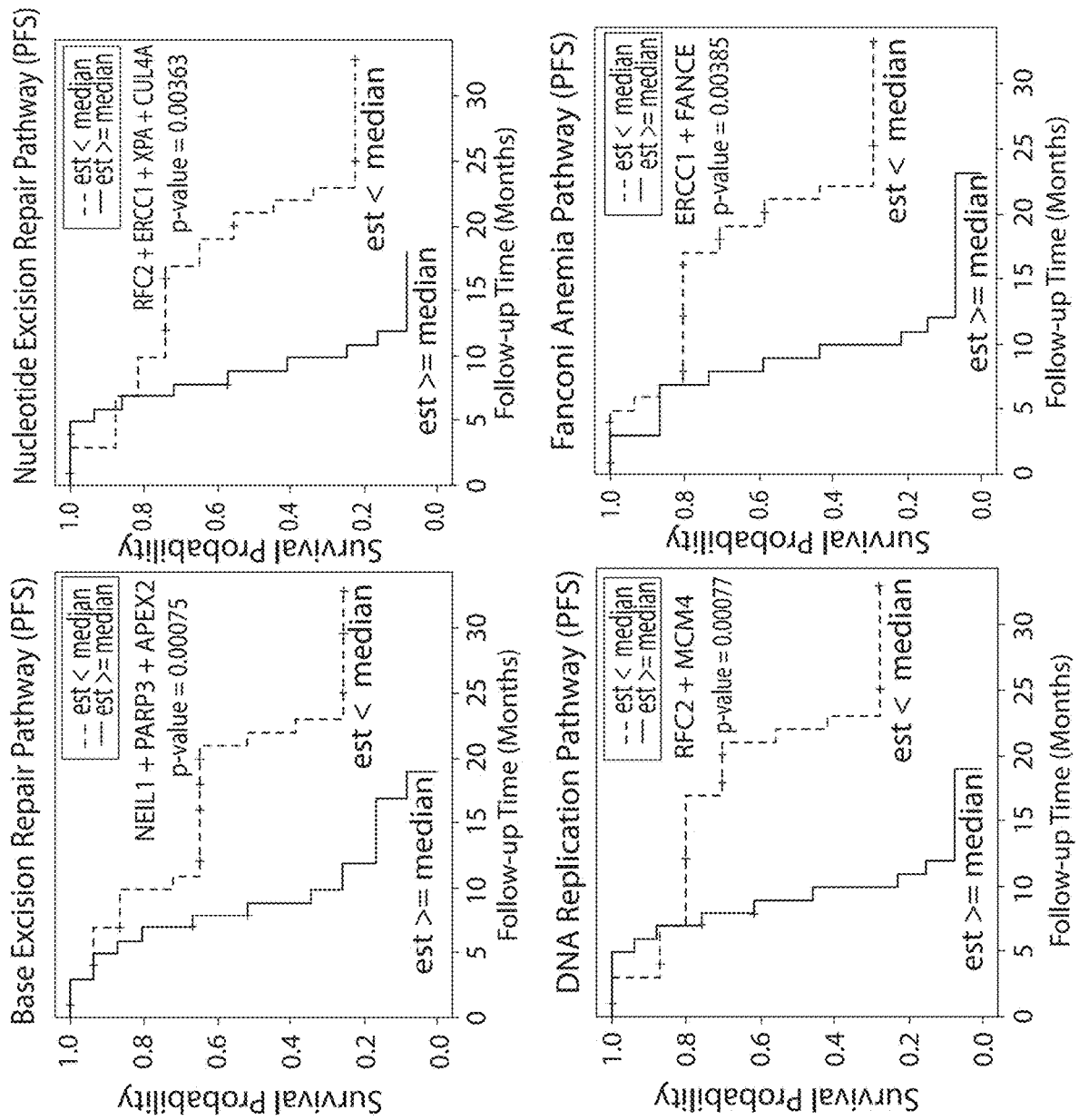
FIG. 3 depicts in accordance with various embodiments of the invention, the survival probability in the Base Excision Repair pathway (NEIL1+PARP3+APEX2 genes), the Nucleotide Excision Repair pathway (RFC2+ERCC1+XPA+CUL4A genes), DNA Replication pathway (RFC2+MCM4 genes) and the Fanconi Anemia pathway (ERCC1+FANCE genes).
Figure 4:
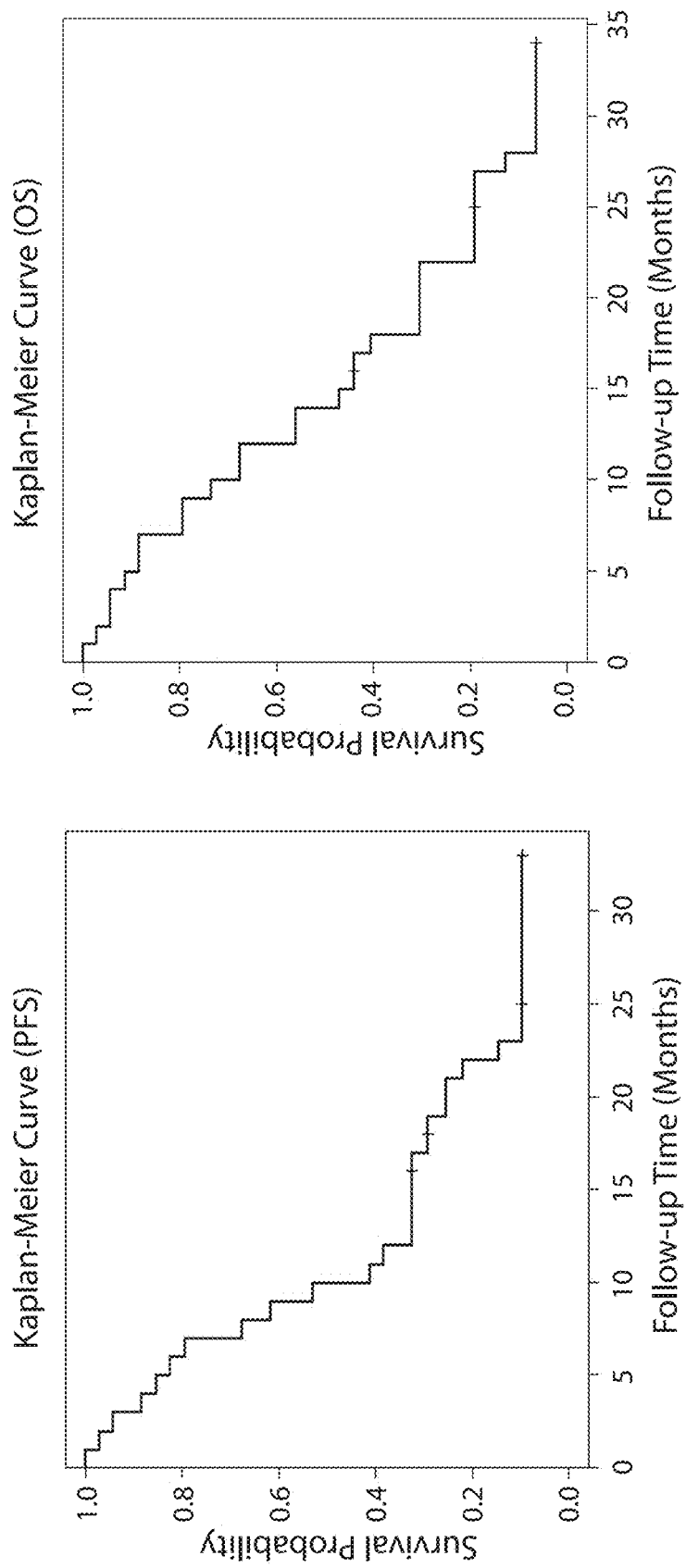
FIG. 4 depicts in accordance with various embodiments of the invention, the efficacy of the combination therapy veliparib (vel), gemcitabine (gem) and radiation therapy (intensity modulated radiation therapy—rad). All patients—median progression free survival (PFS) 9.8 months (95% CI:8.4-18.6) and median overall survival (OS) 14.6 months (95% CI: 11.6-21.8).
Figure 5:
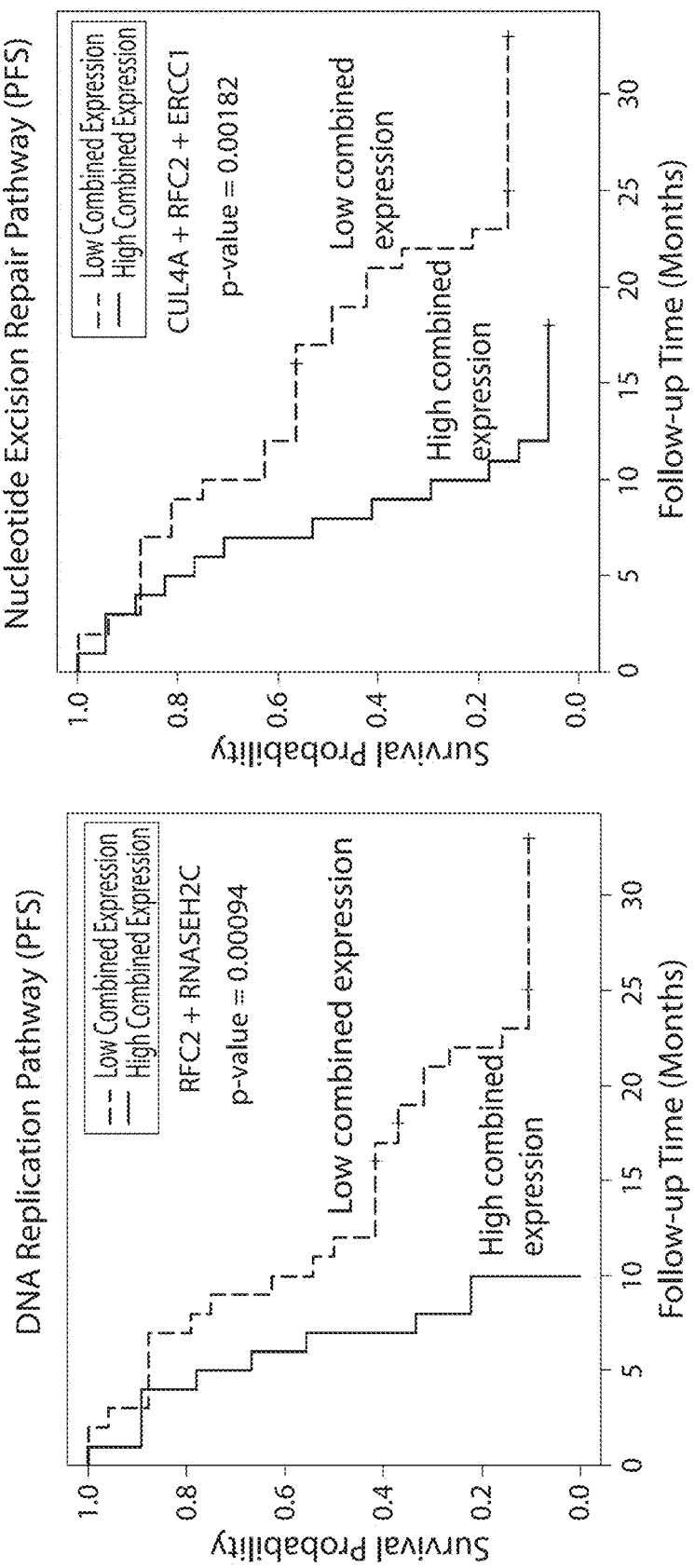
FIG. 5 depicts in accordance with various embodiments of the invention, the VelGemRad transcriptome analysis DNA Damage Response (DDR) progression free survival (PFS) in the DNA Replication Pathway (DNAR) and Nucleotide Excision Repair Pathway (NER). Median PFS (biomarker (+) versus biomarker (−). NER—17 months versus 8 months, p<0.01; DNAR—11.5 months versus 7 months, p<0.001.
Figure 6:
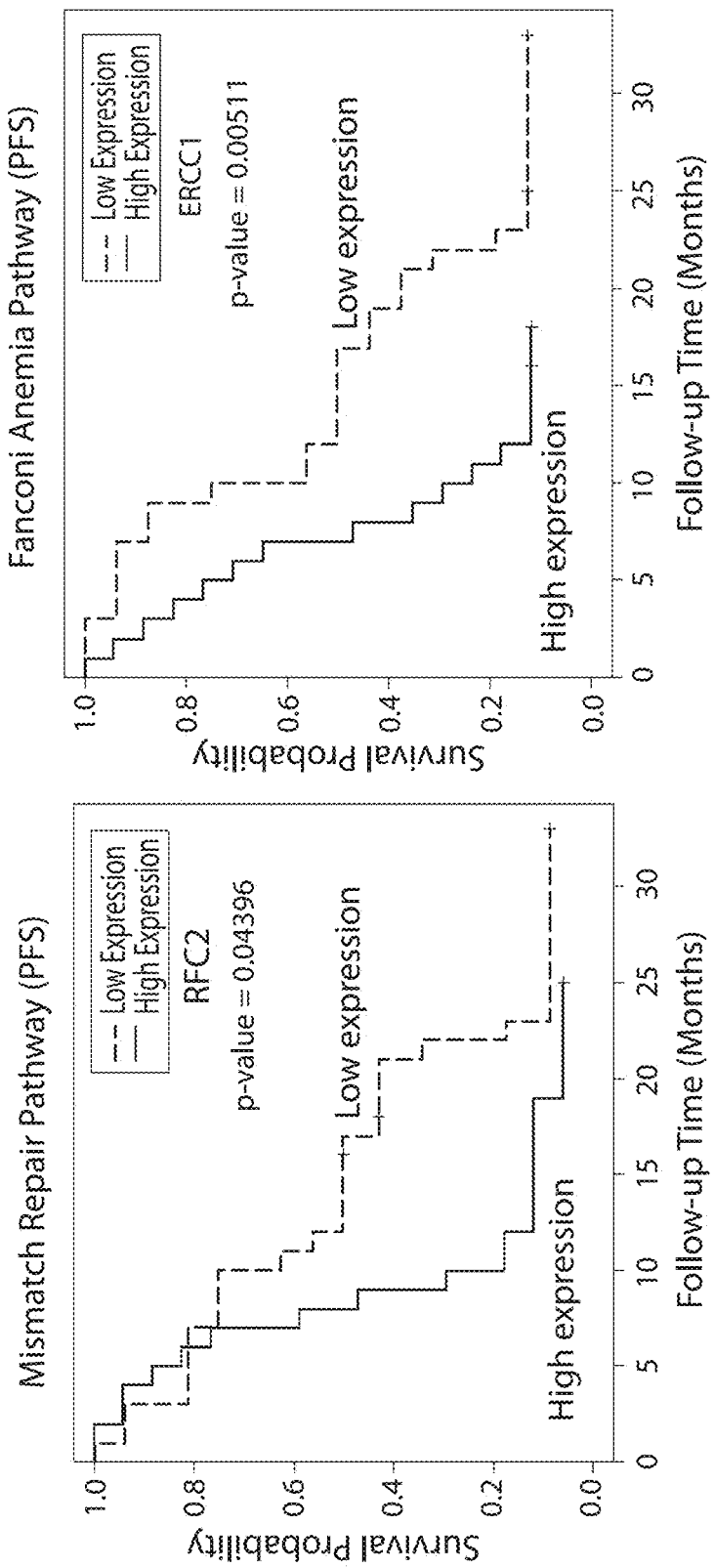
FIG. 6 depicts in accordance with various embodiments of the invention, the VelGemRad transcriptome analysis DNA Damage Response (DDR) progression free survival (PFS) in the Mismatch Repair Pathway (MMR) and the Fanconi Anemia Pathway (FA). Median PFS (biomarker (+) versus biomarker (−). MMR-14.5 months versus 8 months, p<0.05; FA—14.5 months versus 7 months, p<0.001.
Figure 7A:
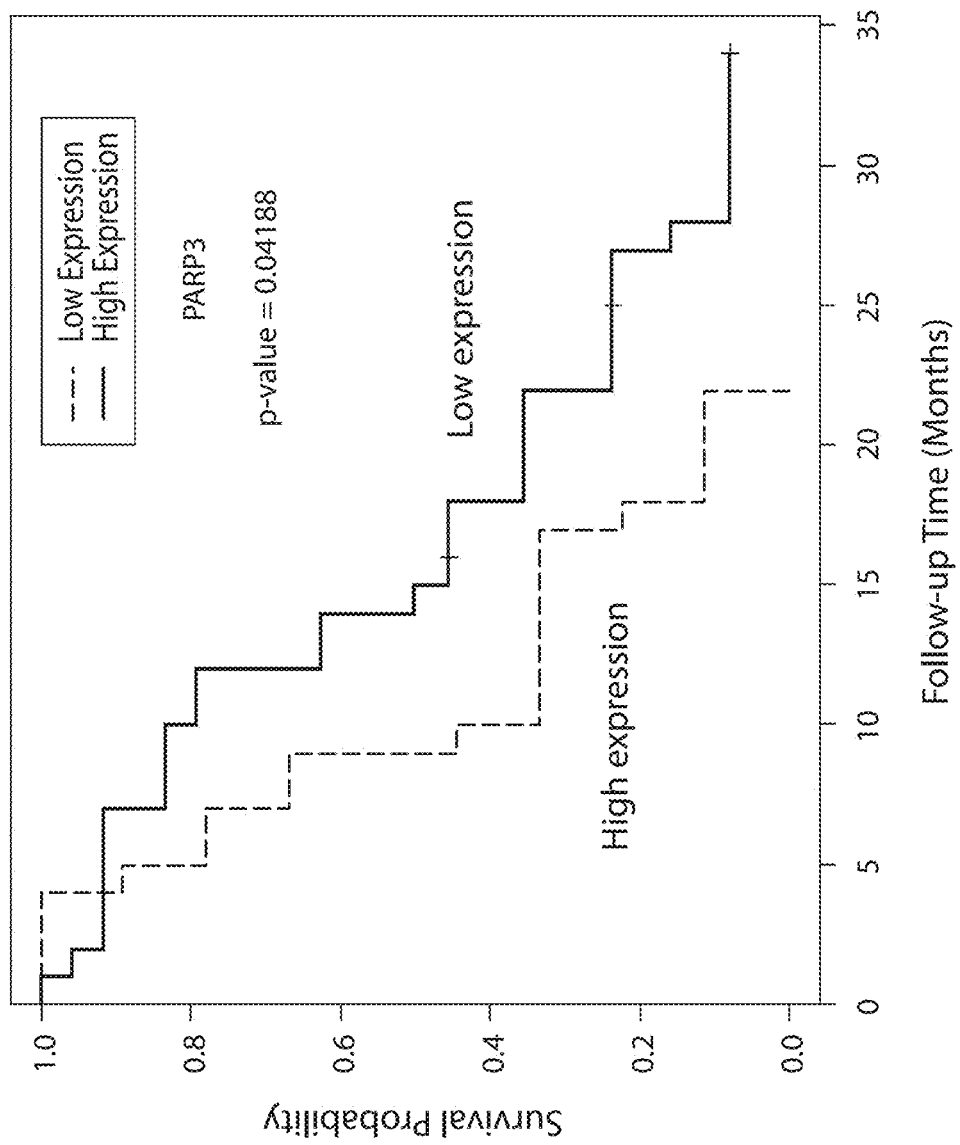
Figure 8:
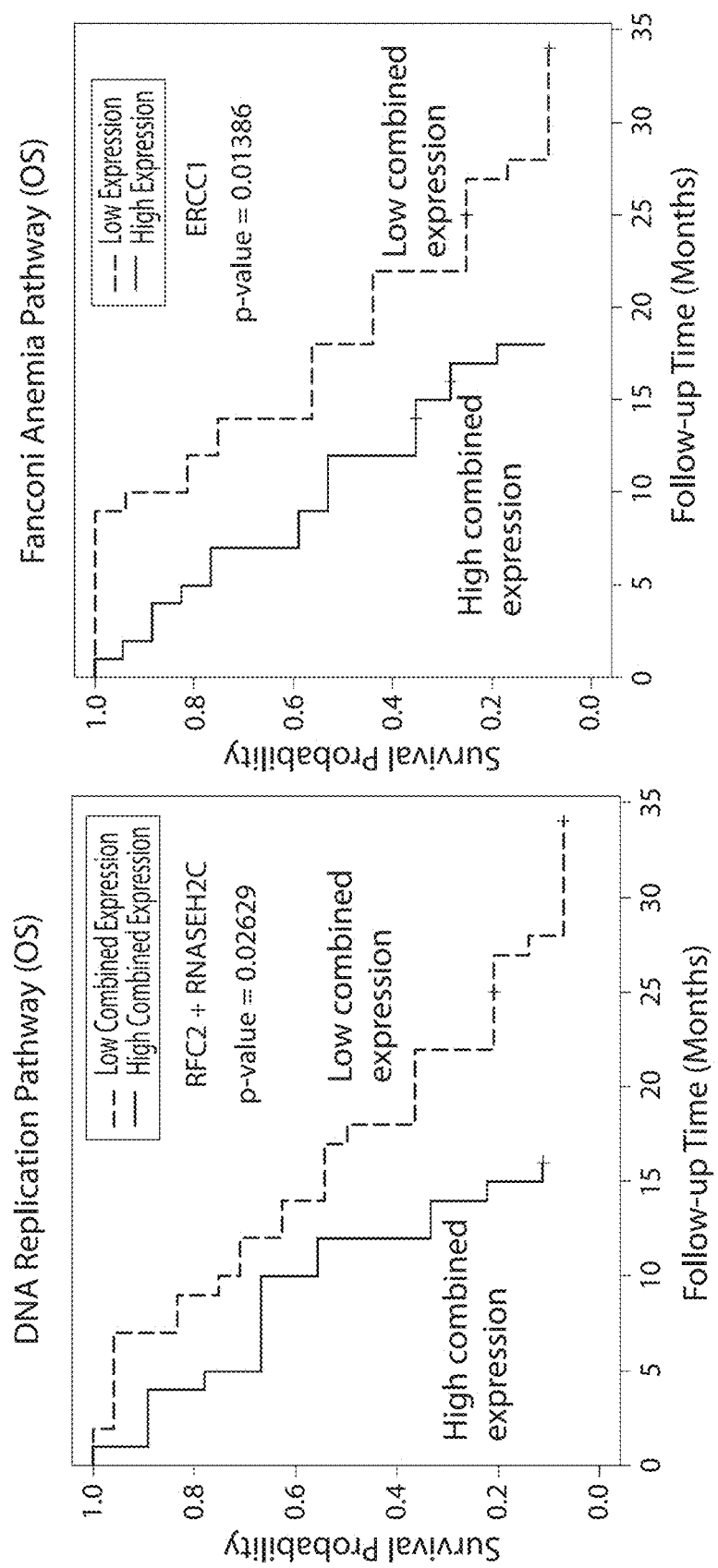
FIG. 8 depicts in accordance with various embodiments of the invention, the VelGemRad transcriptome analysis of DNA Damage Response (DDR) overall survival (OS) in the DNA Replication Pathway (DNAR) and the Fanconi Anemia Pathway (FA). Median OS (biomarker (+) versus biomarker (−). DNAR—17 months versus 12 months, p<0.05; FA—18 months versus 12 months, p<0.05.
Figure 9:
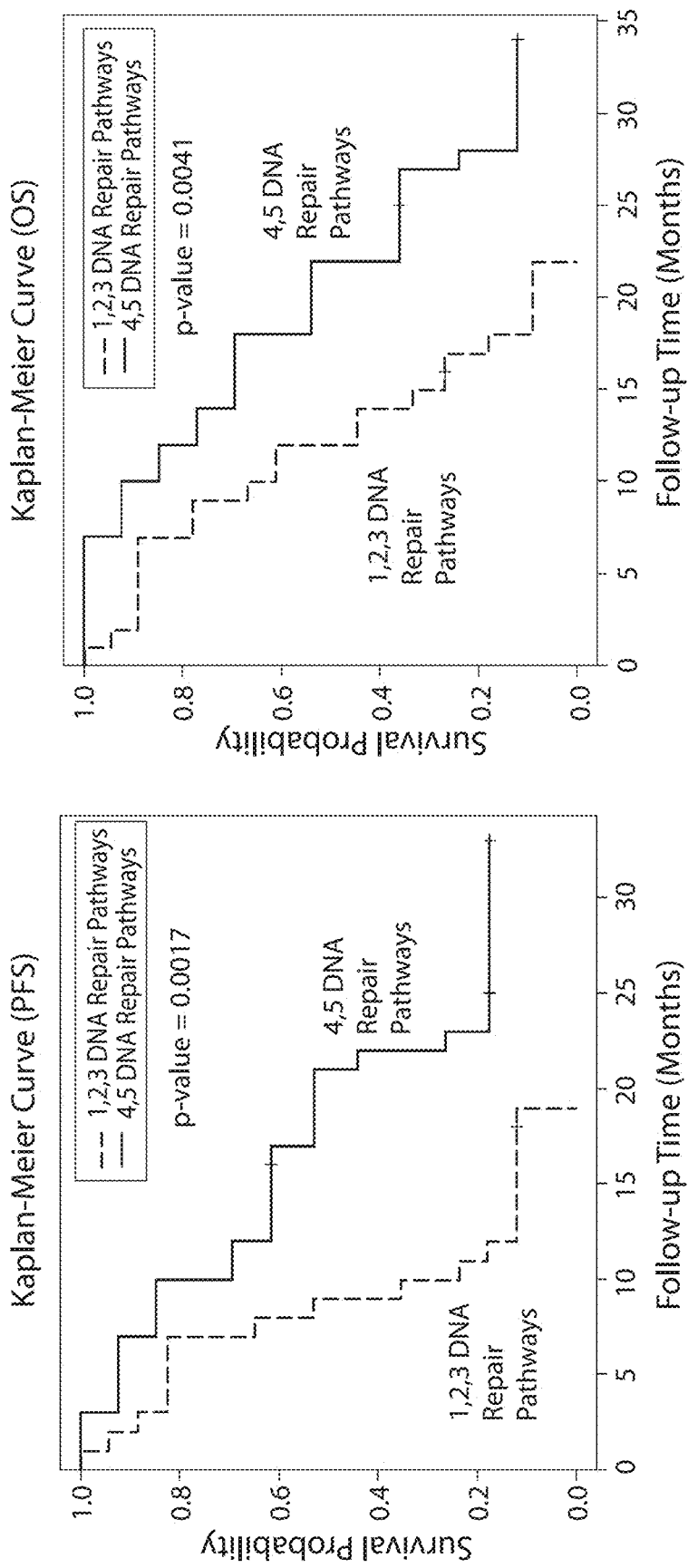
FIG. 9 depicts in accordance with various embodiments of the invention, the VelGemRad transcriptome analysis of DNA Damage Response (DDR). Kaplan-Meier Curve—Progression free survival (PFS) and Kaplan-Meier Curve—overall survival (OS). 73%, 58%, 39% and 27% had alterations in more than 1, 2, 3 or 4 pathways, respectively. Patients with alterations in 4 or more of the RNA biomarker pathways had significantly improved PFS (21 months versus 9 months, P=0.0017) and OS (22 months versus 12 months, p=0.0041) compared to patients with alteration in up to 3 pathways.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); and Singleton, *Dictionary of DNA and Genome Technology* 3$^{rd}$ ed., Wiley-Blackwell (Nov. 28, 2012).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Terms such as "treating" or "treatment" or "to treat" or "alleviating" or "to alleviate" refer to therapeutic treatment and/or prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Thus, those in need of treatment include those already with the disorder; those prone to have the disorder; and those in whom the disorder is to be prevented.

The term "subject" refers to any animal (e.g., a mammal), including, but not limited to humans, non-human primates, rodents, and domestic and game animals, which is to be the recipient of a particular treatment. In various embodiments, the subject is human. Non-primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. The terms "subject" and "patient" are used interchangeably herein. In various embodiments, a subject can be one who has been previously diagnosed with or identified as suffering from or having a condition in need of treatment. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits symptoms for a condition). A "subject in need" of treatment for a particular condition can be a subject having that condition, diagnosed as having that condition, or at risk of developing that condition.

The term "therapeutically effective amount" refers to an amount of a polypeptide, small molecule, or other drug, or doses of radiation effective to "treat" a disease or disorder in a subject or mammal. In the case of cancer and/or cancer metastasis, the therapeutically effective amount of the drug can reduce the severity of cancer symptoms. These include, but are not limited to, fatigue, weight loss, reduced appetite, pain, skin changes, change in bowel or bladder function, unusual bleeding, fever, nausea, vomiting, lumps or tissue masses.

"Biological sample" as used herein means any biological material from which nucleic acids and/or proteins can be obtained. As non-limiting examples, the term encompasses cells or other bodily fluid or tissue, including but not limited to tissue obtained through surgical biopsy or surgical resection. Alternatively, a sample can be obtained through primary patient derived cell lines, or archived patient samples in the form of preserved samples, or fresh frozen samples. Additional examples include, blood, plasma, and peripheral blood mononuclear cells from blood samples.

As used herein, "GI" refers to gastrointestinal. Gastrointestinal malignancies includes, but is not limited to, stomach cancer, pancreatic cancer, gastrointestinal stromal tumor, colorectal cancer, esophageal cancer, small intestine cancer, squamous cell skin cancer, anal cancer, duodenal cancer, familial adenomatous polyposis, intraductal papillary mucinous neoplasm, digestive system neoplasm, carcinoid, krukenberg tumor, juvenile polyposis syndrome, gastric lymphoma, hepatoblastoma, pseudomyxoma peritonei, gardner's syndrome, MALT lymphoma, and linitis plastic.

"DNA Repair Pathway Gene Defects" as used herein refers to the alteration or modification of a DNA repair pathway gene. The alteration or modification can include, but is not limited to, the absence or altered expression of the DNA repair gene, and/or mutations in the DNA repair gene (such as, a substitution, insertion, deletion or frameshift in the nucleotides of the DNA repair gene).

Select or selecting a therapy as used herein, includes but is not limited to selecting, choosing, prescribing, advising, recommending, instructing, or counseling the subject with respect to the treatment.

The use of the combination of gemcitabine and radiation in the treatment of locally advanced pancreatic cancer was developed. Gemcitabine is an effective radiation sensitizer, however, outcomes for locally advanced patients remains poor even with this combination. There is a need in the art for treatments that improve clinical outcomes in patients with pancreatic cancer and methods to identify patients with this disease who harbor a genetic abnormality which may enhance response to these treatments.

As described herein, the inventors discovered the use of a PARP inhibitor to treat a subset of patients with a gastrointestinal (GI) malignancy and a defect in DNA repair pathways genes to enhance the response to treatment. The current invention describes methods of identifying and treating subjects with gastrointestinal malignancies. The invention further provides for a method of selecting a therapy for a subject with gastrointestinal malignancies.

Locally advanced pancreatic cancer (LA) has a dismal prognosis with current treatment modalities. Preclinical studies have demonstrated radiosensitization of orthotopic pancreatic tumors with the PARP-1/2 inhibitor, veliparib (ABT-888). A phase I trial of veliparib, gemcitabine and radiotherapy (RT) was conducted to determine the maximum tolerated dose, safety and clinical activity of this regimen in patients with and without DNA repair defects.

Veliparib (ABT-888) is an orally available, small molecule inhibitor of poly (ADP-ribose) polymerase (PARP). PARP is an essential nuclear enzyme that plays a role in recognition of DNA damage and facilitation of DNA repair. Therefore, inhibition of PARP is expected to enhance the effects of DNA damage. Expression of PARP is higher in tumor cells as compared to normal cells. This overexpression has been linked to drug resistance and the ability of tumor cells to withstand genotoxic stress. Hence, without being bound to any particular theory, it is anticipated that PARP inhibitors will function as sensitizing agents for chemotherapy and radiation therapy that are designed to cause DNA damage.

Mechanism of Action

Poly (ADP-ribosyl)ation (PAR) occurs after single or double-stranded DNA damage and represents the posttranslational modification of histones and other nuclear proteins by PARP. Based on conserved genetic sequences, encoded for by 18 different genes, 18 nuclear proteins have been classified as members of the PARP superfamily. The superfamily is further subdivided into three branches, the PARP-1 group, the tankyrase group, and other PARP enzymes. The PARP-1 group of NAD+-dependent enzymes has been extensively studied, and its members PARP-1 and PARP-2 are generally considered as the primary enzymes involved in DNA repair. PAR has been implicated in many cellular processes including replication, transcription, differentiation, gene regulation, protein degradation, and spindle maintenance. Enhanced PARP-1 expression and/or activity in tumor cells, as compared to normal cells, has been demonstrated in malignant lymphomas, hepatocellular carcinoma, cervical carcinoma, colorectal carcinoma, non-Hodgkin's lymphoma, leukemic lymphocytes, and colon adenomatous polyps. PARP-1 and PARP-2 are nuclear proteins and are the only members of the PARP family with zinc-finger DNA binding domains. These domains localize PARP-1 and PARP-2 to the site of DNA damage. PARP-1 is highly conserved and has three structural domains (N-terminal DNA-binding domain; automodification domain, and the NAD+-binding domain). The catalytic domain is located at the C-terminus end of the protein. In knockout mouse models, deletion of PARP-1 is sufficient to impair DNA repair. The residual PARP-dependent repair activity (~10%) is due to PARP-2. This suggests that only PARP-1 and PARP-2 need to be inhibited to impair DNA repair.

The zinc finger domain of PARP binds to both single- and double-stranded DNA breaks, resulting in increased catalytic activity. Once activated, PARP cleaves NAD+ and attaches multiple ADP-ribose units to the target nuclear protein. This results in a highly negative charge on the target protein and affects its function. Overactivation of PARP can be induced by DNA damage, leading to the depletion of NAD+ and energy stores and, thus, cellular demise by necrosis. An alternate mechanism has been identified where PARP overactivation can induce cell death through apoptosis by releasing the Apoptosis Inducing Factor (AIF) from mitochondria. Consequently, multiple mechanisms to prevent overactivation of PARP exist. First, auto-PAR negatively regulates PARP activity. In addition, the cleavage of PARP by caspases yields a peptide fragment that acts as a transdominant negative inhibitor for uncleaved PARP. PAR of proteins is a dynamic process with a short half-life (t1/2) of <1 min. The enzymes responsible for degrading these polymers are poly(ADP-ribose) glycohydrolase (PARG), which cleaves riboseribose bonds, and ADP-ribosyl protein lyase, which removes the protein proximal to the ADP-ribose monomer.

Increased PARP activity is one of the mechanisms by which tumor cells avoid apoptosis caused by DNA damaging agents. PARP activity is essential for the repair of single-stranded DNA breaks through the base excision repair (BER) pathways. Therefore, inhibition of PARP sensitizes tumor cells to cytotoxic agents (e.g. alkylators [temozolomide, cyclophosphamide, BCNU] and topoisomerase I inhibitors [irinotecan, camptothecin, topotecan]) which induce DNA damage that would normally be repaired through the BER system. A significant therapeutic window appears to exist between a PARP inhibitor's ability to potentiate therapeutic benefit versus potentiation of undesirable side effects. As expected, PARP inhibitors do not potentiate agents that do not cause DNA damage.

Ionizing radiation induces both double- and single-stranded DNA breaks. While part of the radiosensitization caused by PARP inhibition is through the inhibition of the single-stranded break repair pathways, it appears likely that repair of double-stranded breaks, which are thought to be more cytotoxic, is also affected. Double-stranded breaks are strong activators of PARP-1, resulting in PARP-1 mediated activation of DNA-PK and Ku80, important components of the non-homologous end-joining (NHEJ) double-stranded break repair pathway. Also, small molecule inhibitors of PARP can directly inhibit the repair of double-stranded breaks. Thus, without being bound to any particular theory, it is likely that PARP activity is important for repair of both the single- and double-stranded stranded DNA breaks caused by ionizing radiation.

The inventors aimed to improve clinical outcomes in patients with pancreatic adenocarcinoma using PARP inhibitor therapy in combination with chemotherapy and radiotherapy and to identify a select subset of patients with this disease who harbor genetic abnormalities which may enhance response to these treatments The present invention is based, at least in part, on these finding. The present invention addresses the need in the art for methods of identifying and treating subjects with gastrointestinal malignancies. The invention further provides for a method of selecting a therapy for a subject with gastrointestinal malignancies. As further discussed herein, in all patients with locally advanced and borderline resectable pancreatic cancer, the combination Veliparib, Gemcitabine and radiation therapy (VelGemRad) can help patients live longer and prevent the cancer from returning relative to standard of care therapies. In patients who have inherited or acquired defects in DNA damage repair, this treatment combination can be even more effective. It can also provide benefit to those patients with early stage pancreatic cancer and typically receive surgery up front.

Subject Identification/DNA Repair Pathway Defect Detection

Various embodiments of the present invention provide for a process of identifying a subject with a defect in a DNA repair pathway gene for treatment of a gastrointestinal (GI) malignancy with a Poly (ADP-ribose) polymerase (PARP) inhibitor, comprising obtaining a biological sample from the subject; subjecting the sample to an assay adapted to determine a DNA repair pathway gene defect; and identifying the subject as a subject for treatment with the PARP inhibitor based on the presence of a DNA repair pathway gene defect.

Various embodiments of the present invention provide for a process of identifying a defect in a DNA repair pathway gene in a subject, comprising: obtaining a biological sample from a subject who desires determination regarding treatment of a gastrointestinal (GI) malignancy with a Poly (ADP-ribose) polymerase WARP) inhibitor; assaying the biological sample to determine the presence or absence of a DNA repair pathway gene defect; and determining the presence or absence of the DNA repair pathway gene defect.

Various embodiments of the present invention also provide for a method, comprising: assessing a biological sample obtained from a subject with a gastrointestinal (GI) malignancy who desires determination regarding treatment with a Poly (ADP-ribose) polymerase WARP) inhibitor to determine the presence or absence of a DNA repair pathway gene defect.

In various embodiments, the DNA repair pathway is nucleotide excision repair pathway, fanconi anemia pathway, DNA replication pathway, base excision repair pathway, or a combination thereof. In various embodiments, the DNA repair pathway is the nucleotide excision repair pathway. In various embodiments, the DNA repair pathway is the fanconi anemia pathway. In various embodiments, the DNA repair pathway is the DNA replication pathway. In various embodiments, the DNA repair pathway is the base excision repair pathway.

In various embodiments, the DNA repair pathways defect are two or more defects in: nucleotide excision repair pathway, fanconi anemia pathway, DNA replication pathway, and base excision repair pathway. In various embodiments, the DNA repair pathway defects are three or more defects in: nucleotide excision repair pathway, fanconi anemia pathway, DNA replication pathway, and base excision repair pathway. In various embodiments, the DNA repair pathway defects are defects in nucleotide excision repair pathway, fanconi anemia pathway, DNA replication pathway, and base excision repair pathway.

In various other embodiments, the DNA repair pathway gene in the nucleotide excision repair pathway is RFC2, ERCC1, XPA, CUL4A, or a combination thereof; the fanconi anemia pathway is ERCC1, FANCE, or both; the DNA replication pathway is RFC2, MCM4, or both; and the base excision repair pathway is NEIL1, PARP3, APEX2, or a combination thereof.

In various other embodiments, the DNA repair pathway genes are 1, 2, 3, 4, 5, 6, 7, 8, 9, 10, 11, 12, 13, 14, 15, 16, or all of RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, or MLH1.

In various embodiments, the GI malignancy is pancreatic cancer. In various other embodiments, the pancreatic cancer is locally advanced pancreatic cancer. In other embodiments, the pancreatic cancer is borderline resectable pancreatic cancer. In other embodiments, the pancreatic cancer is unresectable pancreatic cancer. In other embodiments, the pancreatic cancer is metastatic pancreatic cancer.

Methods of Treating/Selecting a Therapy

Various embodiments of the present invention also provide for a method of treating a gastrointestinal (GI) malignancy, comprising administering a therapeutically effective amount of a Poly (ADP-ribose) polymerase TARP) inhibitor to a subject determined to have a defect in a DNA repair pathway gene to treat the gastrointestinal (GI) malignancy.

Various embodiments of the present invention also provide for a method of treating a gastrointestinal (GI) malignancy, comprising providing a composition comprising a Poly (ADP-ribose) polymerase PARP) inhibitor; and administering a therapeutically effective amount of the composition to a subject determined to have a defect in a DNA repair pathway gene to treat the gastrointestinal (GI) malignancy.

In various embodiments, the PARP inhibitor is veliparib, talozoparib, olaparib, or niraparib. In some embodiments, the PARP inhibitor is a combination of 1, 2, 3 or all of: veliparib, talozoparib, olaparib, and niraparib. In some embodiments, the PARP inhibitor is veliparib. In some embodiments, the PARP inhibitor is talozoparib. In some embodiments, the PARP inhibitor is olaparib. In some embodiments, the PARP inhibitor is niraparib.

In various embodiments, the GI malignancy is pancreatic cancer. In other embodiments, the pancreatic cancer is locally advanced pancreatic cancer. In other embodiments, the pancreatic cancer is borderline resectable pancreatic cancer. In other embodiments, the pancreatic cancer is unresectable pancreatic cancer. In other embodiments, the pancreatic cancer is metastatic pancreatic cancer.

In various embodiments, the DNA repair pathway gene defect is a defect in 1, 2, 3, 4, 5, 6, 7, 8, 9, 10, 11, 12, 13, 14, 15, 16 or all of RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, and MLH1. In various embodiments, the DNA repair pathway defect is a defect in 1, 2, 3 or all of: nucleotide excision repair pathway, fanconi anemia pathway, DNA replication pathway, base excision repair pathway. In various embodiments, the DNA repair pathway is the nucleotide excision repair pathway. In various embodiments, the DNA repair pathway is the fanconi anemia pathway. In various embodiments, the DNA repair pathway is the DNA replication pathway. In various embodiments, the DNA repair pathway is the base excision repair pathway.

In yet other embodiments, the method further comprises treating the subject with radiation and/or chemotherapy.

Various embodiments of the present invention also provide for a method of selecting a therapy for a subject with a gastrointestinal (GI) malignancy, comprising obtaining a biological sample from the subject; subjecting the sample to an assay adapted to determine a DNA repair pathway gene defect; identifying the subject as in need of treatment based on the presence of a DNA repair pathway gene defect; and selecting a Poly (ADP-ribose) polymerase (PARP) inhibitor as the therapy for the subject identified. In various embodiments, the PARP inhibitor is veliparib, talozoparib, olaparib, or niraparib. In various embodiments, the PARP inhibitor is veliparib. In various embodiments, the PARP inhibitor is talozoparib. In various embodiments, the PARP inhibitor is olaparib. In various embodiments, the PARP inhibitor is niraparib.

In various embodiments, the GI malignancy is pancreatic cancer. In various other embodiments, the pancreatic cancer is locally advanced pancreatic cancer. In other embodiments, the pancreatic cancer is borderline resectable pancreatic cancer. In other embodiments, the pancreatic cancer is unresectable pancreatic cancer. In other embodiments, the pancreatic cancer is metastatic pancreatic cancer.

In various embodiments, the DNA repair pathway gene defect is a defect in 1, 2, 3, 4, 5, 6, 7, 8, 9, 10, 11, 12, 13, 14, 15, 16 or all of: RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, and MLH1. In various embodiments, the DNA repair pathway defect is a defect in 1, 2, 3, or all: nucleotide excision repair pathway, fanconi anemia pathway, DNA replication pathway, base excision repair pathway. In various embodiments, the DNA repair pathway is the nucleotide excision repair pathway. In various embodiments, the DNA repair pathway is the fanconi anemia pathway. In various embodiments, the DNA repair pathway is the DNA replication pathway. In various embodiments, the DNA repair pathway is the base excision repair pathway.

In various embodiments, the PARP inhibitor is 1, 2, 3 or all of: veliparib, talozoparib, olaparib, and niraparib. In various embodiments, the PARP inhibitor is veliparib. In various embodiments, the PARP inhibitor is talozoparib. In various embodiments, the PARP inhibitor is olaparib. In various embodiments, the PARP inhibitor is niraparib.

In various embodiments, the treatment comprises administering the PARP inhibitor in conjunction with radiation, chemotherapy or a combination thereof.

Various embodiments of the present invention provide for a method of treating a gastrointestinal (GI) malignancy, comprising: administering a therapeutically effective amount of a composition comprising a Poly (ADP-ribose) polymerase (PARP) inhibitor to a subject; administering a therapeutically effective amount of radiation therapy; and administering a therapeutically effective amount of chemotherapy.

In various embodiments, the subject is determined to have a defect in a DNA repair pathway gene to treat the gastrointestinal (GI) malignancy.

In various embodiments, the PARP inhibitor is talozoparib, olaparib, and/or niraparib.

In various embodiments, the GI malignancy is pancreatic cancer. In various embodiments, the pancreatic cancer is locally advanced pancreatic cancer. In other embodiments, the pancreatic cancer is borderline resectable pancreatic cancer. In other embodiments, the pancreatic cancer is unresectable pancreatic cancer. In other embodiments, the pancreatic cancer is metastatic pancreatic cancer.

In various embodiments, the DNA repair pathway gene is RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, MLH1, or a combination thereof.

In various embodiments, the PARP inhibitor is olaparib, the radiation therapy is intensity-modulated radiation therapy (IMRT), and the chemotherapy is gemcitabine.

In various embodiments, PARP inhibitor is olaparib and is administered 25 mg twice per day, the radiation therapy is intensity-modulated radiation therapy (IMRT) and is administered at a dose of 36Gy in 15 fractions with 5 fractions per week, and the chemotherapy is gemcitabine and is administered 600 mg/m$^2$ once per week for 3 weeks.

In various embodiments, PARP inhibitor is olaparib and is administered 25 mg twice per day, the radiation therapy is intensity-modulated radiation therapy (IMRT) and is administered at a dose of 36Gy in 15 fractions with 5 fractions per week, and the chemotherapy is gemcitabine and is administered 400 mg/m$^2$ or 250 mg/m$^2$ once per week for 3 weeks, or chemotherapy is not administered.

In various embodiments, PARP inhibitor is olaparib and is administered 50 mg or 100 mg twice per day, the radiation therapy is intensity-modulated radiation therapy (IMRT) and is administered at a dose of 36Gy in 15 fractions with 5 fractions per week, and the chemotherapy is gemcitabine and is administered 600 mg/m$^2$ once per week for 3 weeks.

Additional examples of doses, dosage timing and treatment regimens are discussed below.

Various embodiments of the present invention provide for the administration of a therapy to a subject, as part of a treatment strategy that aids in the treatment of GI malignancies. In some embodiments, the therapy administered is a PARP inhibitor, radiation therapy, chemotherapy or a combination thereof. In some embodiments, the therapy administered is a PARP inhibitor. In some embodiments, the therapy administered is a radiation therapy. In some embodiments, the therapy administered is a chemotherapy. In various embodiments, the therapy administered is a PARP inhibitor and radiation therapy. In some embodiments, the therapy administered is a PARP inhibitor and chemotherapy. In yet other embodiments, the therapy administered is a radiation therapy and a chemotherapy.

Examples of PARP inhibitors include, but are not limited to, Iniparib, Talazoparib, Veliparib, Olaparib, Olaparib TOPARP-A, Rucaparib, niraparib, CEP 9722, Eisai's E7016, BGB-290, and 3-aminobenzamide. In various embodiments, the PARP inhibitor is veliparib, talozoparib, olaparib, and/or niraparib. In some embodiments, the PARP inhibitor is a combination of one or more of veliparib, talozoparib, olaparib, or niraparib. In some embodiments, the PARP inhibitor is veliparib. In some embodiments, the PARP inhibitor is talozoparib. In some embodiments, the PARP inhibitor is olaparib. In some embodiments, the PARP inhibitor is niraparib.

Radiation therapy may be delivered externally (external-beam radiation therapy) or internally (internal radiation therapy) by placing radioactive material in the body near the cancer cells. This can be accomplished, for example, by injection or through oral administration of the radioactive substance.

Examples of radiation therapy include, but are not limited to, systemic radiation therapy, conformal radiotherapy, intensity modulated radiotherapy (IMRT), image guided radiotherapy (IGRT), 4-dimensional radiotherapy (4D-RT), stereotactic radiotherapy and radiosurgery, proton therapy, electron beam radiotherapy and adaptive radiotherapy. In various embodiments, the radiation therapy is intensity modulated radiotherapy (IMRT).

Examples of a chemotherapeutic include, but are not limited to, Bevacizumab, Carmustine, Carmustine, Lomustine, Everolimus, Temozolomide, Taxotere, pemetrexed, Cabazitaxel, Estramustine, Docetaxel, Paclitaxel, Platinum agents (cisplatin, carboplatin), Vinorelbine, Capecitabine, Liposomal doxorubicin, Gemcitabine, Mitoxantrone, cyclophosphamide, Doxorubicin, and Vincristine. In various embodiments, the chemotherapeutic is gemcitabine.

In certain embodiments, the disease treated is cancer. The cancer may be newly diagnosed, recurrent or non-recurrent. In other embodiments, the cancer is pancreatic cancer. In some embodiments, the cancer is locally advanced pancreatic cancer. In other embodiments, the pancreatic cancer is borderline resectable pancreatic cancer. In other embodiments, the pancreatic cancer is unresectable pancreatic cancer. In other embodiments, the pancreatic cancer is metastatic pancreatic cancer.

Modes of Administration and Carriers/Excipients

In various embodiments, the therapy may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

In various embodiments, the therapy can be administered intravenously by injection or by gradual infusion over time. Given an appropriate formulation for a given route, for example, the therapy can be administered intravenously, intranasally, by inhalation, intraperitoneally, intramuscularly, subcutaneously, intracavity, and can be delivered by peristaltic means, if desired, or by other means known by those skilled in the art. It is preferred that the therapy is administered orally, intravenously or intramuscularly to a patient having cancer, in particular breast cancer.

The therapy according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, the present invention provides a therapy which includes a pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The therapy as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent used in the invention that will be effective in the treatment of a particular disorder or condition will depend on the nature of the disorder or condition, and can be determined by one of skill in the art with standard clinical techniques.

The therapy according to the invention may be delivered in a therapeutically effective amount. The precise therapeutically effective amount is that amount of the composition/treatment that will yield the most effective results in terms of efficacy of treatment in a given subject. This amount will vary depending upon a variety of factors, including but not limited to the characteristics of the therapy/therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. For additional guidance, see *Remington: The Science and Practice of Pharmacy* (Gennaro ed. 20th edition, Williams & Wilkins Pa., USA) (2000).

For the treatment of the disease, the appropriate dosage of the therapy depends on the type of disease to be treated, the severity and course of the disease, the responsiveness of the disease, whether the therapy is administered for therapeutic or preventative purposes, previous treatment, and the patient's clinical history. The dosage can also be adjusted by the individual physician in the event of any complication and at the discretion of the treating physician.

The duration of therapy can be continued for as long as medically indicated or until a desired therapeutic effect (e.g., diminished, absence or remission of the cancer) is achieved. In certain embodiments, the therapy is continued for 1 month, 2 months, 4 months, 6 months, 8 months, 10 months, 1 year, 2 years, 3 years, 4 years, 5 years, or for a period of years up to the lifetime of the subject. The duration of treatment and type of treatment depends upon the subject's clinical progress, responsiveness to therapy and analysis of the evolved tumors genetic profile. In some embodiments, dosage is from 0.01 µg to 0.1 µg per kg of body weight, 0.01 µg to 1 µg per kg of body weight, 0.01 µg to 10 µg per kg of body weight, 0.01 µg to 100 µg per kg of body weight, 0.1 µg to 1 µg per kg of body weight, 0.1 µg to 10 µg per kg of body weight, 0.1 µg to 100 µg per kg of body weight, 1 µg to 10 µg per kg of body weight, 1 µg to 100 µg per kg of body weight, 10 µg to 100 µg per kg of body weight, 10 µg to 25 µg per kg of body weight, 25 µg to 50 µg per kg of body weight, 50 µg to 75 µg per kg of body weight or 75 µg to 100 µg per kg of body weight. In some embodiments, dosage is 0.01 µg per kg of body weight, 0.1 µg per kg of body weight, 1 µg per kg of body weight, 10 µg per kg of body weight, 25 µg per kg of body weight, 50 µg per kg of body weight, 75 µg per kg of body weight, or 100 µg per kg of body weight.

In some embodiments, dosage is from 0.1 mg to 1 mg per kg of body weight, 0.1 mg to 10 mg per kg of body weight, 0.1 mg to 100 mg per kg of body weight, 1 mg to 10 mg per kg of body weight, 1 mg to 100 mg per kg of body weight, 10 mg to 100 mg per kg of body weight, 10 mg to 25 mg per kg of body weight, 25 mg to 50 mg per kg of body weight, 50 mg to 75 mg per kg of body weight or 75 mg to 100 mg per kg of body weight. In some embodiments, dosage is 1 mg per kg of body weight, 10 mg per kg of body weight, 25 mg per kg of body weight, 50 mg per kg of body weight, 75 mg per kg of body weight, or 100 mg per kg of body weight.

In some embodiments, the dosage is 0.01 µg, 0.1 µg, 1 µg, 10 µg, 25 µg, 50 µg, 75 µg, 100 µg, 200 µg, 250 µg, 300 µg, 500 µg, 750 µg, 1 mg, 10 mg, 25 mg, 50 mg, 75 mg, 100 mg, 200 mg, 250 mg, 300 mg, 500 mg, 750 mg, 1000 mg, 2000 mg, 3000 mg, 4000 mg or 5000 mg.

In various other embodiments, radiation therapy is administered in a dose of 1-120 GY. In some embodiments, the dosage administered is 1-20 GY, 20-40 GY, 40-60 GY, 60-80 GY, 80-100 GY or 100-120 GY. In some embodiments, the dosage administered is 1 GY, 2 GY, 3 GY, 4 GY, 5 GY, 6 GY, 7 GY, 8 GY, 9 GY, 10 GY, 11 GY, 12 GY, 13 GY, 14 GY, 15 GY, 20 GY, 25 GY, 30 GY, 35 GY, 40 GY, 45 GY, 50 GY, 55 GY, 60 GY, 65 GY, 70 GY, 75 GY, 80 GY, 85 GY, 90 GY, 95 GY, 100 GY, 105 GY, 110 GY, 115 GY, or 120 GY. The dosages can be given in 1, 2, 3, 4, 5, 6, 7, 8, 9, 10, 11, 12, 13, 14, 15, 16, 17, 18, 19, 20, 25, or 30 fractions (fx). In various embodiments, the dose of radiation therapy comprises 36 GY/15fx.

In various embodiments, the chemotherapeutic is administered in a dose of 1-1000 mg/m$^2$. In some embodiments, the dosage administered is 1-10 mg/m$^2$, 10-20 mg/m$_2$, 20-30 mg/m$^2$, 30-40 mg/m$^2$, 40-50 mg/m$^2$, 50-75 mg/m$^2$, 75-100 mg/m$^2$, 100-200 mg/m$^2$, 200-300 mg/m$^2$, 300-400 mg/m$^2$, 400-500 mg/m$^2$, 500-600 mg/m$^2$, 600-700 mg/m$^2$, 700-800 mg/m$^2$, 800-900 mg/m$^2$ or 900-1000 mg/m$^2$, 1000-1250 mg/m$^2$, 1250-1500 mg/m$^2$, 1500-1750 mg/m$^2$, 1750-2000 mg/m$^2$. In various embodiments, the chemotherapeutic is administered in a dose of 1 mg/m$^2$, 5 mg/m$^2$, 10 mg/m$^2$, 15 mg/m$^2$, 20 mg/m$^2$, 25 mg/m$^2$, 50 mg/m$^2$, 60 mg/m$^2$, 75 mg/m$^2$, 100 mg/m$^2$, 150 mg/m$^2$, 200 mg/m$^2$, 250 mg/m$^2$, 300 mg/m$^2$, 400 mg/m$^2$, 500 mg/m$^2$, 600 mg/m$^2$, 750 mg/m$^2$, 1000 mg/m$^2$, 1250 mg/m$^2$, 1500 mg/m$^2$, 1750 mg/m$^2$, or 2000 mg/m$^2$, In various embodiments, the PARP inhibitor is administered in a dose of 1-100 mg. In some embodiments, the dosage administered is 1-10 mg, 10-20 mg, 20-30 mg, 30-40 mg, 40-50 mg, 50-60 mg, 60-70 mg, 70-80 mg, 80-90 mg, 90-100 mg. In various embodiments the PARP inhibitor is administered in a dose of 1 mg, 5 mg, 10 mg, 15 mg, 20 mg, 25 mg, 50 mg, 75 mg, or 100 mg. In various embodiments the PARP inhibitor is administered in a dose of 40 mg. In various embodiments the PARP inhibitor is administered in a dose of 25 mg.

In various embodiments, the dosage of each therapy (e.g., PARP inhibitor, chemotherapy, radiation therapy) can be given 1, 2, 3, 4, 5 or more times daily, every 2 days, every 5 days, weekly, every two weeks, every three weeks, every 4 weeks, monthly, every two months, every three months, every four months, every 5 months, every 6 months, every 7 months, every 8 months, every, 9 months, every 10 months, every 11 months, yearly, every 2, 3, 4, 5, or 10 years.

In various embodiments, the different therapeutic modalities can be given at a different intervals and dosages. For example, a combination treatment cycle of 3 weeks is gemcitabine given at 600 mg/m$^2$ once a week for three weeks, IMRT at 36 Gy/15 fractions, 5 fractions per week, and olaparib at 25 mg BID for 21 days.

Biological Samples, Sample Preparation and DNA Repair Pathway Gene Defect Detection In various embodiments, the steps involved in the current invention comprise obtaining a biological sample from a subject. The biological sample may be obtained either through surgical biopsy or surgical resection. Alternatively, a sample can be obtained through primary patient derived cell lines, or archived patient samples in the form of FFPE (Formalin fixed, paraffin embedded) samples, or fresh frozen samples. A sample may also comprise blood, plasma, peripheral mononuclear cells, cells, or other bodily fluid or tissue. In various embodiments, the sample comprises tissue from the gastrointestinal tract. In some embodiments, the sample comprises tissue from the large and/or small intestine. In various other embodiments, the large intestine sample comprises the cecum, colon (the ascending colon, the transverse colon, the descending colon, and the sigmoid colon), rectum and/or the anal canal. In yet other embodiments, the small intestine sample comprises the duodenum, jejunum, and/or the ileum.

Nucleic acid or protein samples derived from the biological sample (i.e., tissue and/or cells such as peripheral blood mononuclear cells) of a subject that can be used in the methods of the invention can be prepared by means well known in the art. For example, surgical procedures or needle biopsy aspiration can be used to collect the biological samples from a subject. In some embodiments, it is important to enrich and/or purify the abnormal tissue and/or cell samples from the normal tissue and/or cell samples. In other embodiments, the abnormal tissue and/or cell samples can then be microdissected to reduce the amount of normal tissue contamination prior to extraction of genomic nucleic acid or pre-RNA for use in the methods of the invention. Such enrichment and/or purification can be accomplished according to methods well-known in the art, such as needle microdissection, laser microdissection, fluorescence activated cell sorting, and immunological cell sorting.

Analysis of the nucleic acid and/or protein from an individual may be performed using any of various techniques. In various embodiments, assaying for DNA Repair Pathway gene defects comprises northern blot, reverse transcription PCR, real-time PCR, serial analysis of gene expression (SAGE), DNA microarray, tiling array, RNA-Seq, or a combination thereof. In various embodiments, the DNA defects are identified in blood or tumor tissue using DNA or RNA sequencing.

In various embodiments, methods and systems to detect protein include but are not limited to ELISA, immunohistochemistry, western blot, flow cytometry, fluorescence in situ hybridization (FISH), radioimmuno assays, and affinity purification.

DNA Repair Pathway genes include, but are not limited to, RFC2, ERCC1, XPA, CUL4A, ERCC1, FANCE, RFC2, MCM4, NEIL1, PARP3, APEX2, ARID1A, ATM-x, CHEK2-D293fs*1, PALB2-V836I, PTEN, and MLH1. In various other embodiments, the gene expression levels for 1, 2, 3, 4, 5, 6, 7, 8, 9, 10, 11, 12, 13, 14, 15, 16, or 17 genes are assayed. In some embodiments, the sample is assayed for DNA Repair Pathway gene expression levels.

The analysis of a DNA repair pathway gene defect may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods and Applications, Academic Press Inc., San Diego, Calif. It will be apparent to one skilled in the art that controlled robotic systems are useful for isolating and amplifying nucleic acids and can be used.

Hybridization

The nucleic acid samples derived from a subject used in the methods of the invention can be hybridized to arrays comprising probes (e.g., oligonucleotide probes) in order to identify the DNA Repair Pathway genes, described above, and in instances wherein a housekeeping gene expression is also to be assessed, comprising probes in order to identify selected housekeeping genes. In particular embodiments, the probes used in the methods of the invention comprise an array of probes that can be tiled on a DNA chip (e.g., SNP oligonucleotide probes). Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays. The single-stranded synthetic oligodeoxyribonucleic acid DNA probes of an array may need to be denatured prior to contact with the nucleic acid samples from a subject, e.g., to remove hairpins or dimers which form due to self-complementary sequences.

Optimal hybridization conditions will depend on the length of the probes and type of nucleic acid samples from a subject. General parameters for specific (i.e., stringent) hybridization conditions for nucleic acids are described in Sambrook and Russel, *Molecular Cloning: A Laboratory Manual* 4$^{th}$ ed., Cold Spring Harbor Laboratory Press (Cold Spring Harbor, N.Y. 2012); Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization with Nucleic Acid Probes, Elsevier Science Publishers B. V. and Kricka, 1992, Nonisotopic DNA Probe Techniques, Academic Press, San Diego, Calif.

Allele Specific Oligonucleotide Nucleic Acid Arrays

In some embodiments of the methods of the present invention, DNA arrays can be used to determine the DNA Repair Pathway Gene defects, by measuring the level of hybridization of the nucleic acid sequence to oligonucleotide probes that comprise complementary sequences. Various formats of DNA arrays that employ oligonucleotide "probes," (i.e., nucleic acid molecules having defined sequences) are well known to those of skill in the art. Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

In some embodiments, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes. Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. DNA array technologies have made it possible to determine mutations and/or the expression level of the DNA Repair Pathway genes, described above, and housekeeping genes.

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof. The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

A heteroduplex mobility assay (HMA) is another well-known assay that may be used to detect a DNA Repair Pathway gene defect. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a DNA Repair Pathway gene defect. This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a DNA Repair Pathway gene defect. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a DNA Repair Pathway gene defect are known in the art and useful in the methods of the invention. Other well-known approaches for determining the presence or absence of a DNA Repair Pathway gene defect include automated sequencing and RNAase mismatch techniques (Winter et al., Proc. Natl. Acad. Sci. 82:7575-7579 (1985)).

Labeling

In some embodiments, the protein, polypeptide, nucleic acid, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, 32P and 14C. Fluorescent molecules suitable for the present invention include, but are not limited to, fluorescein and its derivatives, rhodamine and its derivatives, texas red, 5' carboxy-fluorescein ("FAM"), 2', 7'-dimethoxy-4', 5'-dichloro-6-carboxy-fluorescein ("JOE"), N, N, N', N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CYS, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

Kits

The present invention is also directed to a kit for the identification, therapy selection and/or treatment of a subject with a gastrointestinal malignancy. The kit is useful for practicing the inventive method of identifying a subject with a GI malignancy and a defect in the DNA repair pathway for treatment, selecting a therapy for a subject having a GI malignancy and a defect in the DNA repair pathway and treating the subject with a GI malignancy and a defect in the DNA repair pathway. The kit is an assemblage of materials or components, including at least one of the inventive compositions. Thus, in some embodiments the kit contains a composition including primers and probes for DNA Repair Pathway genes, as described above.

The exact nature of the components configured in the inventive kit depends on its intended purpose. For example, some embodiments are configured for the purpose of assessing the presence or absence of DNA Repair Pathway gene defects. In other embodiments, the gene expression levels of DNA Repair Pathway gene defects are assessed. In one embodiment, the kit is configured particularly for the purpose of assessing mammalian subjects. In another embodiment, the kit is configured particularly for the purpose of assessing human subjects. In further embodiments, the kit is configured for veterinary applications, assessing subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to identify, select a therapy and/or treat a subject with a GI malignancy and a defect in the DNA repair pathway using the DNA Repair Pathway genes, described above. Optionally, the kit also contains other useful components, such as, primers, diluents, buffers, pipetting or measuring tools or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in gene expression assays. The packaging materials employed in the kit may also be those customarily utilized in treatment of a subject. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing primers and probes for the DNA repair pathway genes described above. The packaging material generally has an external label which indicates the contents and/or purpose of the kit and/or its components.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1

Treatment naïve patients with LA or borderline resectable pancreatic cancer (BR) were treated with weekly gemcitabine (1000 mg/m$^2$), daily intensity modulated RT (36 Gy/15 fractions) and veliparib 20 mg BID daily for 3 weeks escalated according to a novel Bayesian method followed by standard chemotherapy. RNA-seq libraries were prepared from pre-treatment tumor biopsies. The database for annotation, visualization, and integrated discovery (DAVID) v6.7 was used to interpret the differential expression genes data. Cox regression model was used to identify DNA damage related pathways associated with patient survivals.

Thirty-four patients were enrolled from September 2013 to May 2016. Four were removed due to non-compliance. Four (13.3%) and 26 (86.7%) patients had BR and LA, respectively. The maximum tolerated dose of veliparib was 40 mg BID in combination with gemcitabine dose reduced to 400 mg/m$^2$. Twelve patients experienced dose limiting toxicities (83.3% lymphopenia, 8.3% neutropenia, febrile neutropenia, abdominal infection, abdominal pain, hyponatremia, and leukopenia.) The most frequent grade>/=3 AEs were lymphocyte count decreased, hyperglycemia, and anemia. Median PFS and OS for the entire cohort were 9.8 months (95% CI: 8.4-18.6) and 14.6 months (95% CI: 11.6-21.8), respectively. RNA seq analysis of differentially expressed genes identified 50% of patients harboring DNA repair defects. Median OS was significantly higher for these biomarker positive (+) compared to negative (−) patients in 3 DNA damage related pathways: Nucleotide Excision Repair (22 vs. 12 mos, p<0.001), Mismatch Repair (18 vs. 12 mos, p<0.05) and Fanconi Anemia (18 vs. 12 mos, p<0.01). The combination of veliparib, gemcitabine and IMRT was well tolerated in patients with LA and BR pancreatic cancer. DNA repair defects were identified in 50% of patients and median OS was significantly longer in this sub set.

TABLE 1

Progression free survival following VelGemRad treatment.

| PFS | # of Patients | Events | Median (Month) |
|---|---|---|---|
| | logrank pvalue = 0.6294 (not significant) | | |
| Negative Biomarker Group | 15 | 10 | 11 |

TABLE 1-continued

Progression free survival following VelGemRad treatment.

| PFS | # of Patients | Events | Median (Month) |
|---|---|---|---|
| Positive Biomarker Group | 5 | 3 | 19 |
| DNA Replication Pathway logrank pvalue = 0.00077 | | | |
| est. < median | 16 | 7 | 22 |
| est. >= median | 16 | 14 | 9 |
| Base Excision Repair Pathway logrank pvalue = 0.00075 | | | |
| est. < median | 16 | 8 | 22 |
| est. >= median | 16 | 13 | 9 |
| Nucleotide Excision Repair Pathway logrank pvalue = 0.00363 | | | |
| est. < median | 16 | 9 | 21 |
| est. >= median | 16 | 12 | 9 |
| Mismatch Repair Pathway logrank pvalue = 0.0743 (not significant) | | | |
| est. < median | 16 | 10 | 21 |
| est. >= median | 16 | 11 | 9 |
| Fanconi Anemia Pathway logrank pvalue = 0.00385 | | | |
| est. < median | 16 | 7 | 21 |
| est. >= median | 16 | 14 | 9 |

TABLE 2

Overall survival following VelGemRad treatment

| | OS # of Patients | Events | Median (Month) |
|---|---|---|---|
| logrank pvalue = 0.5117 (not significant) | | | |
| Negative Biomarker Group | 15 | 12 | 17 |
| Positive Biomarker Group | 5 | 4 | 15 |
| DNA Replication Pathway logrank pvalue = 0.06718 (not significant) | | | |
| est. < median | 16 | 14 | 17.5 |
| est. >= median | 17 | 14 | 12 |
| Base Excision Repair Pathway logrank pvalue = 048236 (not significant) | | | |
| est. < median | 16 | 12 | 14 |
| est. >= median | 17 | 16 | 12 |
| Nucleotide Excision Repair Pathway logrank pvalue = 0.00029 | | | |
| est. < median | 16 | 12 | 22 |
| est. >= median | 17 | 16 | 12 |
| Mismatch Repair Pathway logrank pvalue = 0.04313 | | | |
| est. < median | 16 | 13 | 18 |
| est. >= median | 17 | 15 | 12 |
| Fanconi Anemia Pathway logrank pvalue = 0.01386 | | | |
| est. < median | 16 | 14 | 18 |
| est. >= median | 17 | 14 | 12 |

Example 2

Nonclinical Activity

In vitro, veliparib inhibited PARP-1 and PARP-2 with Ki values of 3.6 nM and 2.9 nM, respectively. These values were observed in enzyme assays measuring the incorporation of [3H]-NAD+ into histone H1, an important physiological substrate of PARP. In assays measuring inhibition of H2O2-induced poly(ADP-ribosyl)ation in C-41 cervical carcinoma cells, veliparib inhibited PARP with an EC50 value of 2.4 nM. The extent of DNA damage in cells was indicated by γ-H2AX levels. To determine the effect of veliparib in combination with cytotoxic agents on DNA damage, the cellular content of γ-H2AX in C-41 cells was assayed by flow cytometry using an anti-γ-H2AX antibody. Addition of 1 mM of temozolomide alone resulted in increased numbers of γ-H2AX foci, a result which was further potentiated by veliparib in a dose-dependent manner. When cell survival was measured by an AlamarBlue assay, veliparib potentiated cytotoxicity in the same concentration range as used in the γ-H2AX assay, demonstrating that veliparib potentiates cytotoxicity of temozolomide by delaying DNA repair. Veliparib achieved a maximal potentiation of approximately 15-fold. Veliparib also potentiates the DNA damage cause by irinotecan.

The combination of PARP inhibitors with different classes of chemotherapeutics was examined. Cisplatin-induced potentiation was observed in a long-term clonogenic assay, but not in the short-term cytotoxicity assay. The potentiation of cisplatin by veliparib in vitro is consistent with the potent enhancement of the efficacy of platinum agents (cisplatin and carboplatin) observed in vivo. PARP inhibition was shown to sensitize cells that are mismatch repair (MMR)-deficient to a greater extent than cells that are MMR competent. Alkylating agents such as temozolomide form methyl adducts in DNA and resistance is frequently encountered in the clinic with either the overexpression of 06-alkylguanine DNA alkyltransferase (AGT) or functional defects in the MMR system. However, when PARP was inhibited, cells were sensitized to methylpurine formation, regardless of their resistance factors.

Without being bound to any particular theory, studies show that PARP inhibitors have activity against some BRCA deficient cells in the absence of any DNA damaging agent. These inhibitors did not demonstrate single agent activity in BRCA-competent cells, and restoring functional BRCA to deficient cells abrogated single agent cytotoxicity. It is possible that, in BRCA-deficient cells, PARP inhibition stops the BER pathway, and thus single-stranded breaks are carried through DNA synthesis, resulting in doublestranded breaks. The increase in double-stranded breaks cannot be repaired by homologous recombination (HR), due to the lack of BRCA1 or 2, resulting in increased cell death. However, since not all BRCA deficient cells are sensitive to the PARP inhibitors, it is unclear why single agent cytotoxicity is observed in some BRCA-deficient cells.

Consistent with PARP-1 being a radiosensitization target, PARP-1 knockout mice showed enhanced sensitivity to γ-radiation. There is evidence to suggest that PARP inhibitors sensitize cancer cells to radiation, both in vitro and in vivo. Furthermore, a PARP inhibitor in the same class as veliparib potentiated radiation in the HCT116 colon carcinoma model. Veliparib was tested, in combination with cytotoxic agents, in several tumor models and demonstrated a similar profile of antitumor activity to that seen in the literature (See table below). Veliparib substantially increased the efficacy of cytotoxic therapies, when measured by either treated/control tumor volumes (% T/C) or by increased time for tumors to grow to a particular size (% ILS).

TABLE 3

Preclinical Data for veliparib mediated potentiation of cytotoxic agents

| | Breast carcinoma (human MX-1) | Glioblastoma multiforme (rat 9L) | B Cell lymphoma (human DOHH2) | Melanoma (murine B16F10) |
|---|---|---|---|---|
| Carboplatin | Yes | | | |
| Cisplatin | Yes | | No | |
| Cyclophosphamide | Yes | | | |
| Irinotecan | | | | Yes |
| Temozolomide | | Yes | | Yes |

Veliparib potentiated cytotoxic therapy when administered either parenterally or orally (PO). When administered parenterally, significant efficacy was observed at doses as low as 1 mg/kg/day, and maximal efficacy was achieved at approximately 12.5 mg/kg/day. 3.1 mg/kg/day PO (divided, twice daily) provided significant potentiation, with maximal potentiation achieved at approximately 25 mg/kg/day. No increased toxicity was observed at any of these veliparib doses, either parenteral or PO. Supratherapeutic doses of veliparib (50 mg/kg/day), administered via osmotic minipump (OMP), resulted in skin toxicity at the pump implantation site. The observation that supratherapeutic doses of PARP inhibitors may potentiate toxicity is consistent with preclinical and clinical observations. It is also consistent with the results from a two-week veliparib/cisplatin combination study. When administered as a continuous infusion, an veliparib Css (plasma concentration at steady-state) of 70 ng/mL was maximally efficacious (area under the curve [AUC]=1.7 µg·hr/mL). Comparable efficacy was seen in oral studies at a 25 mg/kg/day (divided, twice daily) dose that yielded AUCs between 1.6 and 3.0 µg·hr/mL. At this dose, the plasma concentrations were above 70 ng/mL for only 2-4 hours per dose, demonstrating that 24 hour/day coverage above 70 ng/mL was not required for efficacy.

An enzyme-linked immunosorbent assay (ELISA) that can measure PAR formation was used to demonstrate PARP inhibition in murine tumors in vivo and human peripheral blood mononuclear cells (PBMCs) ex vivo at clinically relevant doses. This ELISA was used as the primary assay for PARP biomarker analysis. The degree of PARP inhibition was assessed in B16F10 syngeneic flank tumors from mice treated in vivo using tumor efficacy schedules. In this study, PAR formation was measured in tumors treated with veliparib alone. Two hours after administration, veliparib inhibited PAR formation in B16F10 tumors in a dose-dependent manner.

The same response was reflected in a parallel efficacy experiment, where temozolomide (50 mg/kg/day, PO, daily× 5) was administered with veliparib. In another study, PAR formation was measured in tumors treated simultaneously with temozolomide and veliparib. As in the veliparib only study, tumor PAR levels in the combination study were also inhibited. Inhibition of PARP activity was significant at 12.5, 5 and 1 mg/kg/day in both the vehicle and temozolomide treated groups. Overall, these results indicate the ability of veliparib to inhibit both baseline and cytotoxic-induced PARP activity in tumors treated in vivo and provide evidence of the ability of veliparib to target PARP in vivo.

Inhibition of PAR was similarly analyzed with ex vivo treatment of human PBMCs from eight healthy volunteers. The cells from one of the eight volunteers showed no detectable PARP activity, while in another patient, PARP activity was not assessable by the assay. In the remaining six individuals, not only were baseline levels of PAR detected, but more importantly, a dose-dependent inhibition of PAR was observed with ex vivo treatment with veliparib. Inhibition occurred at 10 nM (2.4 ng/mL), and PAR formation was almost eliminated at 300 nM (71 ng/mL).

Nonclinical Pharmacology and Toxicology

The pharmacokinetics (PK) of veliparib was evaluated in CD-1 mice, Sprague-Dawley rats, beagle dogs and cynomolgus monkeys. The non-clinical PK profile of veliparib was characterized by high plasma clearance (CL) values, ranging from a high of 4.1 L/hr·kg in the mouse to a low of 0.57 L/hr·kg in the dog. Veliparib exhibits moderate volumes of distribution (Vss) in all species (Vss>2.0 L/kg), with terminal elimination t1/2 in the 1.2-2.7 hr range. In rats and dogs, [3H] veliparib was rapidly absorbed and cleared primarily in the urine as intact parent drug. A-925088 (M8), a lactam derivative and the major product of veliparib metabolism, was also cleared primarily in the urine. In both rats and dogs, parent drug was the major component in systemic circulation, followed by M8. Elimination of total radioactivity was rapid, with most (>80%) of the dose recovered within 24 hours post-dose, indicating that parent drug and the major metabolites are not likely to accumulate. Bioavailability following an oral dose was high (F>50%) in all species, with values ranging from a low of 56.1% in the monkey to a high of 92.0% in the mouse, and low animal-to-animal variability across all species.

The bioavailability from a non-formulated capsule was only slightly lower than from the solution formulation with values of 59.7% and 65.5% in fasted and non-fasted dogs, respectively. This suggests that there are no major food effects. The compound has high solubility at physiological pH and high permeability. Protein binding values in plasma (assessed in vitro as % bound at 5 µM) for veliparib were moderate in all species averaging 42% in dog, 41% in monkey, 43% in mouse, 49% in rat and 51% in human. The stability of veliparib was evaluated in rat, dog, monkey and human plasma and the drug was found to be very stable, with minimal degradation over the 8-hour incubation interval. In vitro metabolism studies indicated that several CYPs (1A1, 1A2, 2C9 and 2C19) have the potential to mediate the formation of M8. However, veliparib is not a potent inhibitor of the major human CYPs in vitro, indicating a low risk for drug-drug interactions at the anticipated therapeutic concentrations. Veliparib partitioned slowly into and out of the brain, in both mouse and rat, with high plasma to brain ratios (~3:1) during the first 3-6 hours after dosing. The plasma to brain ratios approached 1:1 in samples obtained 12 hours after dosing. PK parameters in humans were estimated by a variety of methods. The oral clearance (CL/F) of veliparib was estimated as a function of the projected clearance after IV administration (CL) and the fraction of the dose systemically available after oral administration (F). Clearance predictions were based on allometric scaling. Bioavailability was estimated by simulations with sensitivity analyses using software which took into account human gastrointestinal physiology and the drug's physicochemical characteristics. Vss was estimated either from an average of values observed in animal species, a method averaging the fraction unbound in animal tissues, or by allometric scaling. Terminal phase t1/2 values were estimated either by regression relationships between animal and human t1/2 values (31), or from the estimates of CL and Vss. The human PK profile is projected to have CL=26 L/hr, with oral bioavailability of ~70%. The predicted human t1/2 of veliparib is ~4 hrs. Simulations of 50 mg twice daily dosing in humans mimic a maximally efficacious dosing regimen in mouse (12.5 mg/kg, twice daily), with concentrations above 71 ng/mL for 8 of 24 hours and an AUC24 of 3 μg·hr/mL at steady state. Veliparib was tested in receptor-binding, CNS/neurobehavioral, cardiovascular, cardiac electrophysiological and gastrointestinal assays. In 74 receptor-binding assays at a concentration of 10 μM (2.4 μg/mL), veliparib displaced control-specific binding at the human H1 (61%), the human 5-HT1A (91%), and the human 5-HT7 (84%) sites only, with IC50 values of 1.2-5.3 μM.

Veliparib did not display clear adverse CNS effects in the rat and mouse between 3-30 mg/kg PO. At 100 mg/kg PO, mild sedation-like effects were observed, followed in time by mild excitation. At 300 mg/kg PO, more moderate to marked CNS effects were observed, including abnormal gait and sedation. Further, at 100 mg/kg, PO, there was an increased incidence of death after electrically-induced tonic convulsions in mice. Death was also noted in a second convulsant model (audiogenic seizures in mice). In a repeated dosing mini-Irwin observational test, in which rats were dosed with veliparib at 30, 100, and 300 mg/kg intraperitoneally (IP) every day for 5 days, tonic-clonic seizures/death were observed in approximately 50% of the animals treated at the highest dose on day 1. A similar incidence of seizures was observed after dosing the remaining animals at the same dose on each of the subsequent days. In an acute follow-up study with rats dosed with veliparib 300 mg/kg IP, protection against seizures was not provided by pretreatment with either valproic acid (300 mg/kg IP, 15 min prior to veliparib) or diphenylhydantoin (75 mg/kg IP, 100 min prior to veliparib). In a 2-week toxicology study, seizures were also noted in dogs treated with veliparib at either 60 mg/kg/day, 30 mg/kg twice daily, or 30 mg/kg every day. Plasma concentrations in dogs with seizures were in excess of 5.4 μg/mL (26-fold the predicted clinical Cmax of 0.21 μg/mL). In the anesthetized dog, veliparib produced no physiologically relevant changes in mean arterial pressure, heart rate, dP/dtmax, pulmonary arterial pressure, or systemic or pulmonary vascular resistance compared to vehicle controls at mean plasma concentrations as high as 4.45±0.13 μg/mL (21-fold the predicted clinical Cmax of 0.21 μg/mL). As mean plasma concentrations increased to 12.96±0.92 μg/mL (62-fold), veliparib produced a modest reduction in mean arterial pressure (−16±5% below baseline) and systemic vascular resistance (−10±7% below baseline). Veliparib blocked hERG current with an IC50 value of 57.6±1.7 μg/mL (236±7 μM), a value 278-fold higher than the predicted clinical Cmax. The M8 metabolite of veliparib (A-925088) minimally affected hERG at the highest concentration tested (81.5 μg/mL). While no effect on repolarization (in vitro action potential duration measures) was noted at the lowest measured concentration of veliparib (0.42 μg/mL, 2-fold higher than the predicted clinical Cmax), veliparib prolonged the action potential duration at the intermediate and highest measured concentrations (4.8% and 18.6% prolongation at 4.22±0.02 and 39.49±0.70 μg/mL respectively), suggesting delayed repolarization risk between 20- and 190-times the Cmax. There was a trend (7%) towards delayed repolarization in the anesthetized dog model (QTc intervals) at plasma concentrations 21-fold higher than the predicted clinical Cmax; greater concentrations elicited prolongation (15±3% above baseline [QTcV] at 12.96±0.92 μg/mL). In humans, QTc prolongation is predicted to be less than 3 msec at the anticipated dose of 50 mg twice daily. These cardiac effects need to be monitored during clinical trials.

Gavage administration of veliparib up to 10 mg/kg was generally well tolerated in the ferret emesis model. No emesis was noted at this dose (resulting in mean plasma concentrations of 3.80±0.11 μg/mL, a value 18-fold greater than the predicted Cmax), with significant emesis noted in response to the 20 mg/kg dose (resulting in mean plasma concentrations of 6.61±0.26 μg/mL, a value 31-fold greater than predicted Cmax). Parenteral (subcutaneous) dosing of veliparib at doses and plasma concentrations similar to those used in the gavage study revealed a similar emetic dose-response relationship, suggesting a centrally-mediated emetic response. Veliparib had no significant effect on gastrointestinal transit up to 100 mg/kg (resulting in a mean plasma concentration of 1.63±0.14 μg/mL, a value 7-fold greater than the predicted clinical Cmax).

Veliparib dihydrochloride was evaluated in repeated dose toxicity studies in rats and dogs. When administered as a sole agent to rats, the compound did not result in adverse effects at Cmax values that were greater than 19-fold the estimated therapeutic peak plasma drug concentration (highest dose tested). When rats were administered veliparib dihydrochloride in conjunction with a cytotoxic agent (cisplatin), no clinically meaningful exacerbations of cisplatin-associated toxicity were apparent at Cmax values that were up to 8-fold greater for veliparib than the estimated therapeutic value. Exacerbation of cisplatin-associated toxicity was limited to rats that received veliparib dihydrochloride in conjunction with cisplatin at the highest dose that yielded Cmax values 22-fold greater than the estimated therapeutic peak plasma drug concentration. In dogs, emesis, body weight losses related to anorexia, and convulsions were observed at doses of 30 mg base/kg/day with Cmax values 26-fold greater than the estimated therapeutic peak plasma concentration. Veliparib dihydrochloride was found to be negative in vitro for both mutagenicity and clastogenicity.

The non-toxic dose observed in the most sensitive mammalian species (beagle dogs) was 300 mg/m$^2$. Emesis and QT prolongation were observed in animal models, at 31-fold and 21-fold higher concentrations than the predicted clinical Cmax (0.21 μg/mL), respectively. Based on different sensitivities to seizures between rodents and dogs, the plasma concentration that would be associated clinically with pro-convulsant activity will be difficult to define.

Clinical Investigations

A single-dose pharmacokinetic and pharmacodynamic endpoint study in cancer patients was initiated under an exploratory IND by the National Cancer Institute as the initial study in their phase 0 program. In this study, participants had baseline assessments of PAR in peripheral blood mononuclear cells (PBMCs) and at higher dose levels, in tumor from needle biopsies, assessed by a validated immunoassay. Participants received a single dose of veliparib at 10, 25, or 50 mg. PBMCs were collected over a 24 hour period at all dose levels, and tumor biopsies were obtained at the 25 mg dose level, approximately 3 to 6 hours after administration of veliparib. A total of 6 patients have been studied so far, 3 each for the 10 mg and 25 mg cohorts. No treatment related adverse events have been observed. The target plasma Cmax of 210 nM was exceeded in 2 of 3 patients at the 10 mg dose level, and in all three patients for at least 4 hours at the 25 mg dose level. Levels of PAR were reduced 80-99% from baseline levels after administration of veliparib in both the PBMCs and tumor samples at the 25 mg dose level. Thus, there is reason to believe that target inhibition is seen at least at the 25 mg dose level, and may be occurring at doses lower than 25 mg.

Several combination phase I trials were ongoing. Also, single agent dose escalation trial is ongoing in the BRCA deficient population. Of these, A Phase I study of veliparib in combination with metronomic cyclophosphamide in adults with refractory solid tumors and lymphomas has finished. The combination was well tolerated and 60 mg QD veliparib was determined to be the MTD to be combined with 50 mg QD of cyclophosphomide (Kummar S et al, Clin Cancer Res. 2012 Mar. 15; 18(6):1726-1734). Multiple phase II studies with the veliparib/cyclophosphamide combination to treat breast cancer, ovarian cancer and lymphoma are ongoing. In another study, 10 mg BID veliparib was determined to be the MTD in combination with topotecan 0.6 mg/m$^2$/d (Kummar S Cancer Res. 2011 Sep. 1; 71(17): 5626-34). 2.2 Gemcitabine and Intensity Modulated Radiation Therapy for Pancreatic Cancer Surgical resection is considered to be the only treatment option with curative potential for patients with pancreatic cancer. However, the majority of these patients do not have resectable disease at presentation. More than 85% of patients have locally advanced or metastatic disease when initially diagnosed. First-line chemotherapy for locally advanced/metastatic pancreatic cancer is gemcitabine, (2',2'-Difluoro-2'-deoxycytidine), which is a fluorine substituted analog of Cytarabine. It has demonstrated anti-tumor activity in a number of murine tumor models and in human tumor xenografts. Gemcitabine has been used as either a single agent or in combination with other drugs for the primary treatment of locally advanced and metastatic pancreatic carcinomas. In the pivotal trial for which the FDA approved this drug, patients treated with gemcitabine had a modest improvement in survival compared to patients treated with 5 FU. The median survival was improved from 4.41 months to 5.56 months. However, nearly 25% of patients receiving gemcitabine were noted to have a clinical benefit compared to 5% of patients receiving 5 FU.

In a recent meta-analysis, the addition of platinum analogs to gemcitabine demonstrated a survival benefit in patients with a good performance status. However, additional studies are necessary to determine which therapeutics are best combined with gemcitabine. Response rates of 11-22% have been reported in heavily pretreated patients, and up to 42% in chemo naïve patients. Gemcitabine has been shown to decrease the intracellular deoxyribose nucleotide pools and to increase the radiosensitivity of cells in vitro. Thus, gemcitabine is not only an agent with significant systemic activity, but also a potent radiosensitizer. A recent study compared full dose gemcitabine (1000 mg/m$^2$) to a lower dose of gemcitabine (600 mg/m$^2$) combined with standard fractionated radiation (50.4 Gy over 5.5 weeks). Although the study was closed prior to reaching its planned accrual, there was a significant improvement in survival with combined gemcitabine and radiation compared to gemcitabine alone. Objective responses were observed in 2.7% in the gemcitabine alone arm (95% CI [0.09%, 14.1%]) and 8.8% in the combined arm (95% CI [1.9%, 23.7%]). In this trial, the dose of gemcitabine was reduced to 600 mg/m$^2$ with radiation and patients required a 4 week break prior to resuming full dose gemcitabine. Grade IV toxicity, principally gastrointestinal and hematologic, was more common in the combined group (41.2 vs. 5.7%; p<0.0001). Although there was an improvement in survival, patients who received combined chemoradiation had substantially more toxicity when compared to gemcitabine alone. A formal full-dose gemcitabine with concurrent radiation dose escalation trial was conducted but, with 3D techniques, it was not possible to escalate the radiation dose beyond 36Gy. IMRT can reduce the dose to Organs-At-Risk and simultaneously allow an increase in target dose in unresectable pancreatic cancer. To determine the maximum tolerated radiation dose deliverable with IMRT and concurrent full-dose gemcitabine a phase I/II trial (UMCC 2006-018) was initiated at the University of Michigan by Ben Josef et al. In this trial it was elected to combine radiotherapy with concurrent gemcitabine administered by a fixed dose-rate infusion schedule (FDR-G). The rationale was based on the finding that phosphorylation of gemcitabine to the monophosphate form by deoxycytidine kinase is the rate-limiting step in the accumulation of the active diphosphate and triphosphate metabolites. It has been demonstrated in clinical trials that accumulation of gemcitabine triphosphate in mononuclear cells during therapy is saturable, and that the optimal plasma concentration of gemcitabine that maximized the rate of formation of gemcitabine triphosphate is approximately 20 mol/L. Optimal levels were achieved at an infusion rate of gemcitabine of approximating 10 mg/m$^2$/min. Preclinical data, using human tumor cell lines (including pancreatic carcinoma cell lines), have suggested improved cytoxicity. The concept was then tested in phase I and phase II trials. In the later, patients with locally advanced and metastatic pancreatic adenocarcinoma were treated with 2,200 mg/m$^2$ gemcitabine over 30 minutes (standard arm) or 1,500 mg/m$^2$ gemcitabine over 150 minutes (FDR arm) on days 1, 8, and 15 of every 4-week cycle. Ninety-two patients were enrolled; 91% of the patients had metastatic disease. The median survival for all patients was 5.0 months in the standard arm and 8.0 months in the FDR arm (P=0.013). Patients in the FDR infusion arm experienced increased but acceptable hematologic toxicity.

Pharmacokinetic analyses demonstrated a two-fold increase in intracellular gemcitabine triphosphate concentration in the FDR arm. In UMCC 2006-018, patients received FDR-G (1000 mg/m$^2$, 100-minute infusion) on days −22 and −15 during a run in period. Protocol therapy started on day 1 and consisted of FDR-G on days 1, 8, 22, and 29, concurrently with IMRT at escalating doses. Post IMRT, 4 cycles of FDR-G were administered. The radiation doses ranged from 50Gy to 60Gy, all in 25 fractions. DLT's were observed in 6 patients; the interim posterior estimates of probability of DLT ranged from 0.17 to 0.28. The response rate was 52.4% (95% CI 29.8% to 74.3%). The median overall survival and progression-free survival were 23.1 months (95% CI 9-23.1) and 7.2 months (95% CI 5.0-8.0), respectively.

Current treatment of non-metastatic, unresectable pancreatic cancer results in dismal median survival rates of 11-12 months, nearly uniform local persistence of disease and poor local control. Indeed, recent data suggests that failure to control the primary tumor results in complications that contribute to mortality in approximately 30% of patients. Gemcitabine has been used as a single agent, as well as in combination with other drugs, for the primary treatment of locally advanced and metastatic pancreatic carcinomas. Response rates of 11-22% have been reported in heavily pretreated patients, and up to 42% in chemo naïve patients. Whereas its value has been substantiated in many clinical trials, its use with concurrent radiation therapy remains controversial with mixed results. A Phase I study evaluated radiation dose escalation using three-dimensional conformal techniques with full-dose gemcitabine, yet it was not possible to escalate the dose beyond 36 Gray (Gy; 2.4 Gy daily fractions) secondary to gastrointestinal toxicities. A follow-up multi-center Phase II study confirmed this regimen to be well-tolerated, while showing response rates of 5.1% and disease control rates of 84.6%. In an attempt to minimize dose-limiting toxicities to organs-at-risk and simultaneously allow an increase in target dose, Ben Josef et al. recently reported excellent outcomes (response rate of 52.4%, median overall survival 23.1 months) using dose-escalated intensity modulated radiation therapy (IMRT) with full-dose gemcitabine (Ben-Josef 2008 ASCO). Unfortunately, other contemporary trials have failed to show such promising results with the use of concurrent radiation therapy (Chauffert 2008; Loehrer 2008 ASCO). As a result, more effective multimodal treatment strategies are required and clinical trials integrating novel therapeutic agents should be initiated.

Targeting of the poly (ADP-ribose) polymerase (PARP)-1 and 2 proteins has shown excellent anti-tumor activity when combined with other cytotoxic therapies, including gemcitabine and radiation. As a result, clinical development of PARP inhibitors follows two distinct approaches: targeting tumor cells with pre-existing defects in DSB repair, such as BRCA-deficient cells, which are genetically predisposed to die when PARP activity is lost; and combining PARP inhibition with DNA-damaging agents, such as ionizing radiation, to derive additional therapeutic benefit from DNA damage. A recent phase II study evaluated BSI-201, a potent PARP1 inhibitor, in combination with gemcitabine (1000 mg/m$^2$) and carboplatin (AUC=2) in subjects with metastatic triple negative breast cancer. Patients randomized to receive concurrent BSI-201 had improved CBR, median PFS, and median OS, compared with chemotherapy alone. Additionally, the frequency and nature of adverse events did not differ between arms. A phase 0, single-dose pharmacokinetic and pharmacodynamic endpoint study of ABT-888 (veliparib) in cancer patients showed reduction in PAR levels (80-99%) in tumor biopsies after a single dose of 25 mg with no treatment related adverse events noted.

We investigated the addition of veliparib to gemcitabine and focused radiotherapy in vitro and in vivo using our new preclinical pancreatic cancer radiation research model. In vitro, irradiation of the human pancreatic carcinoma cell line, MiaPaCa-2, led to significant upregulation of PAR protein, which was abrogated following co-treatment with veliparib, confirming PARP as a potential target in pancreatic cancer. Simultaneous upregulation of phospho-ATM levels were also noted with irradiation plus veliparib relative to either therapy alone, suggesting increased double-strand DNA damage and repair through HR. Co-treatment with 5 Gy and 1, 10 or 100 uM of veliparib led to dose enhancement factors of 1.29, 1.41 and 2.36, respectively suggesting a synergistic mechanism of cell death. Additionally, minimal cytotoxicity was noted when cells were treated with veliparib alone up to 100 uM. Radiation-induced caspase 3/7 activity was also significantly enhanced by veliparib, thereby indicating increased cell death through apoptosis. PARP activity was quantified using ELISA and confirmed expression patterns seen with Western blot. These levels also correlated with levels of tumor apoptosis suggesting accurate target inhibition, as well as the potential to use PARP activity and PAR levels as a predictive clinical biomarker. In vivo, treatment with a single dose of veliparib, radiotherapy or veliparib plus radiotherapy led to tumor growth inhibition of 8, 30 and 39 days ($p<0.05$), respectively; survival at 30 days for these groups was 63%, 75% and 100%, while at 60 days, it was 0%, 0% and 29% ($p<0.05$), respectively. Taken together, without being bound to any particular theory, these data supported our phase I clinical trial with ABT888 in combination with gemcitabine and radiation therapy for pancreatic cancer patients.

Phase 1 Trial

Phase I Study of veliparib (ABT-888) in combination with Gemcitabine and Intensity Modulated Radiation Therapy in Patients with Locally Advanced, Unresectable Pancreatic Cancer. The primary objectives were to 1) determine the maximum tolerable dose of veliparib in combination with gemcitabine and intensity modulated radiation therapy in patients with locally advanced pancreatic cancer and 2) determine the safety and toxicity of the combination of veliparib with gemcitabine and radiation therapy in patients with locally advanced pancreatic cancer.

The primary outcome measure was the maximum-tolerated dose (MTD) of veliparib based on the incidence of dose-limiting toxicity (DLT) as assessed by the National Cancer Institute (NCI) Common Terminology Criteria for Adverse Events (CTCAE) version 4.0 (Phase I) [Time Frame: Days 1-70].

The secondary outcome measures included 1) the assessment of objective response rates measured by Response Evaluation Criteria in Solid Tumors (RECIST 1.1) [Time Frame: From baseline to Week 26]. Only those patients who have measurable disease present at baseline, have received at least one cycle of therapy, and have had their disease re-evaluated were considered evaluable for response; 2) Evaluation of pre-treatment biopsy specimens for levels of various DNA repair proteins [Time Frame: Baseline only]; and 3) Change in PAR [Poly(ADP-ribosyl)ation] levels in peripheral blood mononuclear cells [Time Frame: Baseline, Weekly for 6 weeks, and at Weeks 10, 18, and 26].

Gemcitabine was administered by intravenous infusion of 1000 mg/m$^2$ over 30 minutes on days 1, 8, 15 of the cycle. Intensity modulated radiation therapy (IMRT) was given to a total dose of 36 Gy in 15 fractions (2.4 Gy per fraction, one fraction per day, 5 fractions per week, Monday through Friday) beginning on day 1. Veliparib was administered per a dose escalation schema. The starting dose of veliparib is 20 mg BID based upon safety/efficacy data available. Dose escalation continued in 20 mg increments until the maximum tolerated dose (MTD) is reached. Intra-patient dose escalation was not allowed.

Eligibility for the trial included: Ages Eligible for Study –18 Years and older (Adult, Senior); Sexes Eligible for Study: All and No Healthy Volunteers are accepted. Inclusion Criteria were: 1) Patients with histopathological or cytological diagnosis of adenocarcinoma of the pancreas, as well as those with high clinical suspicion of adenocarcinoma, which is deemed locally advanced unresectable or borderline resectable as determined by a pancreatic cancer surgeon and/or following evaluation by a GI oncology tumor board, and 2) Age 18 years or older. Exclusion Criteria are: 1) Patients who have had prior anti-cancer treatment for their disease; 2) Patients who are currently receiving any other investigational agents, 3) Metastatic disease; 4) History of allergic reactions attributed to compounds of similar chemical or biologic composition to PARP [Poly (ADP-ribosome) polymerase] inhibitors or gemcitabine; and 4) Uncontrolled intercurrent illness including, but not limited to, ongoing or active infection, symptomatic congestive heart failure, unstable angina pectoris, cardiac arrhythmia, or psychiatric illness/social situations that would limit compliance with study requirements.

Agent Administration

Treatment was administered on an outpatient basis. Appropriate dose modifications for gemcitabine and radiation therapy are described herein. The investigational treatment cycle was 3 weeks followed by once weekly evaluation for an additional 3 weeks. First post-treatment imaging and follow up was performed 10 weeks after initiating therapy. Patients removed from study for unacceptable adverse events were followed until resolution or stabilization of the adverse event. In addition, subjects were evaluated for safety/toxicity and post treatment imaging at weeks 18 and 26.

Gemcitabine was administered by intravenous infusion of 1000 mg/m$^2$ over 30 minutes on days 1, 8, 15 of the cycle. Intensity modulated radiation therapy (IMRT) was given to a total dose of 36 Gy in 15 fractions (2.4 Gy per fraction, one fraction per day, 5 fractions per week, Monday through Friday) beginning on day 1. Veliparib was administered per the dose escalation schema, below, beginning on day 1. The starting dose of veliparib is 20 mg BID based upon safety/efficacy data available from the Investigator's Brochure. Dose escalation continued in 20 mg increments until the maximum tolerated dose (MTD) is reached.

In this trial, the minimum veliparib dose to be given was 20 mg BID. The first patient was enrolled to the trial and assigned 20 mg BID. Treatment will be delivered over 3 weeks. Patients were evaluated for DLT during the treatment period, as well as for an additional 24 weeks post-treatment as outlined in the schema above. Therefore, patients were evaluable for DLT during a 10 week period (treatment cycle). The second patient entered the trial when the first patient has cleared DLT evaluation. The trial would be terminated if three DLTs are observed from patients treated with 20 mg. The maximum number of patients to be treated simultaneously with unresolved DLT status could not exceed 3. In other words, if there were three patients currently under study with unresolved DLT status, a new patient cannot be treated until at least one patient finishes one cycle of therapy. After the first patient cleared the 20 mg BID dose, i.e. no DLT at the end of treatment cycle, subsequent patients were enrolled at any time. It was estimated that a maximum of 30 patients will be accrued to the trial. Upon completion of the trial, the MTD was estimated as the median of the marginal posterior distribution of the MTD. The computation of the dose to be administered to each patient and the 95% highest posterior density credible interval estimate of the MTD was carried out with the software WinBUGS. In order to appropriately assess toxicity and possible dose limiting toxicities during drawn as per the study calendar for a total of 6 consecutive weeks and again during week 10 follow up. Therapy could be administered provided that the patient has no evidence of progressive disease and meets criteria for treatment.

Dose Modifications

Toxicity was evaluated using the NCI Common Terminology Criteria for Adverse Events, Version 4.0. The frequency of toxicities per organ system was tabulated using descriptive statistics. All patients who receive any amount of the study drug were evaluable for toxicity.

TABLE 4

Dose Escalation Schedule
Dose Escalation Schedule

| Dose Level | Veliparib* Dose PO BID Days 1-21 (weeks 1-3) | Gemcitabine IV 1000 mg/m$^2$ Days 1, 8, and 15 (weeks 1-3) | Radiation Dosage Monday-Friday Weeks 1-3 |
|---|---|---|---|
| Level 1 | 20 mg | 1000 mg/m$^2$ | 36 Gy |
| Level 2 | 40 mg | 1000 mg/m$^2$ | 36 Gy |
| Level 3 | 60 mg | 1000 mg/m$^2$ | 36 Gy |
| Level 4 | 80 mg | 1000 mg/m$^2$ | 36 Gy |

*Dose escalation will continue in 20 mg increments until MTD is achieved.

Veliparib was supplied by Abbott Laboratories as immediate release capsules at dosage strengths of 10, 20, 40, 50, and 100 mg. Capsules were stored in their original container at room temperature. Patients were instructed to swallow the tablets whole (do not chew, crush, or break the tablets). Veliparib was dosed BID, orally, one in the morning and the other in the evening. The time interval should be ~12 hr in between the two doses. Fasting was not required for veliparib dosing. If the subject vomits within 15 minutes of taking veliparib AND all capsules come out intact, another dose was administered. The dose may only be repeated once. If more than 15 minutes have passed from the time of oral dosing OR the capsules have been broken or dissolved, then no additional doses should be taken.

Radiation Therapy

The dose to the PTV was 36 Gy in 2.4 Gy fractions in 15 fraction delivered 5 days a week. Heterogeneity of −5% to +10% is permitted provided that normal-tissue constraints were met. Ninety-five percent of the PTV should receive at least 99% of the dose. Photon beams of 6MV or higher should be used.

Gemcitabine

Gemcitabine is an antineoplastic agent that is structurally related to cytarabine. It is a pyrimidine analogue that is cell-cycle specific. Gemcitabine is available commercially as a lyophilized powder in sterile vials containing 200 mg or 1 gram of gemcitabine as the hydrochloric salt (expressed as the free base) formulated with mannitol and sodium acetate.

Mechanism of Action

Gemcitabine is cytotoxic to cells undergoing DNA synthesis (S-phase) and also blocks the progression of cells through the G1/S-phase boundary. Gemcitabine is converted intracellularly to gemcitabine-5'-triphosphate, its active form. Steady-state plasma levels of gemcitabine occur within 15 minutes after starting the infusion. The elimination half-life of gemcitabine ranges from 32 to 638 minutes, depending on the age and gender of the patient and the rate of administration of gemcitabine.

Preparation and Administration

The lyophilized product was stored at controlled room temperature (20-25° C. or 68-79° F.). Once the drug has been reconstituted, it was stored at controlled room temperature and used within 24 hours. The manufacturer recommends solutions of gemcitabine not be refrigerated as crystallization may occur. Drug vials were reconstituted with normal saline added to the vial to make a solution ideally containing 10 mg/mL. The concentration for 200 mg and 1 g vials should be no greater than 40 mg/mL. An appropriate amount of drug was prepared with normal saline and administered as a 30-minute intravenous infusion on days 1, 8, 15 of the treatment cycle.

Maximum Tolerated Dose (MTD)

The MTD was defined to be the dose level of veliparib that when administered to a patient twice a day, orally, results in a probability equal to θ=0.4 that a dose limiting toxicity will be manifest within 10 weeks (treatment cycle). The dose escalation followed a Bayesian method permitting precise determination of the therapeutic working dose while directly controlling the likelihood of an overdose. The method is an extension of EWOC (Escalation With Overdose Control), where we model the time to DLT using a proportional hazards model with constant baseline hazard rate. Patients were allowed to enter the trial at any time and the dose allocated to the next patient was determined based on all available data from all previously treated and current patients under observation. The defining property of EWOC is that the expected proportion of patients treated at doses above the MTD is equal to a specified value α, the feasibility bound. This value is selected by the clinician and reflects his/her level of concern about overdosing. Zacks et al. showed that among designs with this defining property, EWOC minimizes the average amount by which patients are under dosed. This means that EWOC approaches the MTD as rapidly as possible, while keeping the expected proportion of patients overdosed less than the value α.

The dose for the first patient in the trial was 20 mg BID, previous results indicating this to be a safe dose. The dose for each subsequent patient was determined so that, on the basis of all available data, the probability that it exceeds the MTD is equal to a prespecified value α. In this trial, we started at α=0.25 and increase α in small increments of 0.05 until α=0.5, this value being a compromise between the therapeutic aspect of the agent and its toxic side effects. The prior distribution of the MTD is based on the correlated priors model M4 where the support of the MTD is (0, ∞). The a priori probability that the MTD exceeds 100 mg is 10%.

Dosing Delays/Dose Modifications
Veliparib Dose Delays/Reductions

Any subject who experiences Grade 3 or 4 toxicity felt at least possibly attributable to veliparib will stop veliparib until the toxicity resolves to <Grade 1 or baseline at time of study entry. After recovery, the subject will be allowed to resume veliparib at 1 dose level below the current level). Any dose reduction below dose level 1 will result in veliparib discontinuation. At the investigator's discretion, gemcitabine and radiotherapy may continue after veliparib has been discontinued.

Gemcitabine Dose Delays/Reductions

Protocol treatment will be dose modified at the discretion of the treating oncologist based on criteria outlined and described herein. Dose modifications can occur based on clinical evaluation at any point during the course of treatment and laboratory evaluations on Days 1, 8 and 15 of the cycle. Any grade 3 adverse event may be cause for gemcitabine to be withheld. Any grade 2 toxicity could be cause for dose modifications, at the discretion of the treating physician. Non-hematological Grade 2 adverse event may be cause to reduce the dose of gemcitabine by one dose level and maintained throughout therapy. This will be at the discretion of the institution's treating physician. If ANC is <500 or platelets <50 K, or the patient experiences febrile neutropenia, gemcitabine will be held until recovery per dose reduction guidelines below. Erythropoietin is allowed. Myeloid growth factors should not be used prophylactically but may be utilized to treat grade 3-4 ANC. Gemcitabine dose levels: level 0 (starting dose—1000 mg/m$^2$); level 1 (700 mg/m$^2$); level 2 (600 mg/m$^2$) and level 3 (500 mg/m$^2$).

Radiation Dose Delays/Reductions

Holding of radiation will be at the discretion of the treating radiation oncologist; missed dosing will be made up at the discretion of the treating radiation oncologist. All grade 4 discontinuations and/or toxicities will be reviewed by the principal investigator and IRB to determine if patients should remain on study with appropriate dose adjustments. Radiation will be continued unless toxicity is possibly related to radiation treatment; for example, diarrhea, intractable nausea and/or vomiting, and/or unable to maintain 30% of their body weight during treatment. If these toxicities are thought to be caused by radiation then radiation treatment will be delayed until these toxicities are grade 1 or less. Dose reduction or withholding of gemcitabine does not necessarily preclude treatment with radiation.

Measurement of Effect

For the purposes of this study, patients were re-evaluated for response 10 weeks after initiation of therapy. Antitumor Effect—Solid Tumors—Response and progression will be evaluated in this study using the new international criteria proposed by the Response Evaluation Criteria in Solid Tumors (RECIST 1.1). Changes in only the largest diameter (unidimensional measurement) of the tumor lesions are used in the RECIST 1.1 criteria.

Disease Parameters

Measurable disease. Measurable lesions were defined as those that can be accurately measured in at least one dimension (longest diameter to be recorded) as >10 mm with spiral CT scan. All tumor measurements must be recorded in millimeters (or decimal fractions of centimeters). Malignant lymph nodes: To be considered pathologically enlarged and measurable, a lymph node must be >15 mm in short axis when assessed by CT scan (CT scan slice thickness recommended to be no greater than 5 mm). At baseline and in follow-up, only the short axis will be measured and followed.

Methods for Evaluation of Measurable Disease

All measurements are taken and recorded in metric notation using a ruler or calipers. All baseline evaluations are performed as closely as possible to the beginning of treatment and never more than 4 weeks before the beginning of the treatment. The same method of assessment and the same technique should be used to characterize each identified and reported lesion at baseline and during follow-up. Conventional CT and MRI These techniques were performed with cuts of 10 mm or less in slice thickness contiguously. Spiral CT were performed using a 5 mm contiguous reconstruction algorithm. This applies to tumors of the chest, abdomen, and pelvis. PET-CT at present, the low dose or attenuation correction CT portion of a combined PET-CT is not always of optimal diagnostic CT quality for use with RECIST measurements. However, if the site can document that the CT performed as part of a PET-CT is of identical diagnostic quality to a diagnostic CT (with IV and oral contrast), then the CT portion of the PET-CT can be used for RECIST measurements and can be used interchangeably with conventional CT in accurately measuring cancer lesions over time. Note, however, that the PET portion of the CT introduces additional data which may bias an investigator if it is not routinely or serially performed.

Endoscopy, Laparoscopy The utilization of these techniques for objective tumor evaluation has not yet been fully and widely validated. Their uses in this specific context require sophisticated equipment and a high level of expertise that may only be available in some centers. Therefore, the utilization of such techniques for objective tumor response should be restricted to validation purposes in reference centers. However, such techniques may be useful to confirm complete pathological response when biopsies are obtained. Tumor markers Tumor markers alone cannot be used to assess response. If markers are initially above the upper normal limit, they must normalize for a patient to be considered in complete clinical response. Cytology, Histology These techniques can be used to differentiate between partial responses (PR) and complete responses (CR) in rare. FDG-PET While FDG-PET response assessments need additional study, it is sometimes reasonable to incorporate the use of FDG-PET scanning to complement CT scanning in assessment of progression (particularly possible 'new' disease). New lesions on the basis of FDG-PET imaging can be identified according to the following algorithm: a. Negative FDG-PET at baseline, with a positive FDG-PET at follow-up is a sign of PD based on a new lesion. b. No FDG-PET at baseline and a positive FDG-PET at follow-up: If the positive FDG-PET at follow-up corresponds to a new site of disease confirmed by CT, this is PD. If the positive FDG-PET at follow-up is not confirmed as a new site of disease on CT, additional follow-up CT scans are needed to determine if there is truly progression occurring at that site (if so, the date of PD will be the date of the initial abnormal FDG-PET scan). If the positive FDG-PET at follow-up corresponds to a pre-existing site of disease on CT that is not progressing on the basis of the anatomic images, this is not PD. c. FDG-PET may be used to upgrade a response to a CR in a manner similar to a biopsy in cases where a residual radiographic abnormality is thought to represent fibrosis or scarring. The use of FDG-PET in this circumstance should be prospectively described in the protocol and supported by disease-specific medical literature for the indication. However, it must be acknowledged that both approaches may lead to false positive CR due to limitations of FDG-PET and biopsy resolution/sensitivity.

Statistical Considerations

This is a Phase I study of veliparib in combination with gemcitabine and radiation therapy in patients with locally advanced pancreatic cancer. The dose escalation portion of the study was used to determine the maximum tolerable dose (MTD) of veliparib in combination with radiation and gemcitabine.

The aim of this phase I trial was to determine the MTD of veliparib administered orally to patients with locally advanced, unresectable pancreatic cancer. The MTD was defined to be the dose level of veliparib that when administered to a patient twice a day results in a probability equal to $\theta=0.25$ that a dose limiting toxicity (section 5.2) will be manifest within ten weeks.

Figure 15:
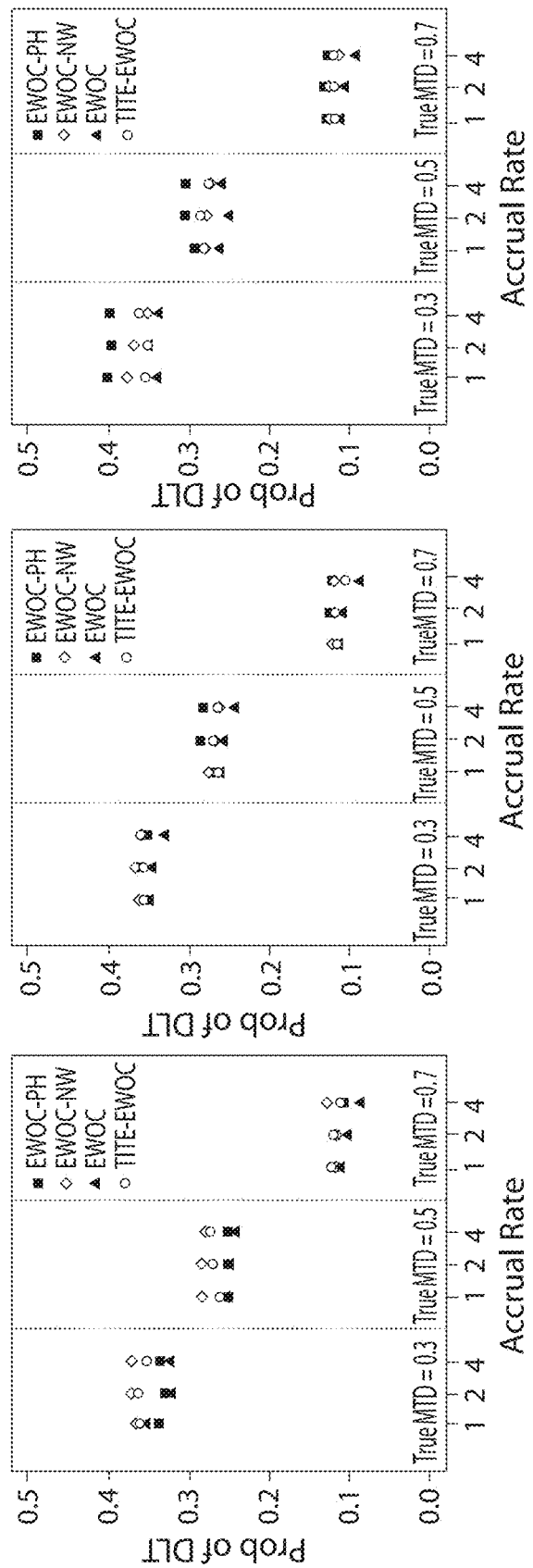
FIG. 15 depicts in accordance with various embodiments of the invention, the average proportion of patients exhibiting DLT under the nine different scenarios. DLT responses are generated from a Weibull model with shape parameter k–0.8 (left plot), k=1.0 (middle plot), and k=1.2 (right plot).
Figure 16:
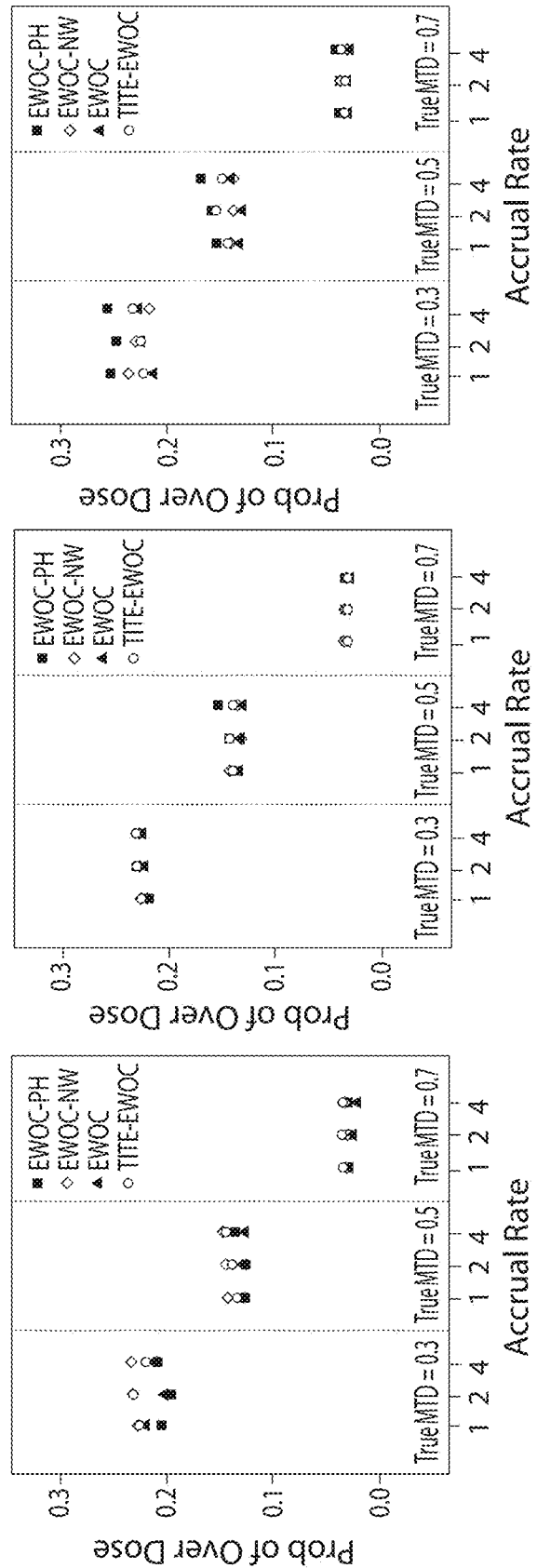
FIG. 16 depicts in accordance with various embodiments of the invention, the average proportion of patients given doses above the true MTD. DLT responses are generated from a Weibull model with shape parameter k–0.8 (left plot), k=1.0 (middle plot), and k=1.2 (right plot).
Figure 17:
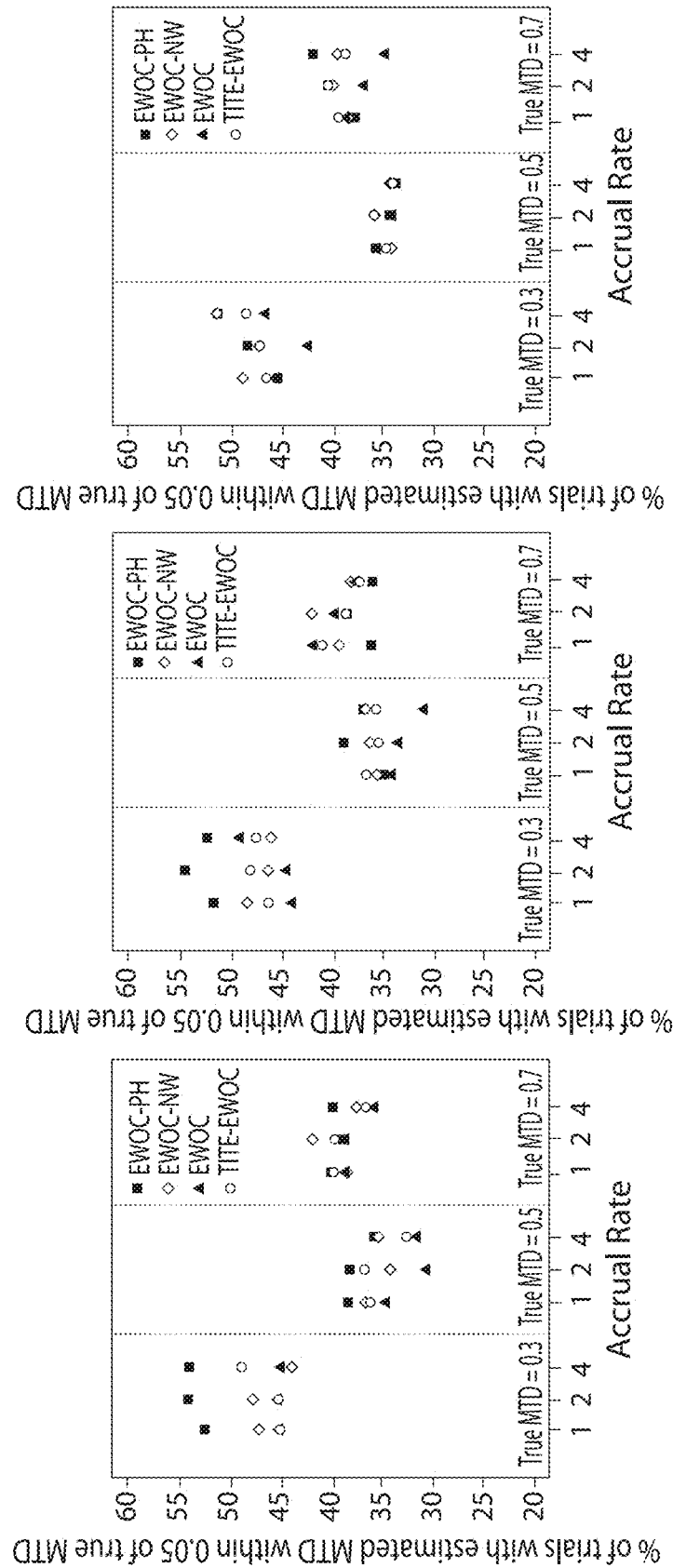
FIG. 17 depicts in accordance with various embodiments of the invention, the percent trial with recommended MTD within 0.05 of the true MTD. DLT responses are generated from a Weibull model with shape parameter k–0.8 (left plot), k=1.0 (middle plot), and k=1.2 (right plot).
Figure 18:
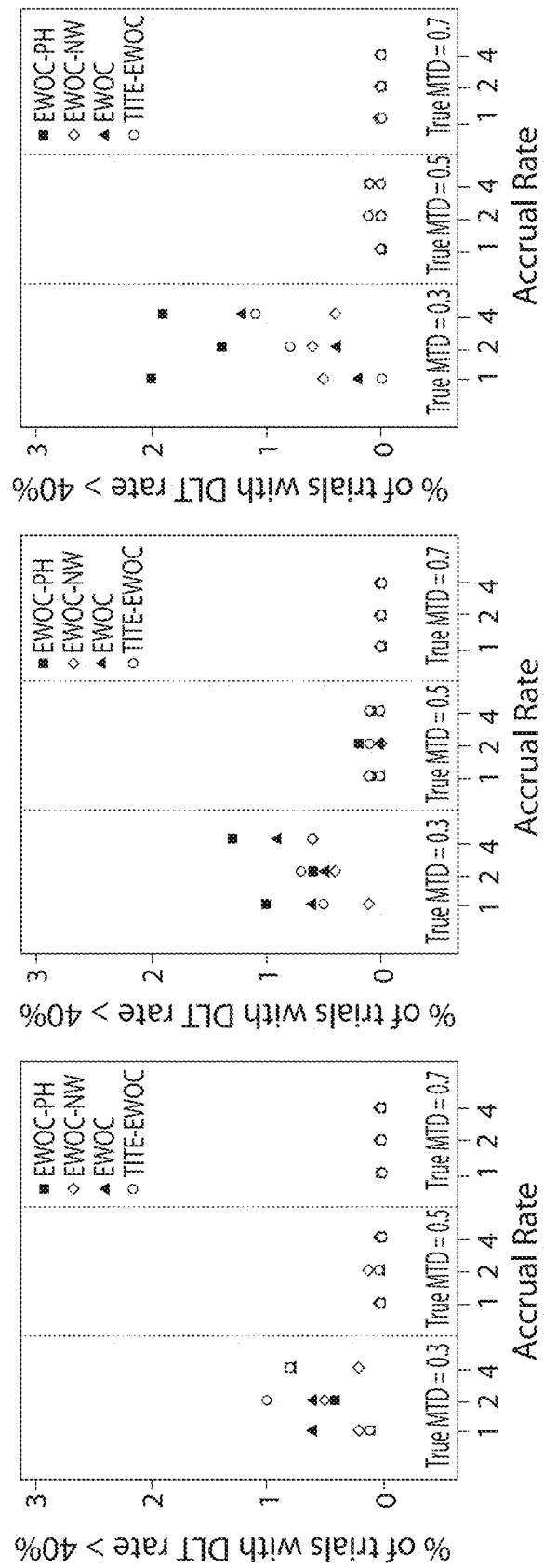
FIG. 18 depicts in accordance with various embodiments of the invention, the percent of trials with DLT rate exceeding 40%. DLT responses are generated from a Weibull model with shape parameter k−0.8 (left plot), k=1.0 (middle plot), and k=1.2 (right plot).
Figure 19:
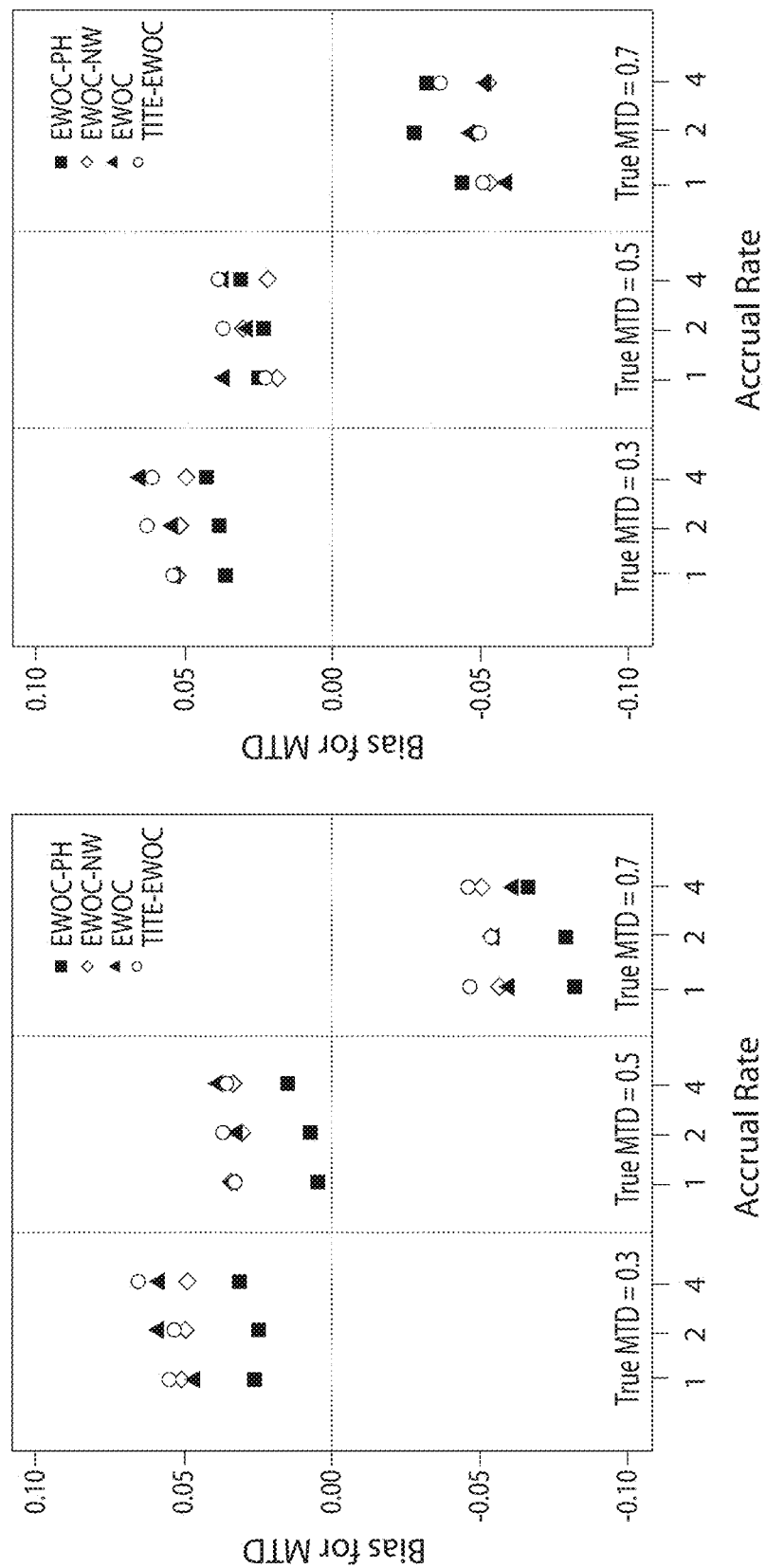
FIG. 19 depicts in accordance with various embodiments of the invention, the average bias of the estimate of the MTD under the nine different scenarios. DLT responses are generated from a Weibull model with shape parameter k−0.8 (left plot), k=1.0 (middle plot), and k=1.2 (right plot).
Figure 20:
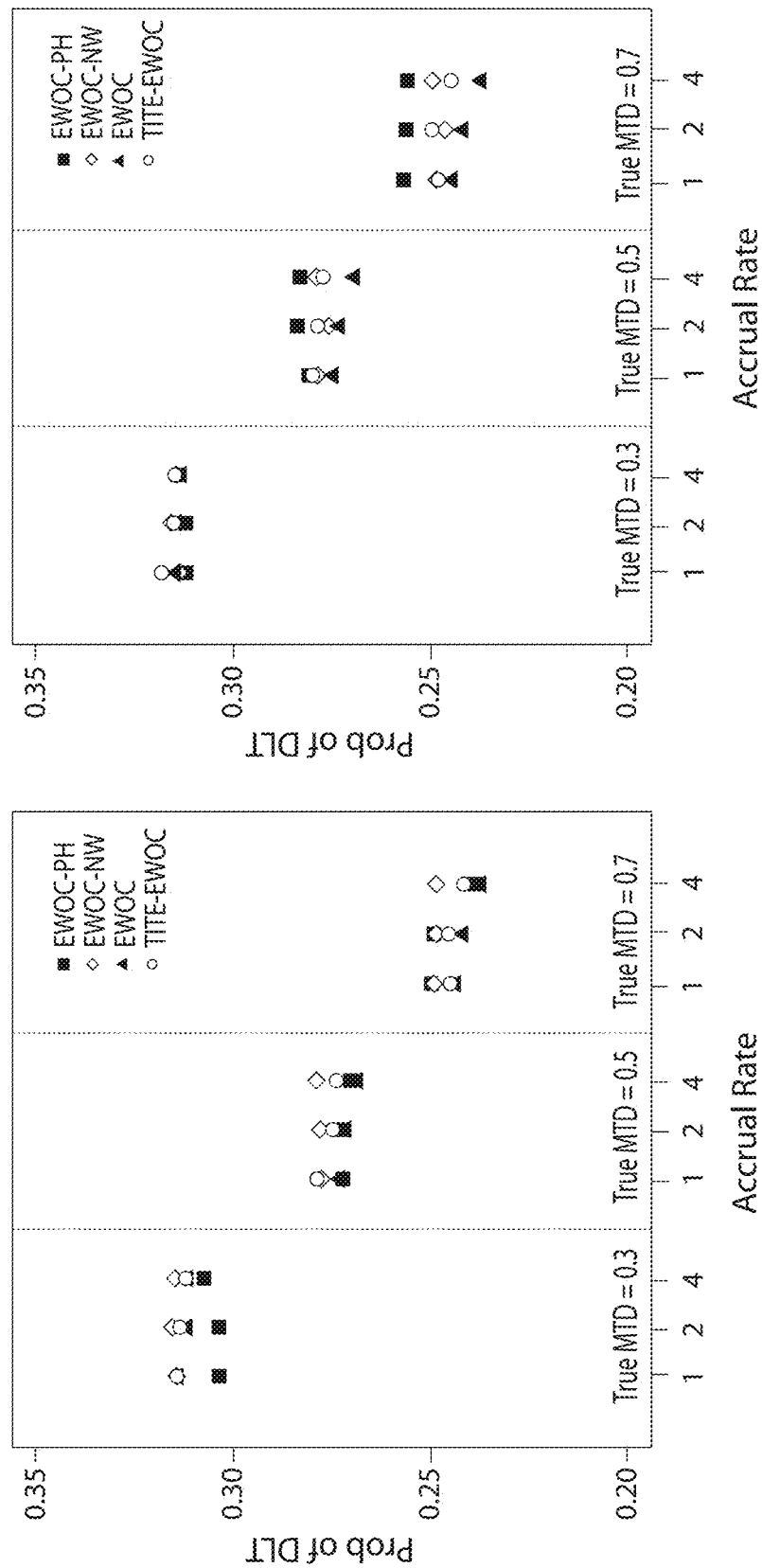
FIG. 20 depicts in accordance with various embodiments of the invention, the average proportion of patients exhibiting DLT under the nine different scenarios. DLT responses are generated from a non-proportional hazards model with $\beta 2=0.5$ (left plot) and $\beta 2=2.0$ (right plot).
Figure 21:
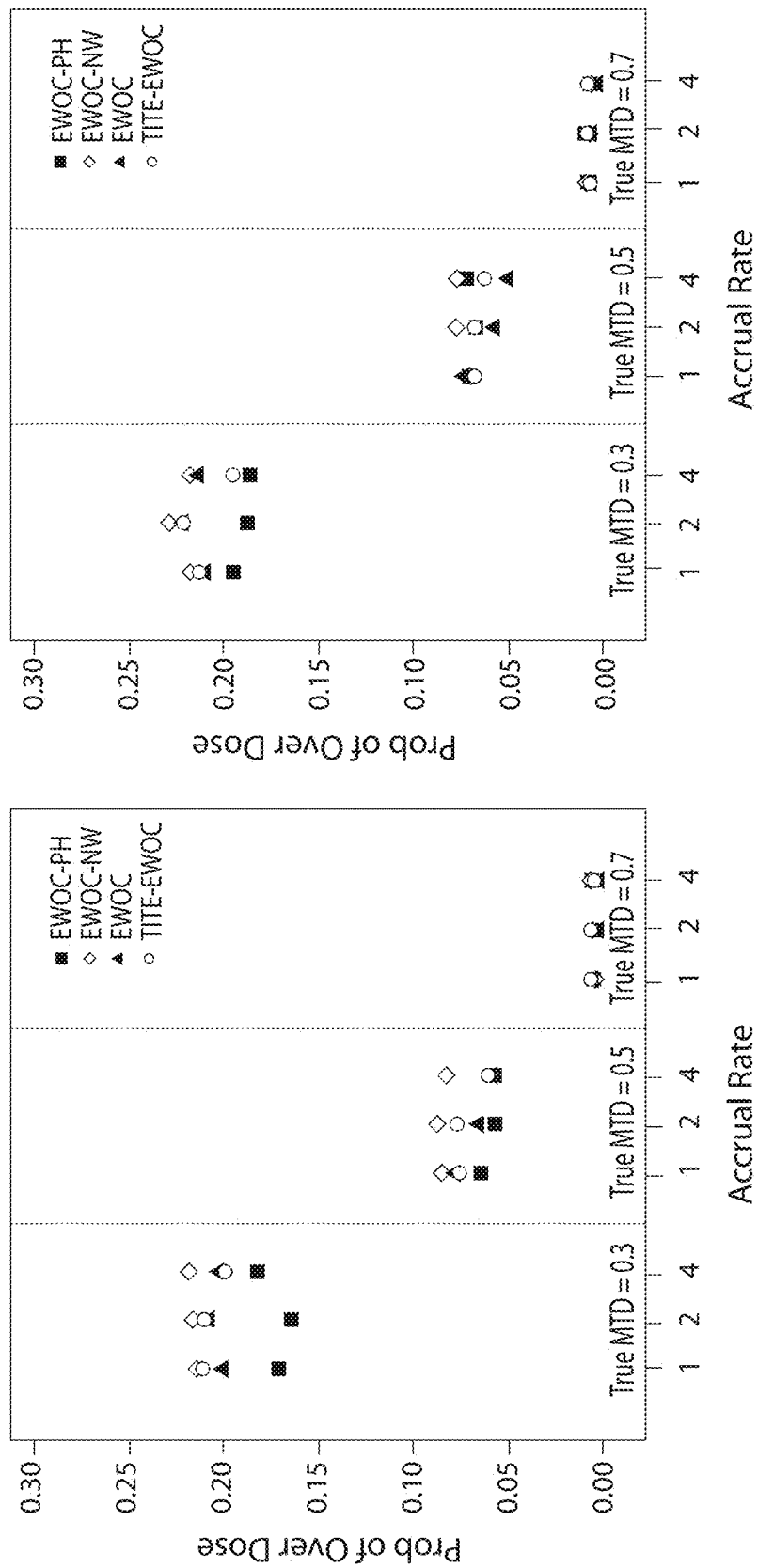
FIG. 21 depicts in accordance with various embodiments of the invention, the average proportion of patients given doses above true MTD. DLT responses are generated from a non-proportional hazards model with $\beta 2=0.5$ (left plot) and $\beta 2=2.0$ (right plot).
Figure 22:
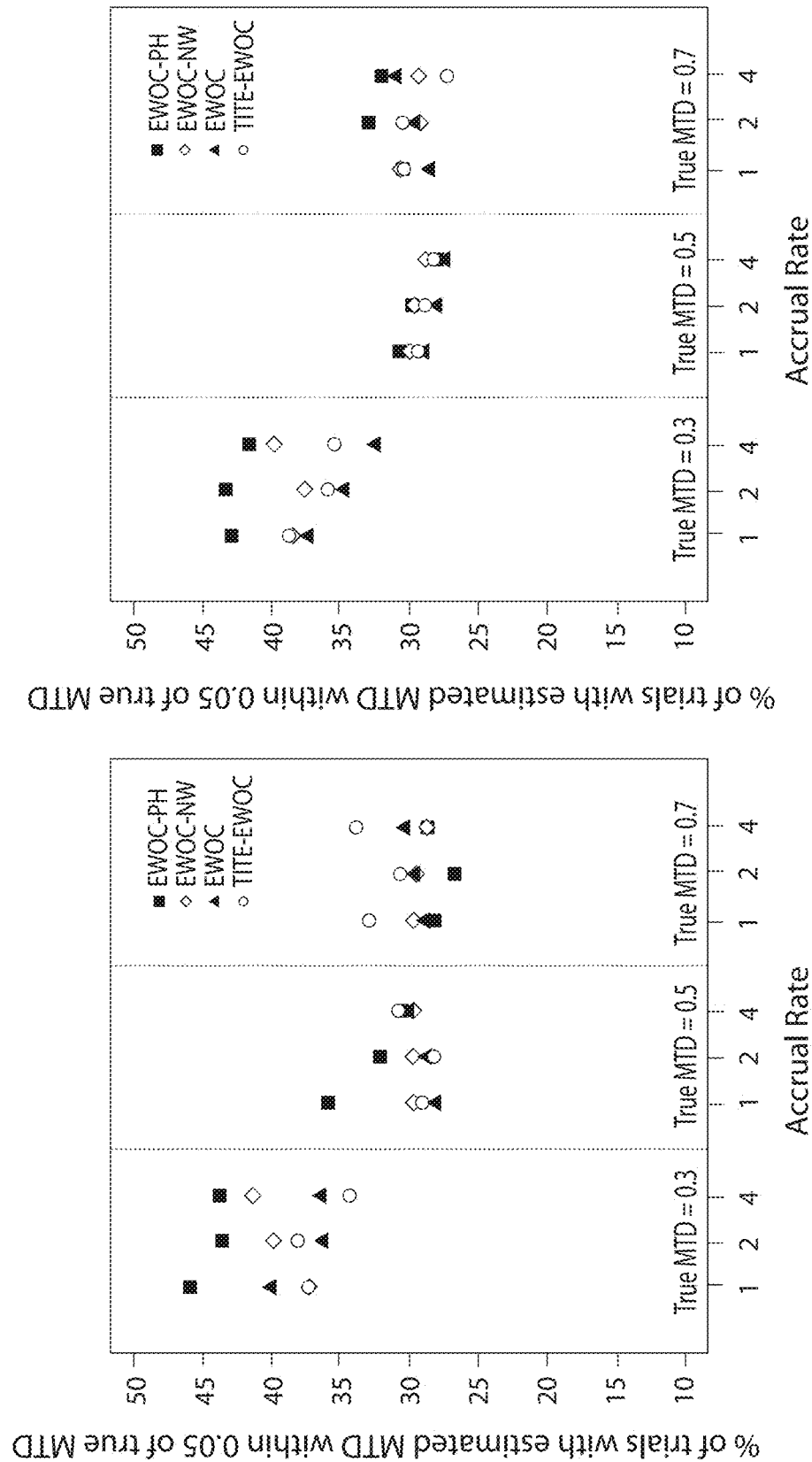
FIG. 22 depicts in accordance with various embodiments of the invention, the percent of trials with recommended MTD within 0.05 of the true MTD. DLT responses are generated from a non-proportional hazards model with $\beta 2=0.5$ (left plot) and $\beta 2=2.0$ (right plot).
Figure 23:
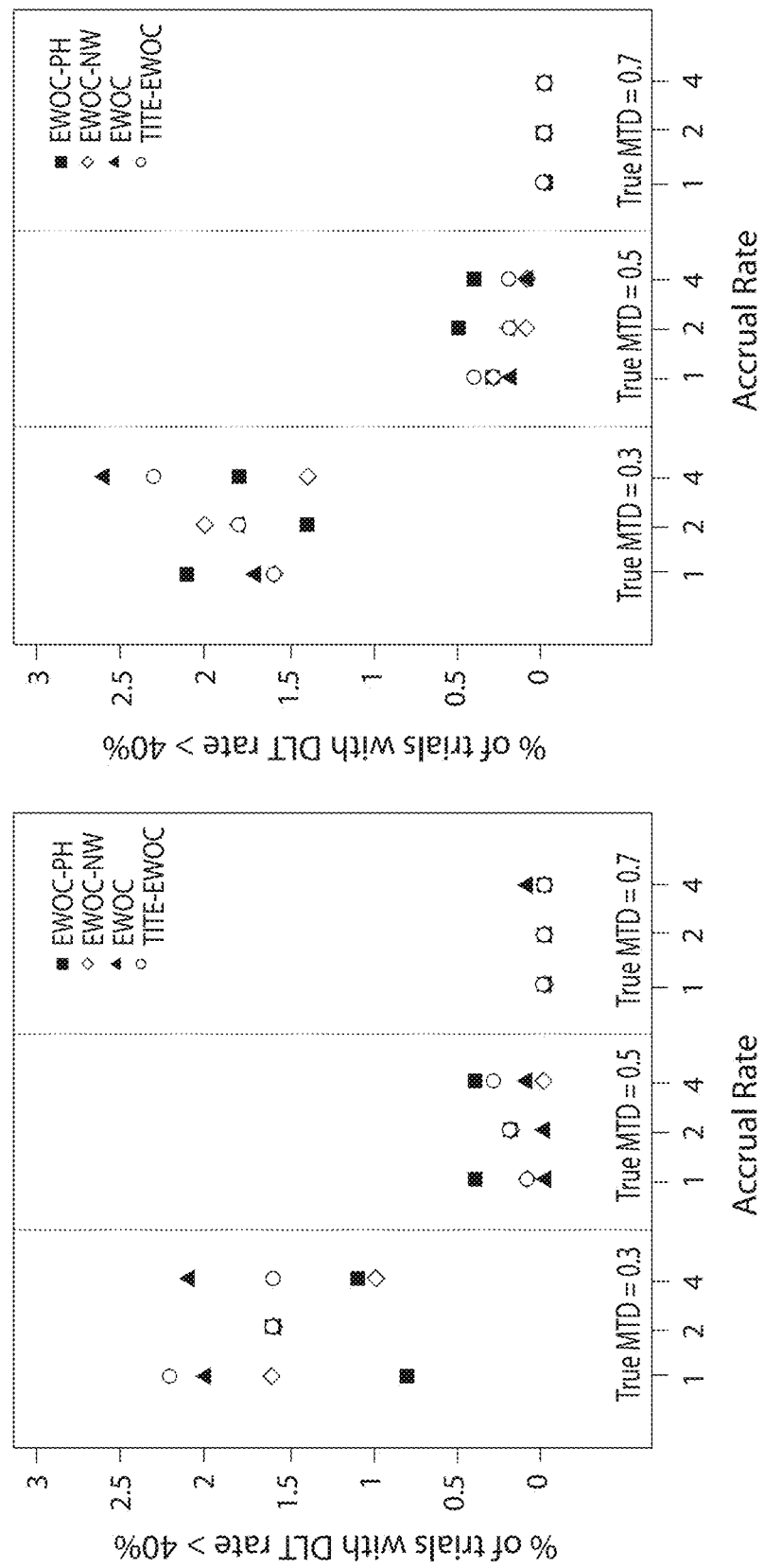
FIG. 23 depicts in accordance with various embodiments of the invention, the percent of trials with DLT rate exceeding 40%. DLT responses are generated from a non-proportional hazards model with $\beta 2=0.5$ (left plot) and $\beta 2=2.0$ (right plot).
Figure 24B:
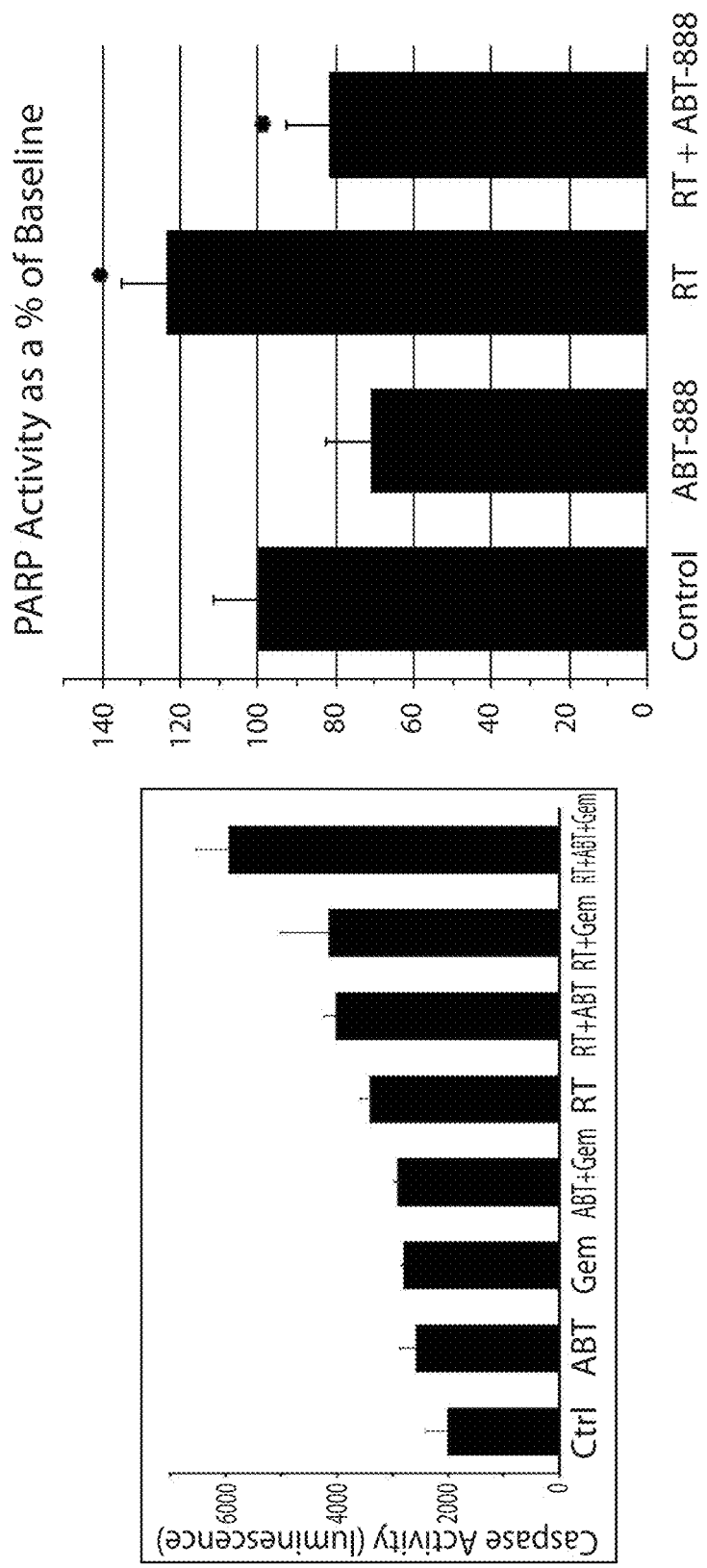
Figure 25B:
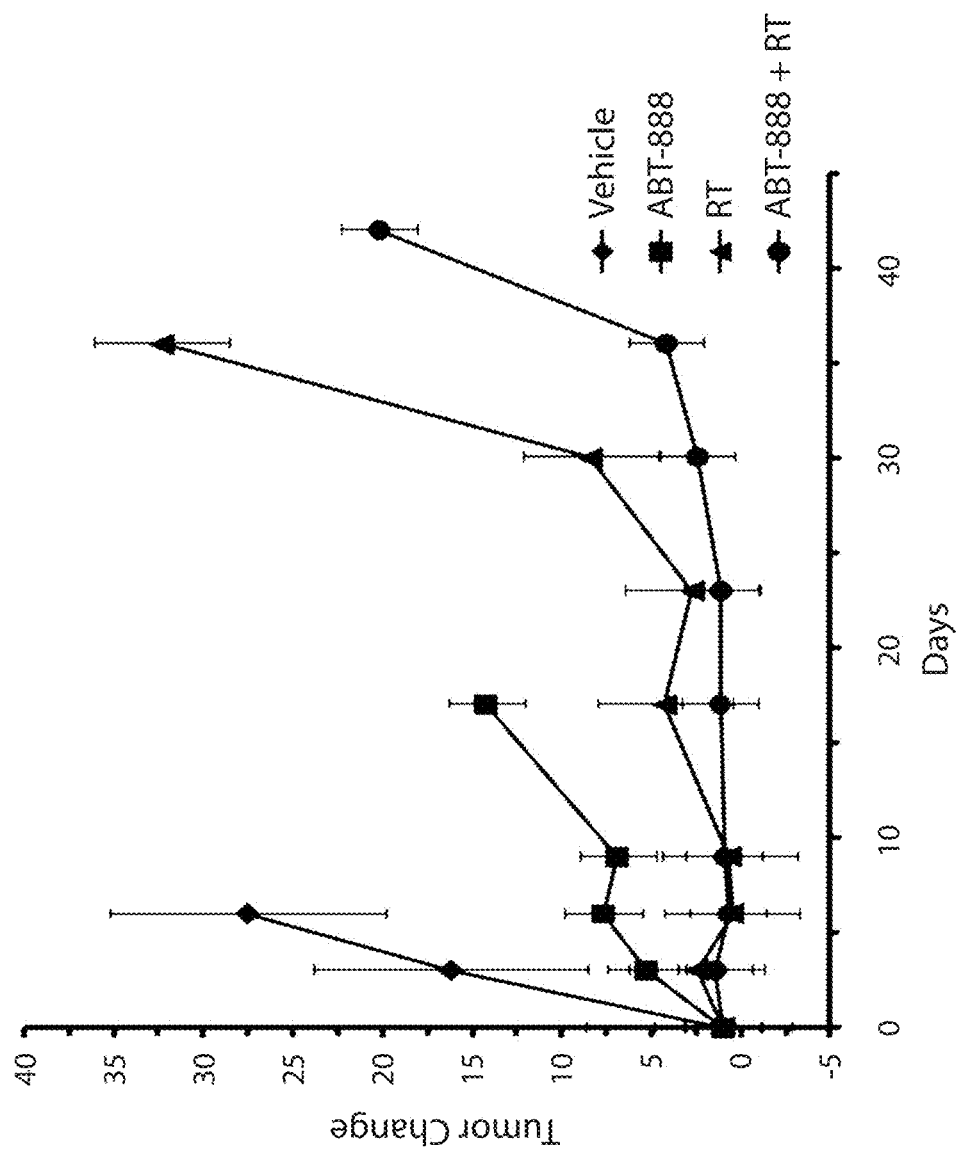

FIG. 15 shows an example of a simulated trial when the true value of the MTD $\gamma=70$ mg and the probability of DLT at the initial dose is 0.05 assuming 30 patients have been enrolled. Patients enter the trial according to a time homogeneous Poisson process with an average number of 3 patients per 10 weeks (1 cycle=10 weeks). The figure shows patients number, the time when they enter the trial, the DLT status and how long it took to exhibit DLT if they did. This shows that in the absence of DLT, the allocated dose tends to go up and the recommended dose drops whenever DLTs are encountered. For example, patient #1 is given a dose of 20 mg and has no DLT by the end of 10 weeks. Patients 2, 3, 4 were given higher doses because there was no DLT by the time patient #4 was enrolled. Patients 5 and 6 were still given higher doses because by the time they were enrolled in the trial, patient #4 did not experience DLT. However, the dose for patient #7 drops because by the time this patient is enrolled, patient #4 had exhibited DLT.

Design Operating Characteristics

We simulated 1000 trials under 3 scenarios for the true value of the MTD $\gamma$. In each case, the probability of DLT at the initial doe is 0.05, the arrival times follow a time homogeneous Poisson process with rate 3 per cycle. Sample sizes of n=20 and n=30 patients per trial were used. Table 5 shows the summary statistics based on 1000 trials. The estimated MTD is close to the true underlying $\gamma$ when $\gamma=0.4$, 0.7 but the bis is higher when the true MTD is high and the overdose protection property of EWOC is illustrated by the observed rate of DLTs.

TABLE 5

Design operating characteristics

| | True MTD $\gamma$ | | |
|---|---|---|---|
| Based on 1000 trial replicates | 40 | 70 | 100 |
| Estimated MTD (n = 30) | 49 | 71.8 | 83.9 |
| Proportion of DLT (n = 30) | 21.1% | 16.2% | 12.4% |
| Estimated MTD (n = 20) | 50.1 | 70.4 | 79.6 |
| Proportion of DLT (n = 20) | 21% | 14.7% | 11.1% |

Example 3

Figure 26:
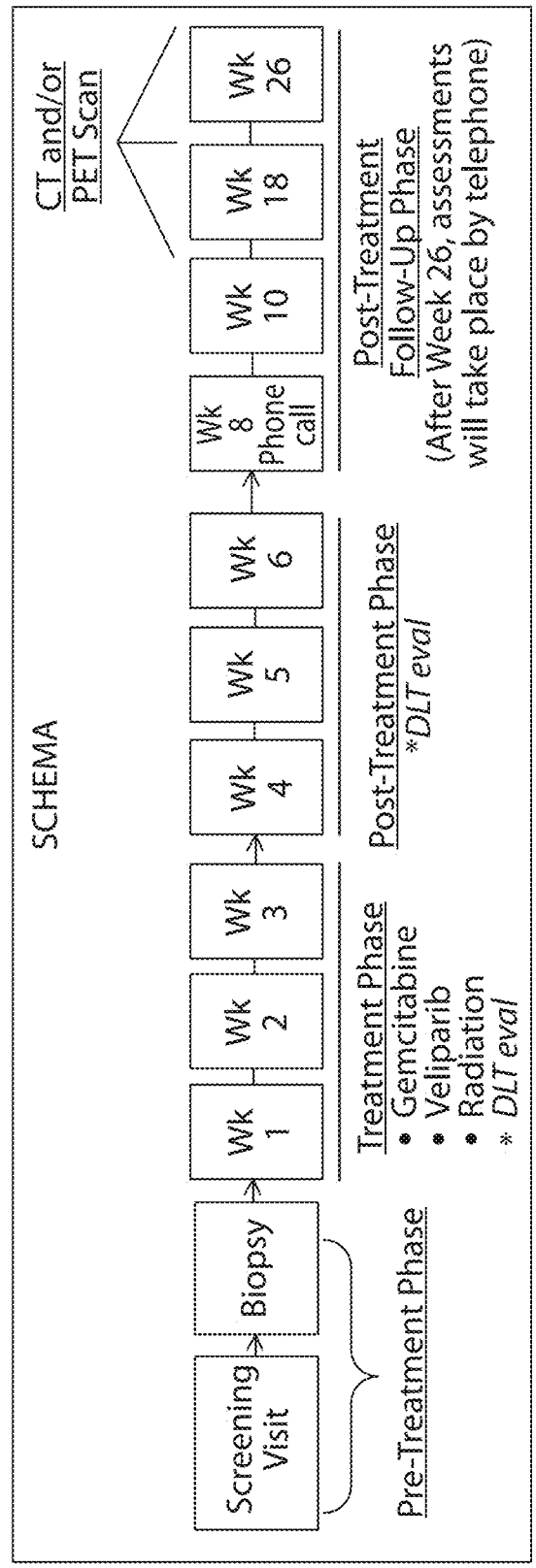
FIG. 26 depicts a dose escalation scheme.

A Phase I study using ABT-888 (VELiparib) in combination with GEMcitabine and intensity modulated RADiation therapy (IMRT) for Locally Advanced Prostate Cancer was conducted (VelGemRad). The combination treatment was administered in the following doses: Gemcitabine—IV infusion of 1000 mg/m² on days 1, 8, 15 of the cycle; IMRT—36 Gy in 15 fractions (2.4 Gy/day, M-F) and Veliparib—administered per dose escalation schema (see FIG. 26).

The primary objective was to determine the maximum tolerated dose (MTD), safety and toxicity profile. The secondary objective was to measure the clinical activity of the treatment (progression free survival—PFS, overall survival—OS) and evaluate patient tumor or blood pre-, during and post treatment for DNA damage repair alterations, PAR levels and immune mediators. Between 2013 and 2016, 34 patients enrolled at a single institution. Four were removed due to non-compliance. The median age was 67 and 24 were LAPC and 6 were borderline resectable prostate cancer (BR).

TABLE 6

VelGEMRAD - Safety

| Dose levels/Cohort | # of PTs Dosed | # of DLTs | # of Pts w/DLTs | Action by PI |
|---|---|---|---|---|
| ABT-888 20 mg BID; Gem 1000 mg/m²; RT 36 Gy/(Arm 1) | 1 | 4 | 1 | Starting dose |
| ABT-888 20 mg BID; Gem 750 mg/m²; RT 36 Gy/(Arm 5) | 1 | 2 | 1 | Dose reduced gemzar to 750 mg/m² |
| ABT-888 20 mg BID; Gem 500 mg/m²; RT 36 Gy/(Arm 6) | 1 | 1 | 1 | Dose reduced gemzar to 500 mg/m² |
| ABT-888 20 mg BID; Gem 400 mg/m²; RT 36 Gy/(Arm 7) | 2 | 0 | 0 | Dose reduced gemzar to 400 mg/m² |
| ABT-888 40 mg BID; Gem 400 mg/m²; RT 36 Gy/(Arm 9) | 9 | 1 | 1 | Dose escalated ABT-888 to 40 mg BID |
| ABT-888 60 mg BID; Gem 400 mg/m²; RT 36 Gy/(Arm 10) | 20 | 8 | 8 | Dose escalated ABT-888 to 60 mg BID |
| Total | 34* | 16 | 12 | |

*34 patients have been dosed on study as of the data cut-off date of 29 Jul. 16.

The MTD was veliparib 40 mg BID in combination with gemcitabine 400 mg/m² and RT (36 Gy). 16 DLTs identified in 12 of 30 evaluable patients (lymphopenia (10), neutropenia (1), febrile neutropenia (1), abdominal infection (1), abdominal pain (1), hyponatremia (1), and leukopenia (1). No significant GI toxicities were observed.

Mutations in DDR genes: ARID1A (4), ATM-x (1), CHEK2-D293fs*1 (2), PALB2-V836I (1), PTEN (1) and MLH1-loss (1). There was no improvement in PFS or OS for patients with such mutations (p=0.38, p=0.9), respectively. Of 10 DDR alterations, 1 patient harbored alterations in more than one gene. Patient 8: LAPC with CHEK2/MLH1 mutation—downstaged to margin—'ve resection; PFS 20 mos and OS 24 mos; and Patient 12: LAPC with PALB2 mutation—downstaged to margin—'ve resection; NED 23 mos.

Combination treatment in TMB (25/34 pts), mTMB 1.8 mut/Mb, range 0-23.4 mut/Mb. Patients with DNA damage repair deficiency identified by transcriptome analysis/NGS were more likely to have increased TMB. 1 patient had hTMB (mut/Mb >20)—CHEK2/MLH1 mut (NGS) and 24 pts had low TMB (mutations/Mb<1=20)—DDR WT (NGS). Combination treatment in MSI (18/34 pts), 1 patient MSI-H—hTMB—CHEK2/MLH1 mut (NGS). All remaining DDR deficient patients (89%) were MSS.

Figure 10:
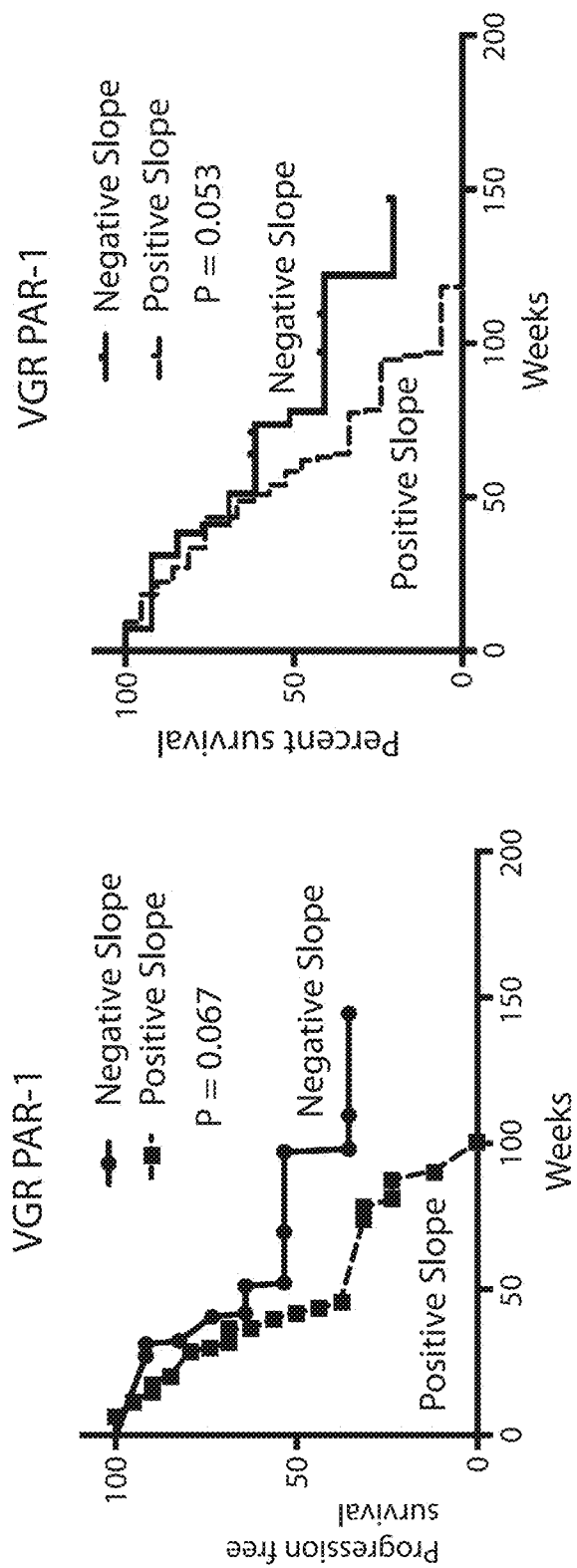
FIG. 10 depicts in accordance with various embodiments of the invention, the VelGemRad—PARP inhibitor and PAR ELISA.
Figure 11A:
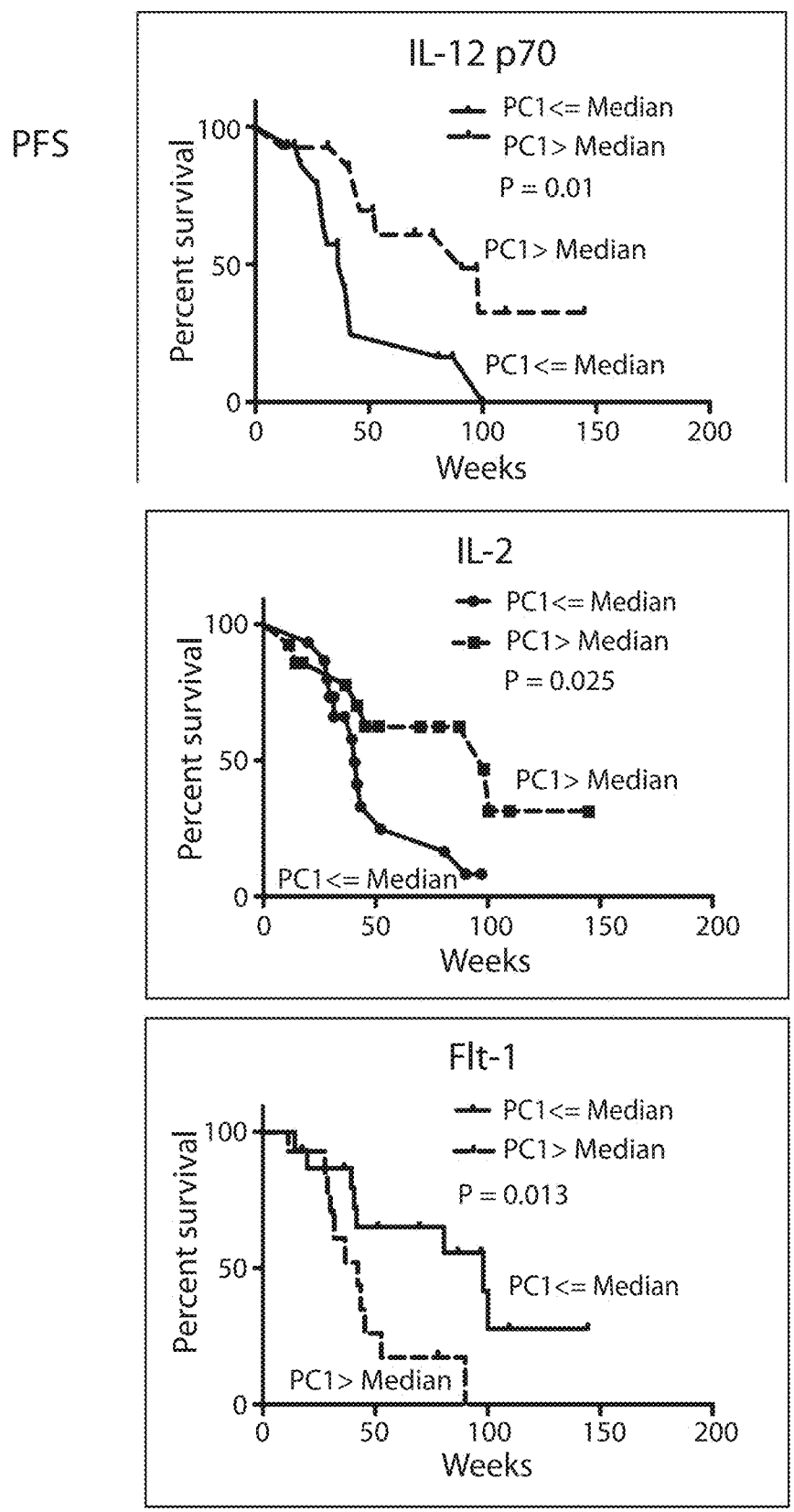
FIG. 11A-11B depicts in accordance with various embodiments of the invention, the VelGemRad—cytokine analysis.
Figure 11B:
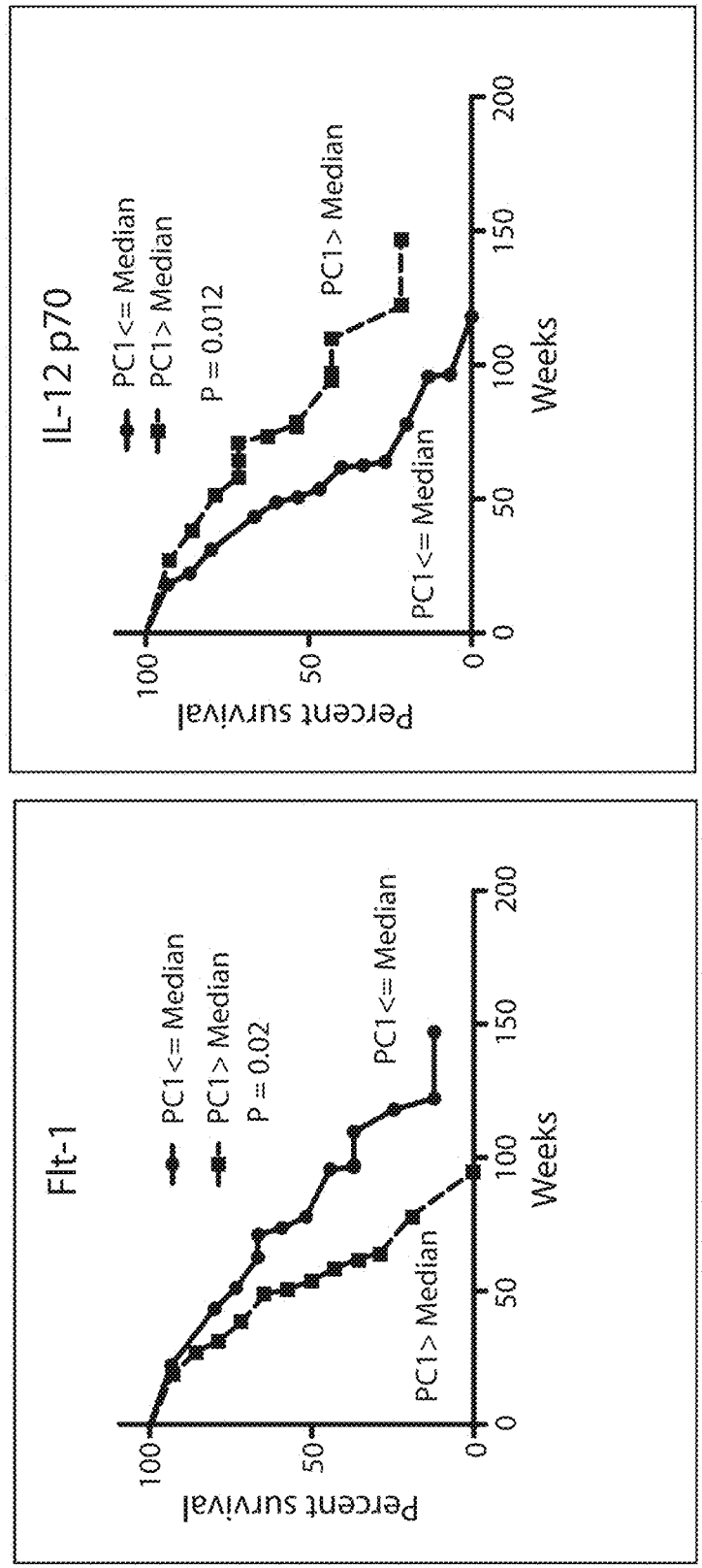
Figure 12:
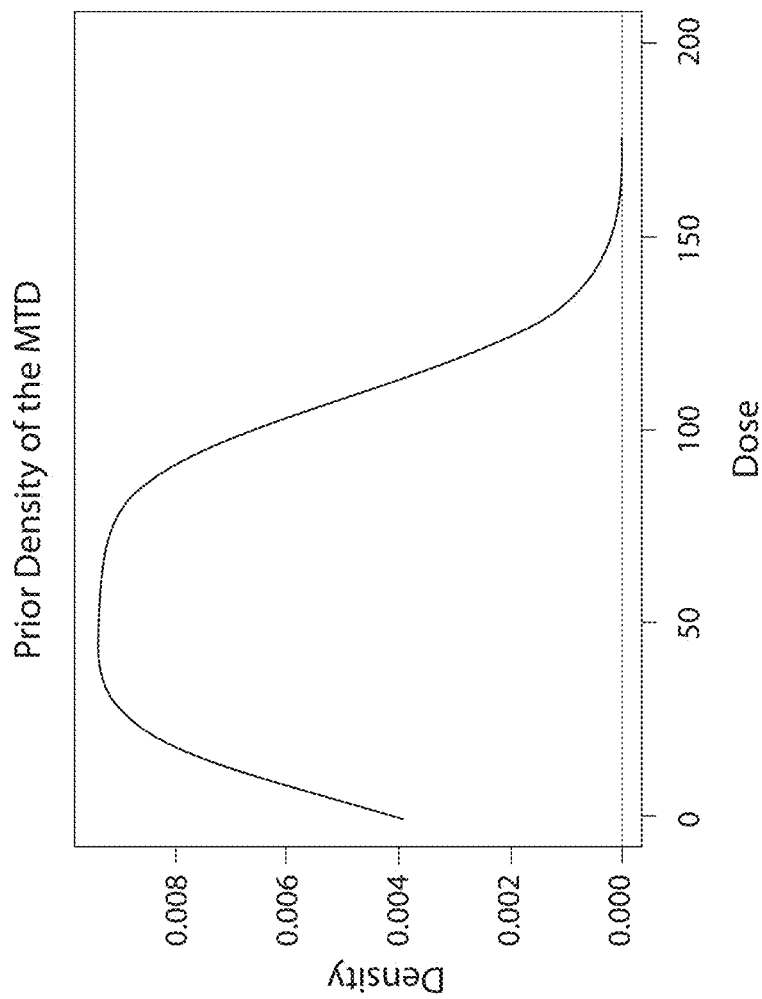
FIG. 12 depicts in accordance with various embodiments of the invention, the density of the maximum tolerable dose (MTD).
Figure 13:
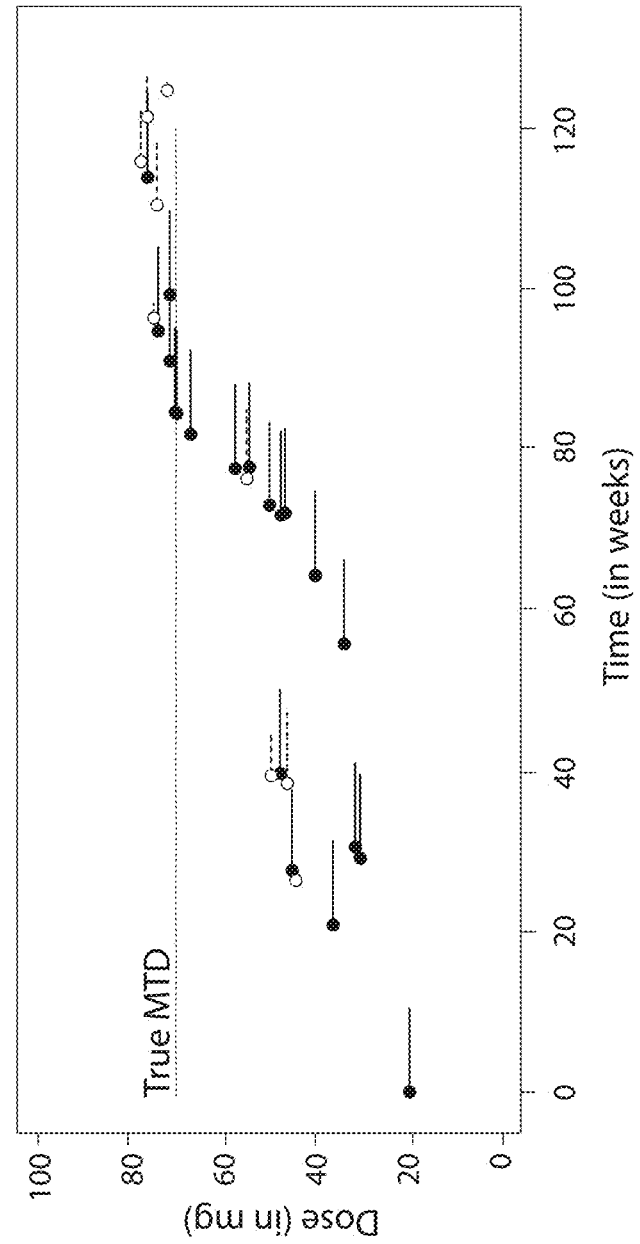
FIG. 13 depicts in accordance with various embodiments of the invention, simulated trial with the true MTD (70 mg).
Figure 14:
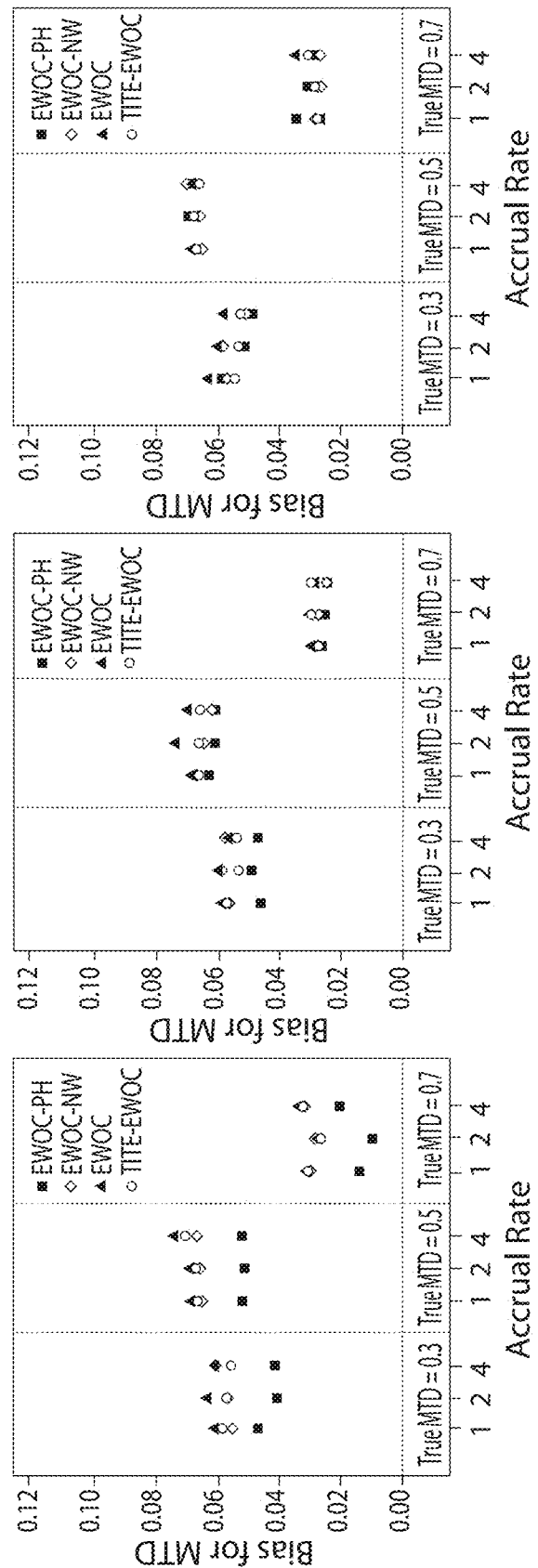
FIG. 14 depicts in accordance with various embodiments of the invention, the average of the estimate of the MTD under the nine different scenarios. DLT responses are generated from a Weibull model with shape parameter k–0.8 (left plot), 1=1.0 (middle plot), and k=1.2 (right plot).

PAR protein levels were assessed as a surrogate for PARP inhibition as a function of time and clinical outcomes (FIG. 10). Patients with decreased PAR levels had borderline significant improved PFS (P=0.067) and OS (P=0.053).

PARP Inhibitor, Gemcitabine and Radiation Therapy

A randomized double blind placebo-controlled phase II trial of gemcitabine and hypofractionated radiotherapy with or without talazoparib in patients with DNA repair deficient (DDR) locally advanced pancreatic cancer (LAPC) was performed to identify LAPC with DDR deficiency and randomize to treatment with or without PARP1/2 inhibitor, talazoparib.

RNA sequence libraries prepared from pre-treatment EUS-guided fine needle core biopsies. DAVID v6.7 is used to interpret transcriptomic differential expression of genes related to the following 'biomarker' pathways: NER, MMR, BER, DNAR, FA. Without being bound to any particular theory, the inventors believe that the clinical outcomes (PFS, OS) will be significantly better in biomarker positive patients receiving talazoparib.

The initial cohort includes treatment with Gemcitabine(*) 600 mg/m$^2$ weekly×3+IMRT 36 GY/15 fractions+talazoparib 1 mg/daily×21 days. (*) If the treatment is not safe, up to 3 additional safety lead-in cohort will be assessed at gemcitabine levels of: 500 mg/m$^2$, 400 mg/m$^2$ and 250 mg/m$^2$. Talazoparib (1 mg/day for 21 days), gemcitabine (600 mg/m$^2$, once per week for 3 weeks) and RT (36 Gy/15, 5 fxs/wk) is administered as treatment. The treatment cycle is 3 weeks followed by a 3 week DLT evaluation period. If DLT, gemcitabine dose reduced (DL-1: 500 mg/m2, DL-2: 400 mg/m$^2$, DL-3: 250 mg/m2, DL-4: no gem). Talazoparib will be maintained without dose reduction.

Randomized Phase II

Patients receive up to 6 months of SOC chemorapy (5FU or gem-based). Patients stratified by +/−DDR deficiency biomarker determined by RNA sequence analysis of pre-treatment tumor biopsy. Randomized to gemcitabine (DL per safety lead-in)+IMRT (36 Gy in 15 fractions) with talazoparib (1 mg/day for 21 days) or placebo, in a 2:1 ratio in favor of talazoparib.

Example 4

Locally advanced pancreatic cancer (LA) has a dismal prognosis with current treatment modalities. Preclinical studies have demonstrated radiosensitization of orthotopic pancreatic tumors with the PARP-1/2 inhibitor, veliparib. A phase I trial of veliparib (V), gemcitabine (G) and radiotherapy (RT) was conducted to determine the maximum tolerated dose (MTD), safety and clinical activity of this regimen in patients with and without DNA damage repair (DDR) defects, as well to identify other variables associated with response.

Treatment naïve patients with LA or borderline resectable pancreatic cancer (BR) were treated with weekly G (1000 mg/m$^2$), daily RT (36 Gy/15 fractions) and V 20 mg BID daily for 3 weeks escalated per Bayesian method followed by standard chemotherapy. DAVID v6.7 was used to interpret transcriptomic differential expression of genes. Cox regression model was used to identify DDR pathways associated with survival. Next generation sequencing (NGS) identified genetic mutations involved in DDR, tumor mutation burden (TMB) and microsatellite instability (MSI) status. Weekly blood samples were interrogated for PAR protein quantities using ELISA and cytokines using the MesoScale V-Plex electrochemiluminescent array. The log-rank test was used to evaluate differences in PFS and OS.

34 patients were enrolled from September 2013 to May 2016. Four were removed due to non-compliance. 4 (13.3%) and 26 (86.7%) patients had BR and LA, respectively. MTD of veliparib was 40 mg BID with gemcitabine 400 mg/m$^2$ and RT (36 Gy/15). 12 patients experienced DLT (83.3% lymphopenia, 8.3% neutropenia, febrile neutropenia, abdominal infection, abdominal pain, hyponatremia, and leukopenia.) The most frequent grade >/=3 AEs were lymphocyte count decreased, hyperglycemia, and anemia. Median PFS and OS for the entire cohort were 9.8 months (95% CI: 8.4-18.6) and 14.6 months (95% CI: 11.6-21.8), respectively. Gene expression analysis identified 50% of patients harboring DNA repair defects. Median PFS and OS were significantly higher for these biomarker positive (+) compared to negative (−) patients (17 vs. 8 mos, p<0.01; 22 vs. 12 mos, p<0.001, respectively). NGS identified 10 DDR mutations which were not prognostic of outcome. median TMB was 1.8 mutations/Mb (range 0-23). Only 1 patient had high TMB (mutations/Mb >20). A single MSI high patient was identified who was also TMB high and harbored DNA damage repair deficiency by NGS. Higher levels of IL2 and IL12 lower levels of FLT1 were associated with improved PFS and OS.

The combination of V, G and RT was well tolerated. DDR alterations were identified in a large proportion of patients and were associated with significant improvement in PFS and OS. Alterations in more DDR-related pathways led to better outcomes. Whereas most patients were MSS and harbored low TMBs, patients with higher levels of pro-inflammatory cytokines were also likely to harbor DDR alterations, which predicted response to the treatment combination.

Example 5

The phase 1 lead-in determines the safety and MTD of olaparib (DL1: 25 mg BID for 21 days) in combination with gemcitabine (600 mg/m$^2$, once per week for 3 weeks) and IMRT (36 Gy in 15 fractions, 5 fractions per week). The treatment cycle is 3 weeks followed by a 3 week DLT evaluation period. If DLT is encountered at dose level 1 (DL1) of olaparib, gemcitabine is dose reduced (DL-1: 400 mg/m$^2$, DL-2: 250 mg/m$^2$, DL-3: no gemcitabine). If no DLT is reached, olaparib is dose escalated (DL2: 50 mg BID; DL3: 100 mg BID).

Gemcitabine (dose per safety lead-in), IMRT (36 Gy in 15 fractions, 5 fractions per week), and olaparib (dose per safety lead-in).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A process, comprising
    obtaining a biological sample from a human subject;
    assaying the biological sample to determine the presence or absence of a defect in each of the following DNA repair pathway genes: RFC2, ERCC1, XPA, CUL4A, FANCE, MCM4, NEIL1, PARP3, APEX2, ARID1A, ATM, CHEK2-D293fs*1, PALB2-V836I, PTEN, and MLH1;
    determining the presence of defects in four or more DNA repair pathways in the biological sample based on the detection of the presence of defects in four or more of the DNA repair pathway genes,
        wherein the DNA repair pathways comprise nucleotide excision repair (NER) pathway, fanconi anemia (FA) pathway, DNA replication (DNAR) pathway, base excision repair (BER) pathway, and mismatch repair (MER) pathway,
        wherein RFC2, ERCC1, XPA, and CUL4A are NER pathway genes, ERCC1 and FANCE are FA pathway genes, RFC2 and MCM4 are DNAR pathway genes, and NEIL1, PARP3, and APEX2 are BER pathway genes; and
    administering a therapeutically effective amount of a composition comprising a Poly (ADP-ribose) polymerase (PARP) inhibitor to the human subject, determined to have defects in four or more DNA repair pathways, to treat pancreatic cancer.

2. The process of claim 1, wherein the pancreatic cancer is locally advanced pancreatic cancer.

3. A method of treating pancreatic cancer, comprising:
   administering a therapeutically effective amount of a composition comprising a Poly (ADP-ribose) polymerase (PARP) inhibitor to a human subject to treat pancreatic cancer,
   wherein a biological sample from the human subject has been assayed to determine the presence or absence of a defect in each of the following DNA repair pathway genes: RFC2, ERCC1, XPA, CUL4A, FANCE, MCM4, NEIL1, PARP3, APEX2, ARID1A, ATM, CHEK2-D293fs*1, PALB2-V836I, PTEN, and MLH1; and
   wherein defects in four or more DNA repair pathways were determined to be present in the biological sample based on the detection of the presence of defects in four or more of the DNA repair pathway genes,
      wherein the DNA repair pathways comprise nucleotide excision repair (NER) pathway, fanconi anemia (FA) pathway, DNA replication (DNAR) pathway, base excision repair (BER) pathway, and mismatch repair (MER) pathway, and
      wherein RFC2, ERCC1, XPA, and CUL4A are NER pathway genes, ERCC1 and FANCE are FA pathway genes, RFC2 and MCM4 are DNAR pathway genes, and NEIL1, PARP3, and APEX2 are BER pathway genes.

4. The method of claim 3, further comprising: administering a therapeutically effective amount of radiation therapy or administering a therapeutically effective amount of chemotherapy, or both.

5. The method of claim 3, wherein the PARP inhibitor is talozoparib, olaparib, and/or niraparib.

6. The method of claim 3, wherein the pancreatic cancer is locally advanced pancreatic cancer.

7. The method of claim 4, wherein the PARP inhibitor is olaparib, the radiation therapy is intensity-modulated radiation therapy (IMRT), and the chemotherapy is gemcitabine.

8. The method of claim 4, wherein:
   the PARP inhibitor is olaparib and is administered 25 mg twice per day,
   the radiation therapy is intensity-modulated radiation therapy (IMRT) and is administered at a dose of 36Gy in 15 fractions with 5 fractions per week, and
   the chemotherapy is gemcitabine and is administered 600 mg/m$^2$ once per week for 3 weeks.

9. The method of claim 4, wherein:
   the PARP inhibitor is olaparib and is administered 25 mg twice per day,
   the radiation therapy is intensity-modulated radiation therapy (IMRT) and is administered at a dose of 36Gy in 15 fractions with 5 fractions per week, and
   the chemotherapy is gemcitabine and is administered 400 mg/m$^2$ or 250 mg/m$^2$ once per week for 3 weeks, or chemotherapy is not administered.

10. The method of claim 4, wherein:
    the PARP inhibitor is olaparib and is administered 50 mg or 100 mg twice per day,
    the radiation therapy is intensity-modulated radiation therapy (IMRT) and is administered at a dose of 36Gy in 15 fractions with 5 fractions per week, and
    the chemotherapy is gemcitabine and is administered 600 mg/m$^2$ once per week for 3 weeks.

* * * * *